United States Patent [19]

Almansa et al.

[11] Patent Number: 5,272,170

[45] Date of Patent: Dec. 21, 1993

[54] TETRALONES WITH PHARMACOLOGICAL ACTIVITY

[75] Inventors: Carmen Almansa; Carmen Torres; Concepcion Gonzalez; Elena Carceller; Javier Bartroli, all of Barcelona, Spain

[73] Assignee: J. Uriach & Cia., S.A., Barcelona, Spain

[21] Appl. No.: 6,852

[22] Filed: Jan. 22, 1993

Related U.S. Application Data

[62] Division of Ser. No. 801,000, Dec. 2, 1991, Pat. No. 5,208,246.

[30] Foreign Application Priority Data

Dec. 5, 1990 [ES] Spain .................................. 90 03308
May 9, 1991 [ES] Spain .................................. 91 01242

[51] Int. Cl.$^5$ .................... A61K 31/40; C07D 207/26; C07D 209/46
[52] U.S. Cl. ................... 514/418; 514/424; 514/425; 548/482; 548/550; 548/551
[58] Field of Search ............. 548/482, 550, 551; 514/416, 417, 424, 425, 418

[56] References Cited

U.S. PATENT DOCUMENTS 4,049,717 9/1977 Asato .................................. 548/480

OTHER PUBLICATIONS

Allinger, N. L., et al., *J. Org. Chem.*, 1962, 27, 70.
Klemm, L. H., et al., *J. Org. Chem.*, 1968, 33, 1480.
Hamilton et al., *Br. J. Pharmacol.*, 1986, 88, 103–111.
Emmerson, J. et al., *J. Pharm. Pharmacol.*, 1979, 31, 798.
Rosowsky, A. et al., *J. Heterocycl. Chem.*, 1971, 8, 809.
Itoh, K. et al., *Chem. Pharm. Bull.*, 1984, 32, 130.
Griffin, R. W., et al., *J. Org. Chem.*, 1964; 29, 2109.

Primary Examiner—C. Warren Ivy
Assistant Examiner—Phyllis G. Spivack
Attorney, Agent, or Firm—Rothwell, Figg, Ernst & Kurz

[57] ABSTRACT

The present invention relates to new tetralones having the formula I:

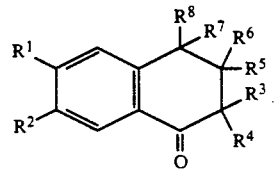

wherein:
$R^1$ and $R^2$ represent hydrogen, halogen, cyano, $C_{1-4}$ alkyl, $C_{1-4}$ alkoxy, trifluoromethyl, pentafluoroethyl, ethynyl, trimethylsilylethynyl, $C_{1-4}$ alkylcarbonylamino being the amino optionally substituted by a $C_{1-4}$ alkyl group; $R^3$ is hydrogen or $C_{1-4}$ alkyl, and $R^4$ is $C_{1-4}$ alkyl, or $R^3$ and $R^4$ together form a $C_{2-5}$ polymethylene chain; either $R^5$ represents hydroxyl, acetoxy or formyloxy and $R^6$ and $R^7$ are both hydrogen, or $R^5$ together with $R^6$ form a carbonyl group and $R^7$ is hydrogen, or $R^5$ and $R^7$ together form a bond and $R^6$ is hydrogen; $R^8$ is, among others, 1,2-dihydro-2-oxo-1-pyridyl, 2,3-dihydro-1-oxo-1H-isoindol-2-yl, 2-oxo-1-pyrrolidinyl, 2-oxo-1-pyperidinyl. The invention also relates to a procedure for their preparation and to pharmaceutical compositions containing them. These compounds are antihypertensive and bronchodilator agents.

12 Claims, No Drawings

TETRALONES WITH PHARMACOLOGICAL ACTIVITY

This is a division of Ser. No. 07/801,000 filed Dec. 2, 1991 now U.S. Pat. No. 5,208,246.

FIELD OF THE INVENTION

The present invention relates to new tetralones with pharmacological activity. The invention also relates to a process for their preparation, to pharmaceutical compositions containing them and to their use in the treatment and/or prophylaxis of the diseases related with the regulation of the smooth muscle contraction in mammals, including man. Such tetralones have been found to have blood pressure lowering activity, useful in the treatment of hypertension, as well as bronchodilatory activity, useful in the treatment of asthma. They are also indicated in the treatment of other diseases related with the regulation of the smooth muscle contraction in the gastrointestinal, uterus or urinary tract and in the cardiovascular, respiratory or cerebrovascular systems. Such disorders include angina, congestive heart failure, incontinence, irritable bowel syndrome and epilepsy.

DESCRIPTION OF THE INVENTION

The present invention relates to new tetralones of general formula I:

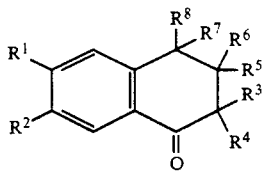

wherein:

$R^1$ and $R^2$ represent hydrogen, $C_{1-4}$ alkyl, hydroxyl, $C_{1-4}$ alkoxy, formyl, $C_{1-4}$ alkylcarbonyl, $C_{1-4}$ alkylthiocarbonyl, carboxyl, $C_{1-4}$ alkoxycarbonyl, $C_{1-4}$ alkoxythiocarbonyl, $C_{1-4}$ alkylcarbonyloxy, $C_{1-4}$ alkylthiocarbonyloxy, hydroxy($C_{1-4}$) alkyl, mercapto-($C_{1-4}$) alkyl, perfluoro($C_{1-4}$)alkyl, nitro, amino, cyano, halogen, trifluoromethoxy, ethynyl, trimethylsilylethynyl, $C_{1-4}$ alkylsulphinyl, arylsulphinyl, $C_{1-4}$ alkylsulphonyl, arylsulphonyl, $C_{1-4}$ alkoxysulphinyl, $C_{1-4}$ alkoxysulphonyl, $C_{1-4}$ alkylcarbonylamino, $C_{1-4}$ alkoxycarbonylamino, aminosulphinyl, aminosulphonyl, aminocarbonyl, aminothiocarbonyl, $C_{1-4}$ alkylsulphinylamino, $C_{1-4}$ alkylsulphonylamino, $C_{1-4}$ alkoxysulphinylamino, $C_{1-4}$ alkoxysulphonylamino, ($C_{1-4}$ alkyl)carbonyl($C_{1-4}$ alkyl), nitro-($C_{1-4}$ alkyl), cyano-($C_{1-4}$ alkyl), ($C_{1-4}$ alkyl)C(=NOH), ($C_{1-4}$ alkyl)C(=NNH$_2$) or ($C_{1-4}$ alkoxy)C(=NH), being the above amino groups optionally substituted by one or two $C_{1-4}$ alkyl groups;

$R^3$ is hydrogen or $C_{1-4}$ alkyl; $R^4$ is $C_{1-4}$ alkyl, or $R^3$ and $R^4$ together form a $C_{2-5}$ polymethylene chain;

either $R^5$ represents hydroxyl, acetoxy or formyloxy and $R^6$ and $R^7$ are both hydrogen; $R^5$ together with $R^6$ form a carbonyl group and $R^7$ is hydrogen; or $R^5$ and $R^7$ together form a bond and $R^6$ is hydrogen;

$R^8$ is 1,2-dihydor-2-oxo-1-pyridyl (1H-2-Pyridon-1-yl), 1,6-dihydro-6-oxo-1-pyridazinyl (1H-6-Pyridazinon-1-yl), 1,2-dihydro-2-oxo-1-pyrimidinyl (1H-2-Pyrimidinon-1-yl), 1,6-dihydro-6-oxo-1-pyrimidinyl (1H-6-Pyrimidinon-1-yl), 1,2-dihydro-2-oxo-1-pyrazinyl (1H-2-Pyrazinon-1-yl), 1,2-dihydro-2-thioxo-1-pyridyl (1H-2-Thiopyridon-1-yl), 2,3-dihydro-1-oxo-1H-isoindol-2-yl, 1-oxo-1,2,3,4-tetrahydroisoquinol-2-yl, being all of them optionally substituted by a group $R^9$, or 2-oxo-1-pyrrolidinyl (2-Pyrrolidinon-1-yl), 2-oxo-1-pyperidinyl (2-Pyperidinon-1-yl), 2-thioxo-1-pyrrolidinyl (2-Thiopyrrolidinon-1-yl), 2-thioxo-1-pyperidinyl (2-Thiopyperidinon-1-yl), being these four radicals optionally substituted by a group $R^{10}$;

$R^9$ is a fluorine, chlorine, bromine or iodine atom or a $C_{1-4}$ alkyl, hydroxyl, nitro, or amino group, being the amino group optionally substituted by one or two $C_{1-4}$ alkyl groups;

$R^{10}$ is a $C_{1-4}$ alkyl, hydroxyl, $C_{1-4}$ hydroxyalkyl, $C_{1-4}$ alkoxymethyl, $C_{1-4}$ thioalkoxymethyl or aminomethyl group, being the amino group optionally substituted by one or two $C_{1-4}$ alkyl groups;

and the salts thereof.

The invention also provides the use of at least one compound of formula I or a pharmaceutically acceptable salt thereof in the treatment and/or prophylaxis of the diseases related with the regulation of the smooth muscle contraction at the cardiovascular, respiratory and cerebrovascular systems, and at the gastrointestinal, urinary and uterus tracts, and particularly for the treatment and/or prophylaxis of hypertension and asthma in mammals, including man.

The invention further provides a pharmaceutical composition comprising an effective amount of at least one compound of formula I or a pharmaceutically acceptable salt thereof in admixture with a pharmaceutically acceptable excipient.

The invention still further provides processes for preparing the compounds of formula I, which in general terms comprise:

(a) when in a compound of general formula I, $R^5$ is OH and $R^6$ and $R^7$ are H, reacting a compound of general formula V, wherein $R^{1'}$ and $R^{2'}$ are $R^1$ or $R^2$ as defined above or a group or atom convertible thereto, and $R^3$ and $R^4$ have the previously defined meaning,

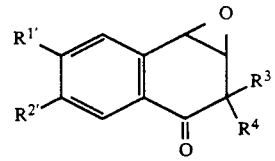

with a compound of formula $R^8$-H (XI, wherein $R^8$ has the previously defined meaning) in the presence of a base such as sodium hydride in a suitable solvent such as dimethylsulphoxide or dimethylformamide or in the presence of pyridine in a suitable solvent such as ethanol; or alternatively, in the particular case where $R^8$ is 1H-2-Pyridon-1-yl, reacting a compound of formula V with 2-trimethylsilyloxypyridine (XII) in a suitable solvent, such as tetrahydrofurane, in the presence of tetrabutylammonium fluoride; or alternatively (b) when in a compound of general formula I, $R^5$ is OH, $R^6$ and $R^7$ are H, and $R^8$ is 2-oxo-1-pyrrolidinyl or 2-oxo-1-pyperidinyl optionally substituted by an $R^{10}$ group, I may also be obtained either by reacting said compound V with ammonia in a suitable solvent such as ethanol or a mixture of ethanol and water, to give a compound of general formula VI:

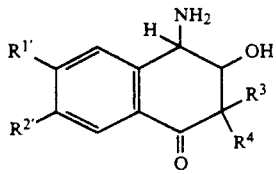

wherein $R^{1'}$, $R^{2'}$, $R^3$ and $R^4$ have the previously defined meaning, and then reacting said compound VI with a compound of general formula Y-A-COY (XIII, wherein Y means a good leaving group such as a chlorine, bromine or iodine atom and A represents a trimethylene or a tetramethylene group optionally substituted by an $R^{10}$ group) in the presence of a base such as triethylamine or sodium hydroxide in a suitable solvent such as chloroform, methylene chloride or a mixture of chloroform and water, to give a compound of general formula VII:

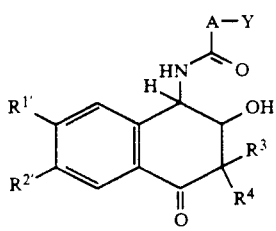

wherein $R^{1'}$, $R^{2'}$, $R^3$, $R^4$, Y and A have the previously defined meaning, and finally reacting said compound VII in the presence of a base such as potassium carbonate in a suitable solvent such as acetone; or by reacting V with a compound of general formula $NH_2$-A-CO-Z (XIV, wherein A has the previously defined meaning and Z is an hydroxyl or alkoxy group) in an alcoholic solvent such as ethanol or alternatively reacting VI with a compound of general formula Y-A-CO-Z (XV, wherein Y, A and Z have the previously defined meaning), to give a compound of general formula VIII:

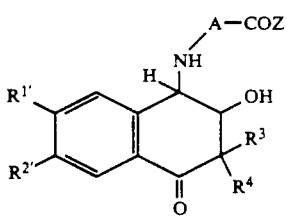

wherein $R^{1'}$, $R^{2'}$, $R^3$, $R^4$, Z and A have the previously defined meaning, and cyclizing said compound VIII in an inert solvent such as toluene or xylene at reflux; or (c) when in a compound of general formula I, $R^5$ is OH, $R^6$ and $R^7$ are H, and $R^8$ is 2,3-dihydro-1-oxo-1H-isoindol-2-yl or 1-oxo-1,2,3,4-tetrahydroisoquinol-2-yl optionally substituted by an $R^9$ group, treating a compound of formula VI with a compound of formula XVI:

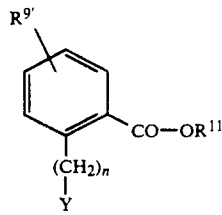

wherein $R^{11}$ is a $C_{1-4}$ alkyl group, n is 1 or 2, $R^{9'}$ is either hydrogen or $R^9$ as above defined, and Y has the previously defined meaning, in the presence of an excess of a base, such as potassium carbonate, and a small amount of potassium iodide in a suitable solvent, such as acetonitrile;

(d) optionally, transforming the carbonyl group on the radical $R^8$ of a thiation reagent such as Lawesson's reagent in a suitable solvent such as toluene;

(e) in all cases wherein $R^5$ is acetoxy and $R^6$ and $R^7$ are hydrogen, reacting a compound of formula I wherein $R^5$ is hydroxyl and $R^6$ and $R^7$ are hydrogen with acetic anhydride in the presence of a base such as pyridine;

(f) in all cases wherein $R^5$ is formyloxy and $R^6$ and $R^7$ are hydrogen with formic acid in the presence of a base such as pyridine;

(g) in all cases wherein $R^5$ and $R^7$ together form a bond, reacting a compound of general formula I wherein $R^5$ is OH and $R^7$ is hydrogen with a base such as sodium hydride or sodium hydroxyde in a suitable solvent such as toluene or dioxane; or reacting a compound of general formula I wherein $R^5$ is acetoxy and $R^7$ is hydrogen with a dehydrating agent such as 1,8-diazabicyclo(5.4.0)undec-7-ene (DBU) in an inert solvent such as toluene; or a spontaneous dehydration takes place during the reaction between the compound of formula V with the amides of formula XI; or heating a compound of formula I wherein $R^5$ is OH and $R^7$ is hydrogen with a salt of a weak acid, such as sodium acetate, in a suitable solvent, such as N-methylpyrrolidone, and optionally, when in the hydroxy derivative $R^1$ or $R^2$ are a bromine atom, transforming simultaneously to the dehydration said bromine atom into a cyano group by using an excess of cuprous cyanide, in the same experimental conditions;

(h) optionally, interconverting the groups $R^1$, $R^2$, $R^{1'}$ and/or $R^{2'}$ in a compound of formula I or any intermediate of formula II-VIII into other groups $R^1$ and/or $R^2$;

(i) and optionally, reacting a compound of formula I with an acid to give its corresponding acid addition salt.

In the compounds of the present invention, a "$C_{1-4}$ alkyl" group can be a linear or branched alkyl chain containing from 1 to 4 carbon atoms, that is to say methyl, ethyl, propyl, isopropyl, butyl, isobutyl, sec-butyl or tert-butyl, of which methyl, ethyl, propyl, isopropyl, butyl and isobutyl are preferred, methyl and ethyl are more preferred, and methyl is most preferred.

In $R^1$ or $R^2$ a $C_{1-4}$ alkoxy group means a group derived from the union of a $C_{1-4}$ alkyl group to an oxygen atom of an ether functional group. Examples include methoxy, ethoxy, propoxy, isopropoxy, butoxy, isobutoxy, sec-butoxy and tert-butoxy, of which methoxy, ethoxy, propoxy, isopropoxy, butoxy and isobutoxy are preferred, and methoxy is most preferred.

In $R^1$ or $R^2$ a $C_{1-4}$ alkylcarbonyl group means a group derived from the union of a $C_{1-4}$ alkyl group to a carbonyl group. Examples include acetyl, propanoyl, isopropanoyl, butanoyl, and isobutanoyl, of which acetyl and propanoyl are preferred, and acetyl is most preferred.

In $R^1$ or $R^2$ a $C_{1-4}$ alkylthiocarbonyl group means a group derived from the union of a $C_{1-4}$ alkyl group to a thiocarbonyl group. Examples include thioacetyl, thiopropanoyl, thioisopropanoyl, thiobutanoyl, and thioisobutanoyl, of which thioacetyl and thiopropanoyl are preferred, and thioacetyl is most preferred.

In $R^1$ or $R^2$ a $C_{1-4}$ alkoxycarbonyl group means a group derived from the union of a $C_{1-4}$ alkoxy group, like the above mentioned, to a carbonyl group, and include methoxycarbonyl, ethoxycarbonyl, propoxycarbonyl, isopropoxycarbonyl, butoxycarbonyl, isobutoxycarbonyl, sec-butoxycarbonyl and tert-butoxycarbonyl, of which methoxycarbonyl, ethoxycarbonyl, propoxycarbonyl, isopropoxycarbonyl, butoxycarbonyl, and isobutoxycarbonyl are preferred, methoxycarbonyl and ethoxycarbonyl are more preferred, and methoxycarbonyl is most preferred.

In $R^1$ or $R^2$ a $C_{1-4}$ alkoxythiocarbonyl group means a group derived from the union of a $C_{1-4}$ alkoxy group, like the above mentioned, to a thiocarbonyl group, and include methoxythiocarbonyl, ethoxythiocarbonyl, propoxythiocarbonyl, isopropoxythiocarbonyl, butoxythiocarbonyl, isobutoxythiocarbonyl, sec-butoxythiocarbonyl and tert-butoxythiocarbonyl, of which methoxythiocarbonyl, ethoxythiocarbonyl, propoxythiocarbonyl, isopropoxythiocarbonyl, butoxythiocarbonyl, and isobutoxythiocarbonyl are preferred, methoxythiocarbonyl and ethoxythiocarbonyl are more preferred, and methoxythiocarbonyl is most preferred.

In $R^1$ or $R^2$ a $C_{1-4}$ alkylcarbonyloxy group means a group derived from the union of a $C_{1-4}$ alkylcarbonyl group to an oxygen atom. Examples include acetoxy, propanoxy, isopropanoxy, butanoxy, and isobutanoxy, of which acetoxy and propanoxy are preferred, and acetoxy is most preferred.

In $R^1$ or $R^2$ a $C_{1-4}$ alkylthiocarbonyloxy group means a group derived from the union of a $C_{1-4}$ alkylthiocarbonyl group to an oxygen atom. Examples include thioacetoxy, thiopropanoxy, thioisopropanoxy, thiobutanoxy, and thioisobutanoxy, of which thioacetoxy and thiopropanoxy are preferred, and thioacetoxy is most preferred.

In $R^1$ or $R^2$ a hydroxy-$C_{1-4}$ alkyl group means a group resulting from the substitution of one hydrogen atom of the above mentioned "$C_{1-4}$ alkyl" group by an hydroxyl group. Examples include hydroxymethyl, 1-hydroxyethyl, 2-hydroxyethyl, 1-hydroxypropyl, 2-hydroxypropyl, and 3-hydroxypropyl, of which hydroxymethyl, 1-hydroxyethyl and 2-hydroxyethyl are preferred.

In $R^1$ or $R^2$ a mercapto-$C_{1-4}$ alkyl group means a group resulting from the substitution of one hydrogen atom of the above mentioned "$C_{1-4}$ alkyl" group by a mercapto group. Examples include mercaptomethyl, 1-mercaptoethyl, 2-mercaptoethyl, 1-mercaptopropyl, 2-mercaptopropyl, and 3-mercaptopropyl, of which mercaptomethyl, 1-mercaptoethyl and 2-mercaptoethyl are preferred.

In $R^1$ or $R^2$ a perfluoro($C_{1-4}$)alkyl group means a $C_{1-4}$ alkyl group in which all hydrogen atoms have been substituted by fluorine atoms. Examples include trifluoromethyl, pentafluoroethyl, heptafluoropropyl, and nonafluorobutyl, of which trifluoromethyl and pentafluoroethyl are preferred.

In a compound of formula I, an amino group may be optionally substituted by one or two $C_{1-4}$ alkyl groups. An amino group substituted by one or two $C_{1-4}$ alkyl groups means a group resulting from the substitution of one or two hydrogen atoms of the amino group by a $C_{1-4}$ alkyl group. When the amino group is substituted by two $C_{1-4}$ alkyl groups, they can be the same or different. Examples include amino, methylamino, dimethylamino, ethylamino, diethylamino, ethylmethylamino, propylamino, dipropylamino, isopropylamino, and diisopropylamino, of which methylamino, dimethylamino, ethylamino and diethylamino are preferred, and methylamino and dimethylamino are most preferred.

The term "halogen" means fluorine, chlorine, bromine or iodine.

In $R^1$ or $R^2$ a $C_{1-4}$ alkylsulphinyl group means a group derived from the union of a $C_{1-4}$ alkyl group to a sulphinyl group. Examples include methylsulphinyl, ethylsulphinyl, propylsulphinyl, isopropylsulphinyl, butylsulphinyl, isobutylsulphinyl, sec-butylsulphinyl and tert-butylsulphinyl, of which methylsulphinyl, ethylsulphinyl, propylsulphinyl, isopropylsulphinyl, butylsulphinyl and isobutylsulphinyl are preferred, and methylsulphinyl is most preferred.

The term "aryl" represents a phenyl group or a phenyl group substituted by a fluorine, chlorine, bromine or iodine atom, or a methyl, hydroxyl, methoxy, cyano or nitro group. Examples include phenyl, 2-methylphenyl, 4-methylphenyl, 4-chlorophenyl, 4-bromophenyl, 4-methoxyphenyl, 2-methoxyphenyl, and 4-cyanophenyl.

In $R^1$ or $R^2$ an arylsulphinyl group means a group derived from the union of an aryl group, like the above mentioned, to a sulphinyl group. Examples include phenylsulphinyl, 2-methylphenylsulphinyl, 4-methylphenylsulphinyl, 4-chlorophenylsulphinyl, 4-bromophenylsulphinyl, 4-methoxyphenylsulphinyl, 2-methoxyphenylsulphinyl, and 4-cyanophenylsulphinyl, of which phenylsulphinyl is preferred.

In $R^1$ or $R^2$ a $C_{1-4}$ alkylsulphonyl group means a group derived from the union of a $C_{1-4}$ alkyl group to a sulphonyl group. Examples include methylsulphonyl, ethylsulphonyl, propylsulphonyl, isopropylsulphonyl, butylsulphonyl, isobutylsulphonyl, sec-butylsulphonyl and tert-butylsulphonyl, of which methylsulphonyl, ethylsulphonyl, propylsulphonyl, isopropylsulphonyl, butylsulphonyl and isobutylsulphonyl are preferred, and methylsulphonyl is most preferred.

In $R^1$ or $R^2$ an arylsulphonyl group means a group derived from the union of an aryl group, like the above mentioned, to a sulphonyl group. Examples include phenylsulphonyl, 2-methylphenylsulphonyl, 4-methylphenylsulphonyl, 4-chlorophenylsulphonyl, 4-bromophenylsulphonyl, 4-methoxyphenylsulphonyl, 2-methoxyphenylsulphonyl, and 4-cyanophenylsulphonyl, of which phenylsulphonyl is preferred.

In $R^1$ or $R^2$ a $C_{1-4}$ alkoxysulphinyl group means a group derived from the union of a $C_{1-4}$ alkoxy group to a sulphinyl group. Examples include methoxysulphinyl, ethoxysulphinyl, propoxysulphinyl, isopropoxysulphinyl, butoxysulphinyl, isobutoxysulphinyl, sec-butoxysulphinyl and tert-butoxysulphinyl, of which methoxysulphinyl, ethoxysulphinyl, propoxysulphinyl, isopropoxysulphinyl, butoxysulphinyl and isobutoxysulphinyl are preferred, and methoxysulphinyl is most preferred.

In $R^1$ or $R^2$ a $C_{1-4}$ alkoxysulphonyl group means a group derived from the union of a $C_{1-4}$ alkoxy group to a sulphonyl group. Examples include methoxysulphonyl, ethoxysulphonyl, propoxysulphonyl, isopropoxysulphonyl, butoxysulphonyl, isobutoxysulphonyl, sec-butoxysulphonyl and tert-butoxysulphonyl, of which methoxysulphonyl, ethoxysulphonyl, propoxysulphonyl, isopropoxysulphonyl, butoxysulphonyl and isobutoxysulphonyl are preferred, and methoxysulphonyl is most preferred.

In $R^1$ or $R^2$ a $C_{1-4}$ alkylcarbonylamino group means a group derived from the substitution of an hydrogen atom of an amino group, like the above mentioned, by a $C_{1-4}$ alkylcarbonyl group. Examples include acetamido, N-methylacetamido, propanamido, N-methylpropanamido, and isopropanamido, of which acetamido, N-methylacetamido, propanamido and N-methylpropanamido are preferred, and acetamido and N-methylacetamido are most preferred.

In $R^1$ or $R^2$ a $C_{1-4}$ alkoxycarbonylamino group means a group derived from the substitution of an hydrogen atom of an amino group, like the above mentioned, by a $C_{1-4}$ alkoxycarbonyl group. Examples include methoxycarbonylamino, ethoxycarbonylamino, propoxycarbonylamino, isopropoxycarbonylamino, butoxycarbonylamino, and isobutoxycarbonylamino, of which methoxycarbonylamino and ethoxycarbonylamino are preferred, and methoxycarbonylamino is most preferred.

In $R^1$ or $R^2$ an aminosulphinyl group means a group derived from the union of an amino group, like the above mentioned, to a sulphinyl group, and includes, among others, aminosulphinyl, methylaminosulphinyl, dimethylaminosulphinyl, ethylaminosulphinyl, diethylaminosulphinyl, ethylmethylaminosulphinyl, propylaminosulphinyl, dipropylaminosulphinyl, isopropylaminosulphinyl, and diisopropylaminosulphinyl, of which aminosulphinyl, methylaminosulphinyl, dimethylaminosulphinyl, ethylaminosulphinyl, and diethylaminosulphinyl are preferred, and aminosulphinyl, methylaminosulphinyl and dimethylaminosulphinyl are most preferred.

In $R^1$ or $R^2$ an aminosulphonyl group means a group derived from the union of an amino group, like the above mentioned, to a sulphonyl group, and includes, among others, aminosulphonyl, methylaminosulphonyl, dimethylaminosulphonyl, ethylaminosulphonyl, diethylaminosulphonyl, ethylmethylaminosulphonyl, propylaminosulphonyl, dipropylaminosulphonyl, isopropylaminosulphonyl, and diisopropylaminosulphonyl, of which aminosulphonyl, methylaminosulphonyl, dimethylaminosulphonyl, ethylaminosulphonyl, and diethylaminosulphonyl are preferred, and aminosulphonyl, methylaminosulphonyl and dimethylaminosulphonyl are most preferred.

In $R^1$ or $R^2$ an aminocarbonyl group means a group derived from the union of an amino group, like the above mentioned, to a carbonyl group. Examples include aminocarbonyl, methylaminocarbonyl, dimethylaminocarbonyl, ethylaminocarbonyl, diethylaminocarbonyl, ethylmethylaminocarbonyl, propylaminocarbonyl, dipropylaminocarbonyl, isopropylaminocarbonyl, and diisopropylaminocarbonyl, of which aminocarbonyl, methylaminocarbonyl, dimethylaminocarbonyl, ethylaminocarbonyl and diethylaminocarbonyl are preferred, and aminocarbonyl, methylaminocarbonyl and dimethylaminocarbonyl are most preferred.

In $R^1$ or $R^2$ an aminothiocarbonyl group means a group derived from the union of an amino group, like the above mentioned, to a thiocarbonyl group. Examples include aminothiocarbonyl, methylaminothiocarbonyl, dimethylaminothiocarbonyl, ethylaminothiocarbonyl, diethylaminothiocarbonyl, ethylmethylaminothiocarbonyl, propylaminothiocarbonyl, dipropylaminothiocarbonyl, isopropylaminothiocarbonyl, and diisopropylaminothiocarbonyl, of which aminothiocarbonyl, methylaminothiocarbonyl, dimethylaminothiocarbonyl, ethylaminothiocarbonyl and diethylaminothiocarbonyl are preferred, and aminothiocarbonyl, methylaminothiocarbonyl and dimethylaminothiocarbonyl are most preferred.

In $R^1$ or $R^2$ a $C_{1-4}$ alkylsulphinylamino group means a group resulting from the substitution of an hydrogen atom of an amino group, like the above mentioned, by a $C_{1-4}$ alkylsulphinyl group. Examples include methylsulphinylamino, ethylsulphinylamino, propylsulphinylamino, isopropylsulphinylamino, butylsulphinylamino, isobutylsulphinylamino, sec-butylsulphinylamino and tert-butylsulphinylamino, of which methylsulphinylamino and ethylsulphinylamino are preferred, and methylsulphinylamino is most preferred.

In $R^1$ or $R^2$ a $C_{1-4}$ alkylsulphonylamino group means a group resulting from the substitution of an hydrogen atom of an amino group, like the above mentioned, by a $C_{1-4}$ alkylsulphonyl group. Examples include methylsulphonylamino, ethylsulphonylamino, propylsulphonylamino, isopropylsulphonylamino, butylsulphonylamino, isobutylsulphonylamino, sec-butylsulphonylamino and tert-butylsulphonylamino, of which methylsulphonylamino and ethylsulphonylamino are preferred, and methylsulphonylamino is most preferred.

In $R^1$ or $R^2$ a $C_{1-4}$ alkoxysulphinylamino group means a group resulting from the substitution of an hydrogen atom of an amino group, like the above mentioned, by a $C_{1-4}$ alkoxysulphinyl group. Examples include methoxysulphinylamino, ethoxysulphinylamino, propoxysulphinylamino, isopropoxysulphinylamino, butoxysulphinylamino, isobutoxysulphinylamino, sec-butoxysulphinylamino and tert-butoxysulphinylamino, of which methoxysulphinylamino and ethoxysulphinylamino are preferred, and methoxysulphinylamino is most preferred.

In $R^1$ or $R^2$ a $C_{1-4}$ alkoxysulphonylamino group means a group resulting from the substitution of an hydrogen atom of an amino group, like the above mentioned, by a $C_{1-4}$ alkoxysulphonyl group. Examples include methoxysulphonylamino, ethoxysulphonylamino, propoxysulphonylamino, isopropoxysulphonylamino, butoxysulphonylamino, isobutoxysulphonylamino, sec-butoxysulphonylamino and tert-butoxysulphonylamino, of which methoxysulphonylamino and ethoxysulphonylamino are preferred, and methoxysulphonylamino is most preferred.

In $R^1$ or $R^2$ a ($C_{1-4}$ alkyl)carbonyl($C_{1-4}$ alkyl) group means a group derived from the union of a ($C_{1-4}$ alkyl)carbonyl group, like the above mentioned, to a $C_{1-4}$ alkyl group. Preferred examples are 2-oxopropyl, 2-oxobutyl, 3-oxobutyl and 3-oxopentyl.

In $R^1$ or $R^2$ a nitro-($C_{1-4}$ alkyl) group means a group resulting from the substitution of an hydrogen atom of a $C_{1-4}$ alkyl group by a nitro group. Examples include nitromethyl, 1-nitroethyl, 2-nitroethyl, 1-nitropropyl, 2-nitropropyl, and 3-nitropropyl, of which nitromethyl, 1-nitroethyl and 2-nitroethyl are preferred.

In $R^1$ or $R^2$ a cyano-($C_{1-4}$ alkyl) group means a group resulting from the substitution of an hydrogen atom of a $C_{1-4}$ alkyl group by a cyano group. Examples include cyanomethyl, 1-cyanoethyl, 2-cyanoethyl, 1-cyanopropyl, 2-cyanopropyl, and 3-cyanopropyl, of which cyanomethyl, 1-cyanoethyl and 2-cyanoethyl are preferred.

Examples of (C$_{1-4}$ alkyl)C(=NOH) include 1-oximinoethyl, 1-oximinopropyl, 1-oximinobutyl, 2-methyl-1-oximinopropyl, and 1-oximinopentyl, of which 1-oximinoethyl and 1-oximinopropyl are preferred, and 1-oximinoethyl is most preferred.

Examples of (C$_{1-4}$ alkyl)C(=NNH$_2$) include 1-hidrazonoethyl, 1-hidrazonopropyl, 1-hidrazonobutyl, 2-methyl-1-hidrazonopropyl, and 1-hidrazonopentyl, of which 1-hidrazonoethyl and 1-hidrazonopropyl are preferred, and 1-hidrazonoethyl is most preferred.

Examples of (C$_{1-4}$ alkoxy)C(=NH) include methyl imidate, ethyl imidate, propyl imidate, isopropyl imidate, and butyl imidate, of which methyl imidate and ethyl imidate are preferred, and methyl imidate is most preferred.

In a compound of formula I, R$^3$ and R$^4$ are preferred to be both C$_{1-4}$ alkyl, more preferably methyl or ethyl, and most preferably methyl.

In a compound of formula I, R$^8$ is preferred to be an unsubstituted radical, and is preferred to contain a carbonyl group rather than a thiocarbonyl group. In case R$^8$ is a radical substituted by a R$^9$ group, the substituent can be in the 3-, 4-, 5- or 6-position of the ring, preferably in the 3- or 5-position. In case R$^8$ is a radical substituted by a R$^{10}$ group, the substituent is preferred to be in the 3-, 4-, or 5-position of the ring, and more preferably in the 5-position.

Examples of R$^8$ radicals optionally substituted by an R$^9$ group include: 1,2-dihydro-2-oxo-1-pyridyl, 3-, 4-, 5- or 6-hydroxy, 3-, 4-, 5- or 6-chloro, 3- or 5-nitro, 3- or 5-amino-1,2-dihydro-2-oxo-1-pyridyl, 1,2-dihydro-2-oxo-1-pyrazinyl, 3-hydroxy-1,2-dihydro-2-oxo-1-pyrazinyl, 1,2-dihydro-6-oxo-1-pyridazinyl, 5-hydroxy-1,2-dihydro-6-oxo-1-pyridazinyl, 1,2-dihydro-2-oxo-1-pyrimidinyl, 1,2-dihydro-6-oxo-1-pyrimidinyl, 1,2-dihydro-2-thioxo-1-pyridyl, 2,3-dihydro-1-oxo-1H-isoindol-2-yl, 1-oxo-1,2,3,4-tetrahydroisoquinol-2-yl, of which 1,2-dihydro-2-oxo-1-pyridyl, 3- or 5-nitro-1,2-dihydro-2-oxo-1-pyridyl, 1,2-dihydro-2-oxo-1-pyrazinyl, 1,2-dihydro-6-oxo-1-pyridazinyl, 1,2-dihydro-2-oxo-1-pyrimidinyl, 1,2-dihydro-6-oxo-1-pyrimidinyl, 2,3-dihydro-1-oxo-1H-isoindol-2-yl and 1-oxo-1,2,3,4-tetrahydroisoquinol-2-yl are preferred, and 1,2-dihydro-2-oxo-1-pyridyl is most preferred.

Examples of R$^8$ radicals optionally substituted by an R$^{10}$ group include: 2-oxo-1-pyrrolidinyl, 5-methyl-2-oxo-1-pyrrolidinyl, 5-hydroxymethyl-2-oxo-1-pyrrolidinyl, 5-methoxymethyl-2-oxo-1-pyrrolidinyl, 5-methylthiomethyl-2-oxo-1-pyrrolidinyl, 5-dimethylaminomethyl-2-oxo-1-pyrrolidinyl, 3-hydroxy-2-oxo-1-pyrrolidinyl, 4-hydroxy-2-oxo-1-pyrrolidinyl, 2-oxo-1-piperidinyl, 5-methyl-2-oxo-1-piperidinyl, 5-hydroxymethyl-2-oxo-1-piperidinyl, 5-methoxymethyl-2-oxo-1-piperidinyl, 5-methylthiomethyl-2-oxo-1-piperidinyl, 5-dimethylaminomethyl-2-oxo-1-piperidinyl, 3-hydroxy-2-oxo-1-piperidinyl, 4-hydroxy-2-oxo-1-piperidinyl, 2-thioxo-1-pyrrolidinyl, 2-thioxo-1-piperidinyl, of which 2-oxo-1-pyrrolidinyl and 2-oxo-1-piperidinyl are most preferred, and 2-oxo-1-pyrrolidinyl is most preferred.

In R$^9$ and R$^{10}$, the definitions of the different meanings for each substituent are those as mentioned above in connection with R$^1$ and R$^2$.

Preferred embodiments of the present invention are those compounds of formula Ia

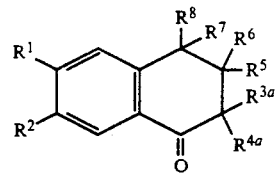

wherein R$^1$, R$^2$, R$^5$, R$^6$, R$^7$ and R$^8$ have the previously defined meaning; and R$^{3a}$ and R$^{4a}$ are methyl or ethyl.

More preferred embodiments of the present invention are those compounds of formula Ib

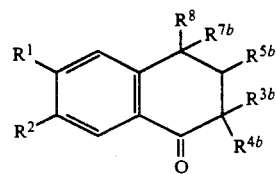

wherein R$^1$, R$^2$ and R$^8$ have the previously defined meaning; R$^{3b}$ and R$^{4b}$ mean R$^{3a}$ and R$^{4a}$ respectively; and, either R$^{5b}$ represents hydroxyl and R$^{7b}$ an hydrogen atom, or R$^{5b}$ and R$^{7b}$ together form a bond.

Still more preferred embodiments of the present invention are those compounds of formula Ic

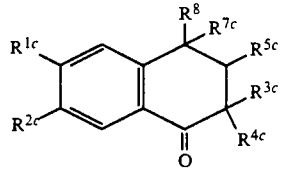

wherein R$^8$ has the previously defined meaning; R$^{3c}$, R$^{4c}$, R$^{5c}$ and R$^{7c}$ mean R$^{3a}$, R$^{4a}$, R$^{5b}$ and R$^{7b}$ respectively; R$^{1c}$ means halogen, cyano, C$_{1-4}$ alkyl, arylsulphonyl, trifluoromethyl, pentafluoroethyl, ethynyl, trimethylsilylethynyl or C$_{1-4}$ alkylcarbonylamino optionally substituted by a C$_{1-4}$ alkyl group; and R$^{2c}$ means hydrogen or R$^{1c}$.

Particularly preferred embodiments of the present invention are those compounds of formula Id

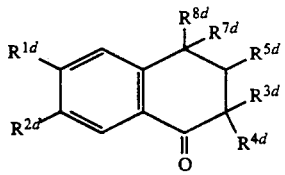

wherein R$^{1d}$, R$^{2d}$, R$^{3d}$, R$^{4d}$, R$^{5d}$ and R$^{7d}$ mean R$^{1c}$, R$^{2c}$, R$^{3a}$, R$^{4a}$, R$^{5b}$ and R$^{7b}$ respectively; and R$^{8d}$ means 2-oxo-1-pyrrolidinyl or 1,2-dihydro-2-oxo-1-pyridinyl.

More particularly preferred embodiments of the present invention are those compounds of formula Ie.

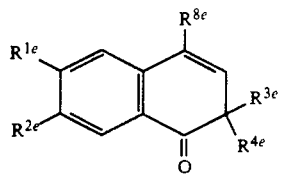

Ie wherein $R^{1e}$, $R^{2e}$, $R^{3e}$, $R^{4e}$ and $R^{8e}$ mean $R^{1c}$, $R^{2c}$, $R^{3a}$, $R^{4a}$ and $R^{8d}$ respectively.

Most preferred embodiments of the present invention are those compounds of formula If

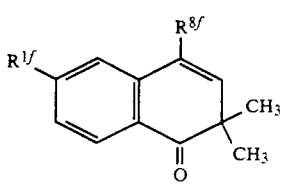

If wherein $R^{1f}$ means $R^{1c}$; and $R^{8f}$ means 1,2-dihydro-2-oxo-1-pyridinyl.

The formulae of some specific examples are represented below, together with the number corresponding to the example in which their preparation is described:

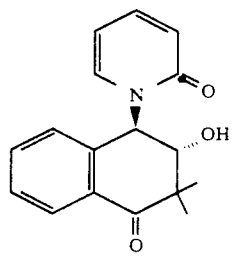

1

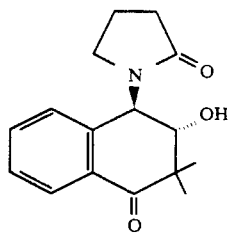

2

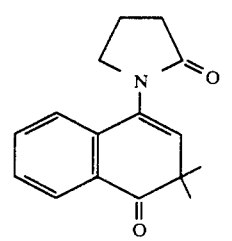

3

-continued

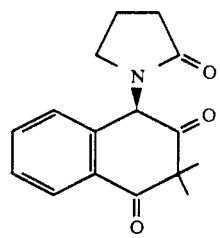

4

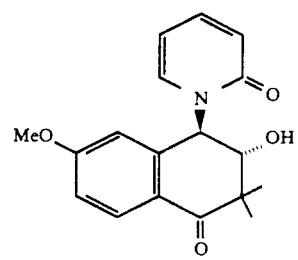

5

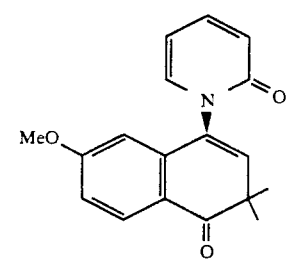

6

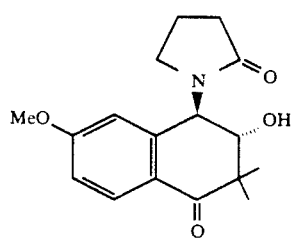

7

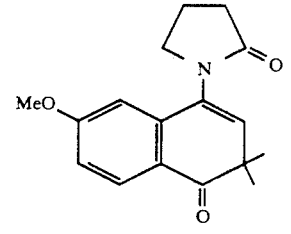

8

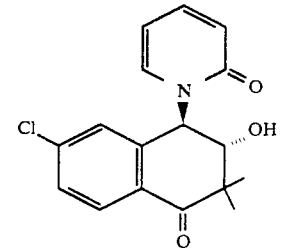

9

13
-continued
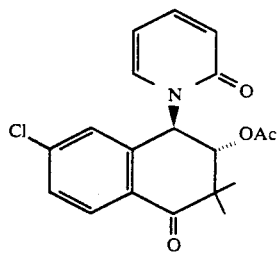
10
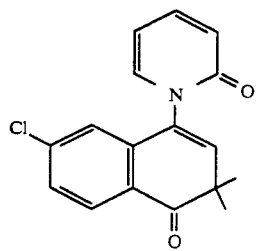
11
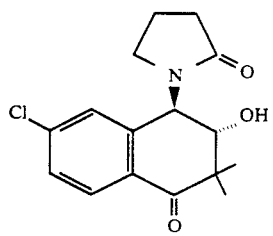
12
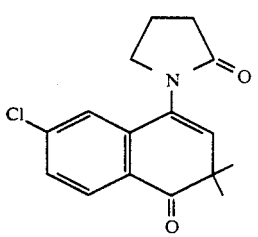
13
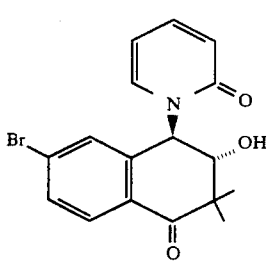
14
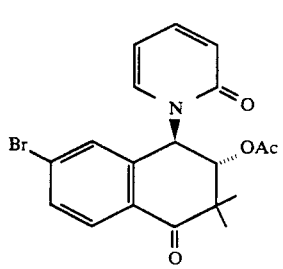
15
14
-continued
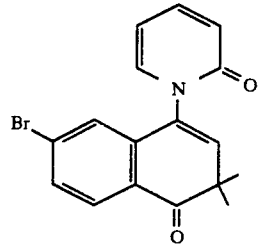
16
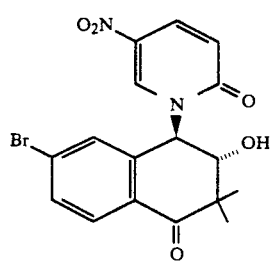
17
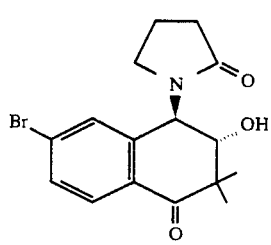
18
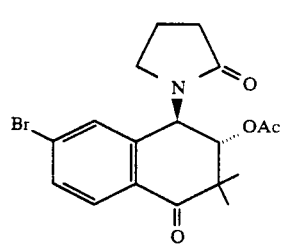
19
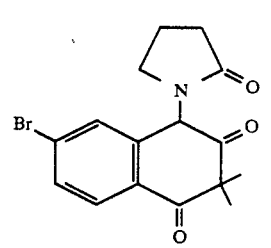
20
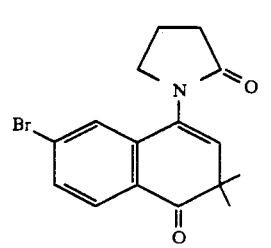
21

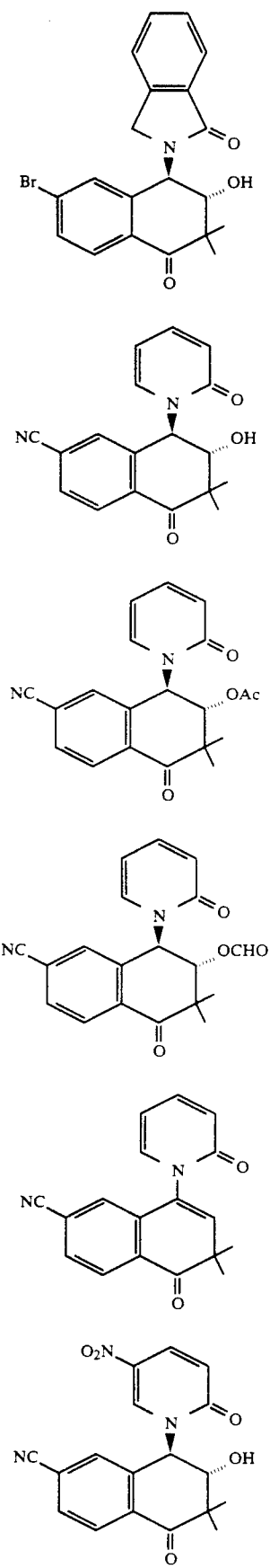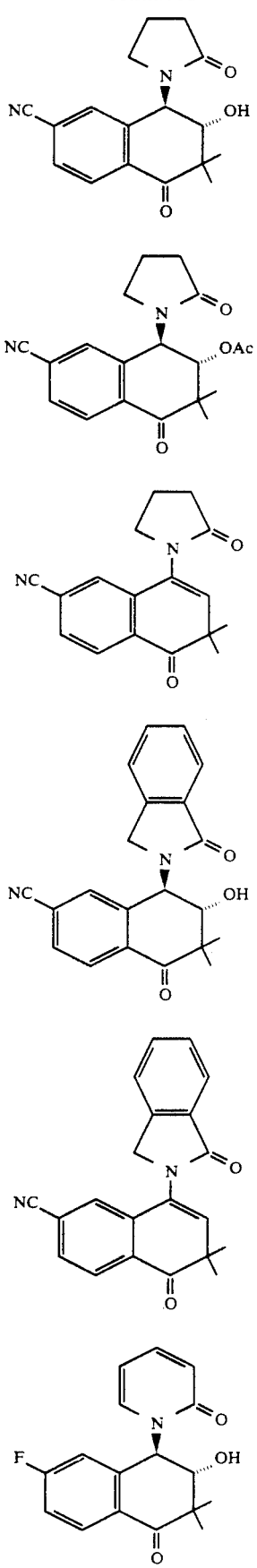

34
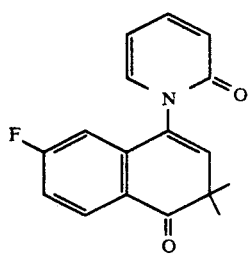
35
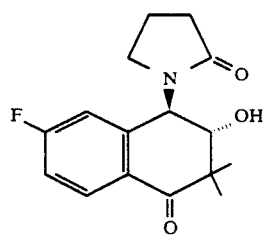
36
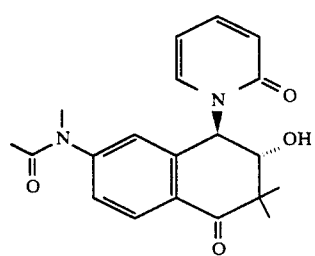
37
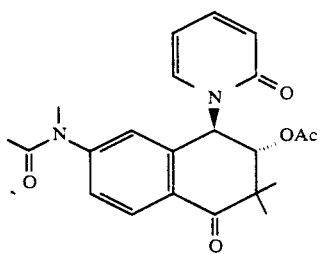
38
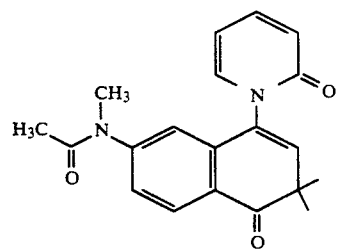
39
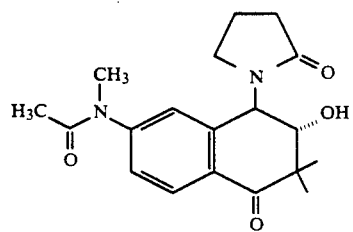
40
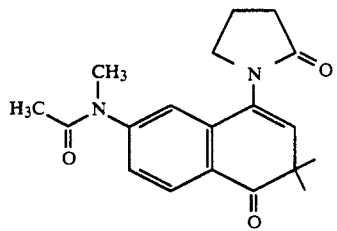
41
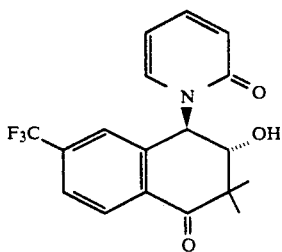
42
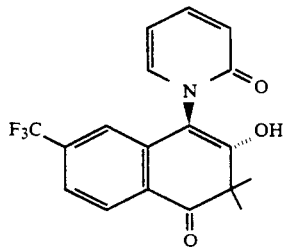
43
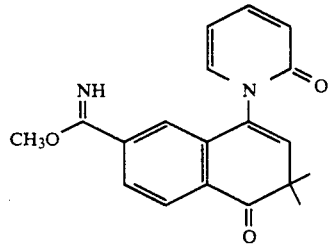
44
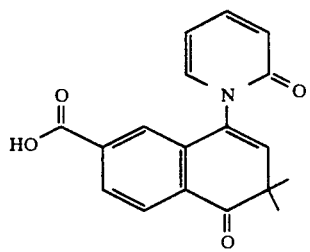
45
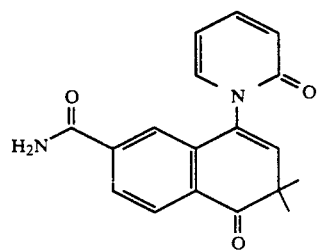

19
-continued
46
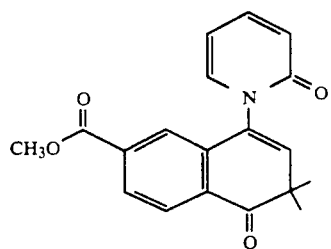
47
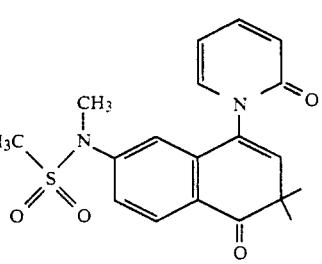
48
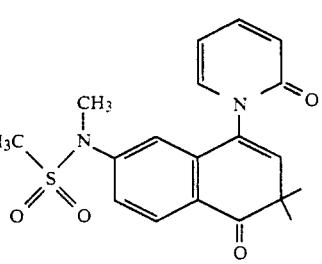
49
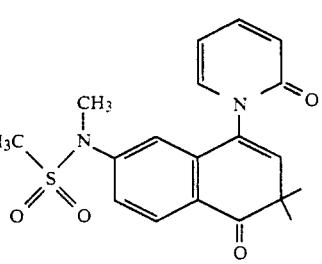
50
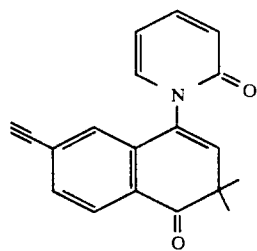
51
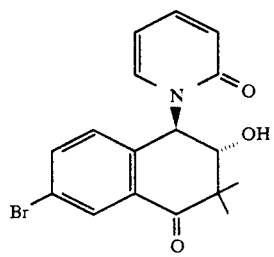
20
-continued
52
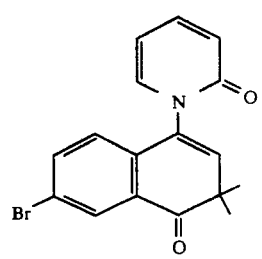
53
54
55
56
57

-continued

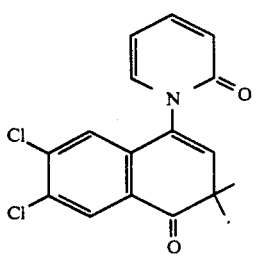
58

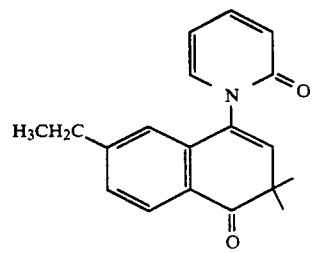
59

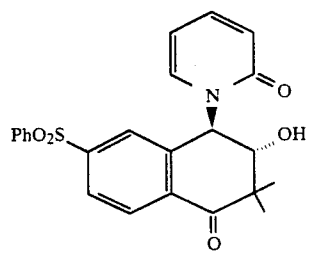
61

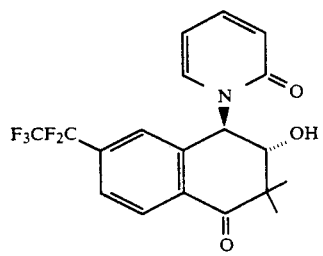
62

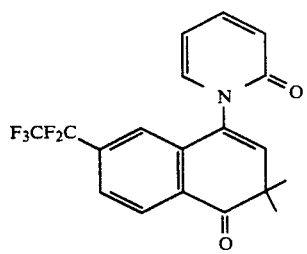
63

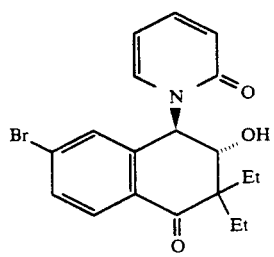

-continued

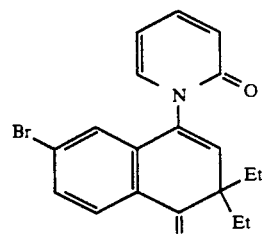
64

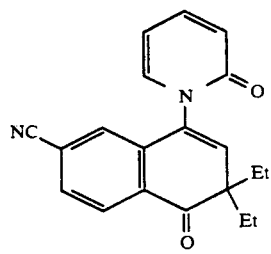
65

Some of the compounds of the present invention contain one or more basic nitrogen atoms and, consequently, they can form salts, which are also included in the present invention. There is no limitation on the nature of these salts but pharmaceutically acceptable ones are preferred. Examples of these salts include: salts with an inorganic acid such as hydrochloric acid, hydrobromic acid, hydriodic acid, nitric acid, perchloric acid, sulfuric acid or phosphoric acid; and salts with an organic acid, such as methanesulphonic acid, trifluoromethanesulphonic acid, ethanesulphonic acid, benzenesulphonic acid, p-toluenesulphonic acid, fumaric acid, oxalic acid or maleic acid.

The compounds of the present invention can exist as different diastereoisomers and/or optical isomers because the carbons in positions 3 and 4 of the aromatic ring, provided that there is not a double bond between them, are chiral and in some cases there is an additional chiral center. Diastereoisomers can be separated by conventional techniques such as chromatography or fractional crystallization. The optical isomers can be resolved using any of the conventional techniques of optical resolution to give optically pure isomers. Such a resolution can be performed in any chiral synthetic intermediate as well as in the products of general formula I. The optically pure isomers can also be individually obtained using enantiospecific synthesis. The present invention covers the individual isomers as well as their mixtures (e.g. racemic mixtures), being irrelevant if they have been obtained by synthesis or have been prepared physically mixing them up.

The invention also provides processes for preparing the compounds of formula I. The precise method used for the preparation of a given compound of the present invention may vary depending on its chemical structure. Scheme 1 illustrates the general method for their preparation.

SCHEME 1

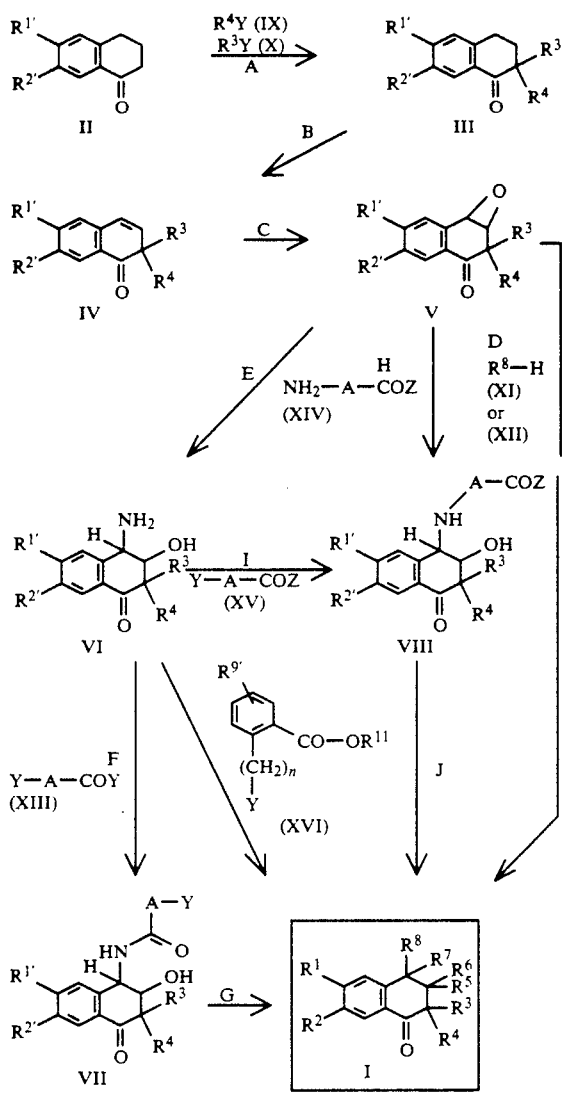

Wherein:

$R^1$, $R^2$, $R^{1'}$, $R^{2'}$, $R^3$, $R^4$, $R^5$, $R^6$, $R^7$ and $R^8$ have the previously defined meaning;

Y is a good leaving group, such as a chlorine, bromine or iodine atom;

Z means a group that can be replaced by a secondary amine, such as hydroxide and particularly $C_{1-4}$ alkoxy, like ethoxy o methoxy;

A means a trimethylene or a tetramethylene group optionally substituted by an $R^{10}$ group;

n means 1 or 2;

$R^{9'}$ means either hydrogen or $R^9$ as previously defined; and $R^{11}$ is a $C_{1-4}$ alkyl group.

The preparation of the compounds of general formula I starts from the tetralones of general formula II, which either are known compounds (see, for instance, N. L. Allinger, E. S. Jones, *J. Org. Chem.*, 1962, 27, 70), or, if they have not been described, can be prepared following analogous methods to those described in the literature.

The reaction of tetralones II (Step A) with an equivalent of base, such as sodium hydride or butyl lithium, and an alkylating agent of general formula $R^4$—Y (IX), in an inert solvent, such as benzene or tetrahydrofuran, at a temperature between room temperature and that of the boiling point of the solvent and during a period of time from 6 to 48 h, leads to the compounds of general formula III wherein $R^3$ is hydrogen and $R^4$ is $C_{1-4}$ alkyl. The subsequent alkylation with one more equivalent of base and an alkylating agent of general formula $R^3$—Y (X) leads to the compounds of general formula III wherein $R^3$ and $R^4$ are $C_{1-4}$ alkyl groups. When $R^3$ and $R^4$ are the same, dialkylation can be performed directly, by using two equivalents of base and an excess of alkylating agent in the same experimental conditions described above. In case $R^3$ and $R^4$ together form a $C_{2-5}$ polymethylene chain, the compounds of formula III are obtained by alkylation with 2 equivalents of base and an alkylating agent of formula Y—$(CH_2)_p$—Y, wherein Y has the previously defined meaning and p is 2, 3, 4 or 5.

The reaction of compounds of general formula III (Step B) with a brominating agent, such as N-bromosuccinimide or $Br_2$, in an inert solvent, such as carbon tetrachloride, at a temperature between room temperature and that of the boiling point of the solvent and during a reaction time from 4 to 24 h, followed by treatment with a base, such as potassium hydroxide, in an alcoholic solvent, such ethanol, at a temperature between room temperature and that of the boiling point of the solvent and during a reaction time from 0.5 to 2 h, leads to the compounds of general formula IV. This process is described in the literature when $R^1=R^2=H$ and $R^3=R^4=Me$ (L. H. Klemm, J. Shabtai, D. R. Taylor, *J. Org. Chem.*, 1968, 33, 1480).

In step C, a compound of general formula IV is allowed to react with a peracid, such as m-chloroperbenzoic acid, in a suitable solvent, such as methylene chloride, at a reaction temperature from 0° C. to room temperature and during a reaction time from 6 to 24 h, to give an epoxide of general formula V. Alternatively, this epoxide may be obtained by hydrobromination of the double bond of the compounds of general formula IV with N-bromosuccinimide in a suitable solvent, such as dimethylsulphoxide or water, at a temperature from room temperature to the boiling point of the solvent and during a reaction time from 2 to 24 h, followed by treatment with a base, such as sodium hydroxide, in a suitable solvent, such as dioxane or water, at a temperature from room temperature to that of the boiling point of the solvent and during a reaction time from 2 to 24 h.

The reaction of the compounds of general formula V (Step D) with an amide of general formula $R^8$—H (XI), wherein $R^8$ has the previously defined meaning, in the presence of a base, such as sodium hydride, in a suitable solvent, such as dimethylsulphoxide or dimethylformamide, or in the presence of pyridine in a suitable solvent, such as ethanol, at a temperature from room temperature to that of the boiling point of the solvent and during a reaction time from 6 to 72 h, leads to the compounds of general formula I wherein $R^5$ is OH and $R^6$ and $R^7$ are hydrogen. Alternatively, when $R^8$ is 1H-2-Pyridon-1-yl these compounds may be obtained by reacting a compound of formula V with trimethylsilyloxypyridine (XII) in a suitable solvent, such as tetrahydrofuran, in the presence of tetrabutylammonium fluoride, at a temperature between 0° C. and that of the boiling point of the solvent and during a period of time from 1 to 7 days. The nucleophilic attack occurs in the position 4 of epoxide V, leading to products with the right regiochemistry and trans configuration, as proved by $H^1$-NMR spectra analysis.

Alternatively, compounds of general formula I, wherein $R^5$ is OH, $R^6$ and $R^7$ are hydrogen, and $R^8$ is 2-oxo-1-pyrrolidinyl or 2-oxo-1-pyperidinyl optionally substituted by an $R^{10}$ group, may also be obtained by the following sequence: reaction of a compound of formula V with ammonia (Step E) in a suitable solvent, such as ethanol or a mixture of ethanol and water, at a temperature from $-50°$ C. to that of the boiling point of the solvent and during a reaction time that ranges from 1 to 7 days, to give a compound of general formula VI; reaction of compound VI (Step F) with a compound of general formula Y—A—COY (XIII), wherein A and Y have the previously defined meaning, in the presence of a base, such as sodium hydroxide, in a suitable solvent, such as chloroform, methylene chloride or chloroform-water mixtures, at a temperature between room temperature and that of the boiling point of the solvent and during a reaction time from 1 to 24 hours, to give a compound of general formula VII; and finally, cyclization of VII (Step G) in the presence of a base, such as potassium carbonate, in a suitable solvent, such as acetone, at the temperature of the boiling point of the solvent and during a reaction time from 3 to 48 hours.

Another alternative sequence for the preparation of these compounds is the cyclization of a compound of general formula VIII (Step J) under reflux of an inert solvent, such as toluene or xylene, and during a reaction time from 3 to 24 h. Compounds of general formula VIII may be obtained by treatment of a compound of general formula V (Step H) with a compound of general formula $NH_2$—A—CO—Z (XIV), wherein A and Z have the previously defined meaning, in an alcoholic solvent, such as ethanol, at a temperature between room temperature and that of the boiling point of the solvent and during a reaction time from 4 to 24 h, or by treatment of a compound of general formula VI (Step I) with a compound of general formula Y—A—COZ (XV), wherein Y, A, and Z have the previously defined meaning, in the presence of a proton scavenger base, such as triethylamine, in a suitable solvent, such as chloroform or dimethylformamide, at a temperature between room temperature and that of the boiling point of the solvent and during a reaction time from 4 to 24 h.

Compounds of formula I, wherein $R^5$ is OH, $R^6$ and $R^7$ are H, and $R^8$ is 2,3-dihydro-1-oxo-1H-isoindol-2-yl or 1-oxo-1,2,3,4-tetrahydroisoquinol-2-yl optionally substituted by an $R^9$ group, may also be obtained by treatment of a compound of formula VI with a compound of formula XVI, wherein Y, n, $R^{9'}$ and $R^{11}$ have the previously defined meaning, in the presence of an excess of a base such as potassium carbonate and a small amount of potassium iodide in a suitable solvent, such as acetonitrile, at the temperature of the boiling point of the solvent and during a reaction time from 4 to 48 h.

Compounds of general formula I which carry a thiocarbonyl group on the radical $R^8$ can be obtained by thiation of the corresponding oxygen derivatives with conventional reagents such as hydrogen sulphide, phosphorous pentasulphide or Lawesson's reagent (p-methoxyphenylthiophosphine disulphide) in an apolar inert solvent, such as toluene, at the temperature of the boiling point of the solvent and during a reaction time from 1 to 24 h.

Compounds of general formula I wherein $R^5$ is acetoxy and $R^6$ and $R^7$ are hydrogen can be obtained by acetylation of the corresponding hydroxy derivatives with acetic anhydride in the presence of a base, such as pyridine, at room temperature and during a reaction time from 24 to 96 hours.

Compounds of general formula I wherein $R^5$ is formyloxy and $R^6$ and $R^7$ are hydrogen can be obtained by reaction of the corresponding hydroxy derivatives with formic acid in the presence of a base, such as pyridine, and in similar experimental conditions to those mentioned above for the acetylation.

Compounds of general formula I wherein $R^5$ and $R^7$ together form a bond may be obtained in some cases directly through the reaction of amides of general formula XI with epoxides of general formula V due to a simultaneous elimination of water. Alternatively, these compounds can be obtained from the corresponding hydroxy derivatives using conventional reactions of dehydration such as treatment with sodium hydride or sodium hydroxide in an inert solvent, such as tetrahydrofuran or dioxane, at a temperature between room temperature and that of the boiling point of the solvent and during a reaction time from 6 to 48 h, or by treatment of the corresponding acetoxy derivatives with a dehydrating agent, such as 1,8-diazabicyclo(5.4.0)undec-7-ene, in an inert solvent, such as toluene, at a temperature between room temperature and that of the boiling point of the solvent and during a reaction time from 6 to 48 h. They may also be obtained by treatment of the corresponding hydroxy derivatives with a salt of a weak acid, such as sodium acetate, in a polar solvent of high boiling point, such as N-methylpyrrolidone, at a temperature between room temperature and that of the boiling point of the solvent, and during a period of time from 2 to 48 h; optionally, when in the hydroxy derivative $R^1$ or $R^2$ are a bromine atom, it is possible to transform said bromine atom into a cyano group by using an excess of cuprous cyanide in a polar solvent of high boiling point, such as N-methylpyrrolidone, at a temperature between room temperature and that of the boiling point of the solvent, and during a period of time from 2 to 48 h, a process that leads to the simultaneous elimination of water, forming a double bond between positions 3 and 4 of the tetralone ring.

Furthermore, it is also possible to transform the groups $R^1$ and/or $R^2$ in a compound of formula I or $R^{1'}$ and/or $R^{2'}$ in one of its synthetic intermediates into other groups $R^1$ and/or $R^2$.

For instance, a cyano group may be transformed into a carboxyl group (e.g. with HCl in water, at $20°-100°$ C.), into a carbamoyl group (e.g. with KOH in t-BuOH), into a methyl carboximidate group (e.g. with sodium methoxide in MeOH, at room temperature), or into a methyl carboxylate (e.g. with HCl gas in MeOH, at reflux); a bromine atom may be converted into a trifluoromethyl or a pentafluoroethyl group (e.g. with trifluoroacetate or pentafluoropropionate resp./cuprous iodide in N-methylpyrrolidone, at $160°$ C.), or into a trimethylsilylethynyl group (e.g. with Pd(II) acetate/ethynyltrimethylsilane/triphenylphosphine in $NEt_3$), which may be subsequently transformed into an ethynyl group (e.g. with potassium carbonate in MeOH, at room temperature); a methoxy group may be transformed into a hydroxyl group (e.g. with 48% HBr, at reflux), and this may be then converted into a bromine atom (e.g. with triphenylphosphonium bromide, at $185°$ C.); an acetamido group may be alkylated to an N-methylacetamido group (e.g. MeI/NaH in bencene, at $50°$ C. and then at reflux), which may be deacetylated to a methylamino group (e.g. with HCl, at reflux), and this transformed into a N-methylmethanesulphonamide (e.g. with methanesulphonyl chloride in $CHCl_3$/pyridine, at 0° C.-room temperature).

The compounds of formula I may be transformed into their corresponding acid addition salts by treatment with an acid, such as hydrochloric acid, sulphuric acid, nitric acid, oxalic acid or methanesulphonic acid.

The intermediates V-VIII are new and form also part of the present invention.

The compounds of general formula I are useful as antihypertensive agents, as shown by their ability to inhibit the contraction induced by noradrenaline in portal vein isolated from rat, according to test 1, and their ability to lower the blood pressure in hypertense rats, according to test 2.

Test 1: Inhibition of the contraction induced by noradrenaline in portal vein isolated from rat.

Portal vein was extracted from adult male rats (between 200 and 250 g of body weight), which had been stunned by a blow in the head. Portal vein was installed into an isolated organ bath (Letica) containing a physiological saline solution (Hamilton et al., Br. J. Pharmacol., 1986, 88, 103-111) at 37° C. and a gas bubbler (5% $CO_2$ and 95% $O_2$). Contractions were induced by noradrenaline (3 $\mu M$) and were reverted after thoroughly washing with physiological saline solution. Portal vein contraction was measured with an isometric force transducer and with an initial tension of 1 g. After two contractions with noradrenaline, performed in order to measure the tissue's basal response, the tested compounds were incubated for 30 minutes and a new contraction was induced. The concentration that produces a 50% inhibition ($IC_{50}$) versus the basal response was calculated. The results are shown in table I.

TABLE I

| Compound No | $IC_{50}(\mu M)$ |
| --- | --- |
| 6 | 21 |
| 11 | 1.4 |
| 13 | >10 |
| 14 | 28 |
| 16 | 0.5 |
| 18 | >10 |
| 21 | 10 |
| 22 | 3.1 |
| 23 | 14 |
| 24 | 23 |
| 26 | 0.6 |
| 30 | 0.8 |
| 36 | 33 |
| 38 | 4.3 |
| 40 | 17 |
| 41 | 1.9 |
| 42 | 0.35 |
| 49 | 0.46 |
| 50 | 0.98 |
| 52 | 2.7 |
| 55 | >10 |
| 57 | 1.5 |
| 58 | 0.7 |
| 60 | 0.3 |

Test 2: Lowering of the arterial pressure in concious hypertense rats.

Spontaneously hypertense rats (between 200 and 250 g of body weight) of more than 8 weeks of age have been used. Diastolic and systolic arterial pressure of the rat was measured at the caudal artery using a special sphygnomanometer (Letica 5007 and 5007/4) attached to the animal's tail. To ensure rapid and reliable data, animals were placed in a heating plate at 37° C., with the aim to produce a vasodilatation that ensured a better fixation of the rat tail to the transducer chamber. During the experiment, rats are conscious and fixed to a clamp. The tested products were administered orally. Arterial pressure was measured every 60 minutes during 4 hours and 10 minutes before the administration of the tested compound. The decrease of the arterial pressure was calculated for each compound at a dose of 1 mg/Kg, using 3 animals. The results are shown in table II.

TABLE II

| Compound No | Pressure Decrease (mm Hg) (1mg/Kg p.o.) |
| --- | --- |
| 6 | 42.5 |
| 11 | 53 |
| 13 | 32 |
| 14 | 23 |
| 18 | 39 |
| 21 | 60.5 |
| 22 | 24 |
| 23 | 84 |
| 24 | 64.7 |
| 26 | 96.5 |
| 30 | 103 |
| 36 | 94 |
| 38 | 49.3 |
| 40 | 23 |
| 41 | 52.6 |
| 42 | 103 |
| 49 | 91.5 |
| 50 | 112 |
| 52 | 37 |
| 55 | 41 |
| 57 | 52 |
| 58 | 58 |
| 60 | 32.5 |

Furthermore, we have found that compounds of general formula I are bronchodilator agents, according to test 3.

Test 3—Direct relaxation of the trachea isolated from guinea pig.

This test was performed according to the experimental model described by Emmerson, J. and Mackay, D. (J. Pharm. Pharmacol., 1979, 31, 798). Tracheas were extracted from male guinea pigs of 400 g of body weight, which had been stunned by a blow in the head. Then, tracheas were cut in zigzag and placed into an isolated organ bath (Letica) containing Krebs-Henseleit solution at 37° C. and were bubbled with carbogen (95% $O_2$ and 5% $CO_2$). The relaxation of the trachea was measured using an isometric force transducer. The basal tension was 0.5 g. The tested compounds were accumulatively added to the bath and the effective concentration which produces a 50% of the maximum relaxation ($EC_{50}$) was calculated. The maximum relaxation was considered to be the relaxation induced by isoproterenol at $1 \times 10^{-3}M$. Results are shown in table III.

TABLE III

| Compound No | $EC_{50}(\mu M)$ |
| --- | --- |
| 11 | 1.1 |
| 13 | >10 |
| 14 | >10 |
| 16 | 0.2 |
| 18 | 78 |
| 21 | 19 |
| 22 | >50 |
| 23 | 99 |
| 24 | 2.2 |
| 26 | 0.1 |
| 30 | 0.9 |

TABLE III-continued

| Compound No | EC$_{50}$($\mu$M) |
|---|---|
| 36 | >100 |
| 38 | 1.5 |
| 40 | 2.5 |
| 41 | 1.0 |
| 42 | 31 |
| 49 | 4.8 |
| 50 | 0.25 |
| 57 | 0.5 |
| 58 | 0.05 |

Solid compositions according to the present invention for oral administration include compressed tablets, dispersible powders, granules and capsules. In tablets, one or more of the active component(s) is admixed with at least one inert diluent such as lactose, starch, mannitol, microcrystalline cellulose or calcium phosphate; granulating and disintegrating agents for example corn starch, gelatine, microcrystalline cellulose or polyvinylpyrrolidone; and lubricating agents for example magnesium stearate, stearic acid or talc. The tablets may be coated by known techniques to delay disintegration and absorption in the gastrointestinal tract and, thereby, provide a sustained action over a longer period. Gastric-film-coated or enteric film-coated can be made with sugar, gelatin, hydropropylcellulose, or acrylic resins. Tablets with a sustained action may also be obtained using an excipient which provides regressive osmosis, such as the galacturonic acid polymers. Formulations for oral use may also be presented as hard capsules of absorbable material, such as gelatin, wherein the active ingredient is mixed with an inert solid diluent and lubricating agents, or pasty materials, such as ethoxylated saturated glycerides that could exhibit controlled liberation. Soft gelatin capsules are possible wherein the active ingredient is mixed with water or an oily medium, for example peanut oil, liquid paraffin or olive oil.

Dispersible powders and granules suitable for preparation of a suspension by the addition of water provide the active ingredient in admixture with a dispersing or wetting agent, a suspending agent, such as sodium carboxymethylcellulose, methylcellulose, hydroxypropylmethylcellulose, sodium alginate, polyvinylpyrrolidone, gum tragacanth, xantham gum, gum acacia, and one or more preservatives, such as methyl or n-propyl-p-hydroxybenzoate. Additional excipients, for example sweetening, flavoring and coloring agents may also be present.

Liquid compositions for oral administration include emulsions, solutions, suspensions, syrups and elixirs containing commonly used inert diluents, such as distilled water, ethanol, sorbitol, glycerol, or propylene glycol. Such compositions may also comprise adjuvants such as wetting agents, suspending agents, sweetening, flavoring, perfuming, preserving agents and buffers.

Other compositions for oral administration include spray compositions, which may be prepared by known methods and which comprise one or more active compound(s). The spray compositions will contain a suitable propellent.

Preparations for injection according to the present invention for parenteral administration include sterile aqueous or non-aqueous solutions, suspensions or emulsions, in a non-toxic parentally-acceptable diluent or solvent. Examples of aqueous solvents or suspending media are distilled water for injection, the Ringer's solution, and isotonic sodium chloride solution. Examples of non-aqueous solvents or suspending media are propylene glycol, polyethylene glycol, vegetable oils such as olive oil, or alcohols such as ethanol. These compositions may also include adjuvants such as wetting, preserving, emulsifying and dispersing agents. They may be sterilized by one of the known methods or manufactured in the form of sterile solid compositions which can be dissolved in sterile water or some other sterile injectable medium immediately before use. When all of the components are sterile, the injectables will maintain the sterility if they are manufactured in sterile environment.

A compound of the invention may also be administered in the form of suppositories for rectal administration of the drug, or as creams, ointments jellies, solutions or suspensions for topical use and pessaries for vaginal administration.

The dosage and frequency of dose may vary depending upon symptoms, age and body weight of the patient, as well as upon the route of administration, but, in general, the compounds of the invention may be administered orally in a daily dose of from 0.1-100 mg for an adult, preferably a dosage from 2-50 mg, which may be administered either as a single dose or as divided doses. A preferred dosage for human patients is from 0.001 to 5 mg/kg of body weight, more preferably from 0.01 to 1 mg/kg of body weight.

Following are some representative preparations for tablets, capsules, syrups, aerosols and injectables. They can be prepared following standard procedures and they are useful in the treatment of diseases related with the regulation of the smooth muscle contraction, in the cardiovascular and respiratory systems and in the gastrointestinal, urinary and uterus tracts, and particularly as antihypertensive and bronchodilator agents.

| Tablets | |
|---|---|
| Compound of formula I | 100 mg |
| Dibasic calcium phosphate | 125 mg |
| Sodium starch glycolate | 10 mg |
| Talc | 12.5 mg |
| Magnesium stearate | 2.5 mg |
| | 250.0 mg |
| Hard gelatin capsules | |
| Compound of formula I | 100 mg |
| Lactose | 197 mg |
| Magnesium stearate | 3 mg |
| | 300 mg |
| Syrup | |
| Compound of formula I | 0.4 g |
| Sucrose | 45 g |
| Flavouring agent | 0.2 g |
| Sweetening agent | 0.1 g |
| Water to | 100 mL |
| Aerosol | |
| Compound of formula I | 4 g |
| Flavouring agent | 0.2 g |
| Propylene glycol to | 100 mL |
| Suitable propellent to | 1 unit |
| Injectable preparation | |
| Compound of formula I | 100 mg |
| Benzylic alcohol | 0.05 mL |
| Propylene glycol | 1 mL |
| Water to | 5 mL |

The following examples illustrate, but do not limit, the scope of the preparation of the compounds of the present invention.

PREPARATION 1

2,2-dimethyl-3,4-epoxy-1,2,3,4-tetrahydronaphthalen-1-one

To a solution of 3 g (17.4 mmol) of 2,2-dimethyl-1-oxo-1,2-dihydronaphthalene (L. H. Klemm, J. Shabtai, D. R. Taylor, *J. Org. Chem.*, 1968, 33, 1480) in 30 mL of $CH_2Cl_2$, were added 6.00 g (19.1 mmol) of m-chloroperbenzoic acid dissolved in 90 mL $CH_2Cl_2$ and the resulting mixture was stirred overnight at room temperature. The resulting solution was washed succesively with $Na_2S_2O_5$ and $NaHCO_3$ solutions and dried over $MgSO_4$. The solvent was removed to yield 3.27 g of a crude that was chromatographed on silica gel eluting with hexane-$CH_2Cl_2$ mixtures of increasing polarity. 2.09 g of the title compound of this preparation were obtained as a colorless oil (yield: 64%).

IR (film) $\nu$: 2965, 2926, 1683, 1600, 1465, 1381, 1290, 1180, 984, 898, 764 $cm^{-1}$;

$^1$H NMR (80 MHz, $CDCl_3$) $\delta$ (TMS): 7.94 (m, 1H, Ph), 7.55 (m, 3H, Ph), 4.05 (d, J=4 Hz, 1H, CHO), 3.57 (d, J=4 Hz, 1H, CHO), 1.51 (s, 3H, $CH_3$), 1.12 (s, 3H, $CH_3$).

PREPARATION 2

Trans 4-amino-2,2-dimethyl-3-hydroxy-1,2,3,4-tetrahydronaphthalen-1-one

To a solution of 1 g (5.3 mmol) of the product obtained in preparation 1 in 11 mL ethanol, 7 mL of 30% $NH_3$ were added and the mixture was stirred at room temperature for 2 days and then at reflux for two more days. The solvent was removed and the residue was solved in 1N HCl and washed with ether. The aqueous phase was basified with 1N NaOH and extracted with ether. The organic phase was dried over $MgSO_4$ and the solvent was removed, affording 0.680 g of a crude that was chromatographed on silica gel eluting with mixtures of hexane-ethyl acetate of increasing polarity. 0.580 g of the product were obtained as a colorless oil (yield: 53%).

IR (KBr) $\nu$: 3600-2700, 1679, 1597, 1447, 1373, 1290, 1276, 1081, 1051, 986, 927, 759, 736 $cm^{-1}$;

$^1$H NMR (80 MHz, $CDCl_3$) $\delta$ (TMS): 8.07 (d, J=8 Hz, 1H, Ar), 7.7-7.3 (m, 3H, Ar), 4.06 (d, J=7.2 Hz, 1H, CHN), 3.46 (d, J=7.2 Hz, 1H, CHOH), 2.32 (broad s., 3H, $NH_2$, OH), 1.39 (s, 3H, $CH_3$), 1.14 (s, 3H, $CH_3$).

PREPARATION 3

Trans 4-(4-chlorobutyrylamino)-2,2-dimethyl-3-hydroxy-1,2,3,4-tetrahydronaphthalen-1-one To a solution of 0.5 g (2.4 mmol) of the product obtained in preparation 2 in 12 mL chloroform, were added 0.096 g (2.4 mmol) of sodium hydroxide dissolved in 12 mL $H_2O$. Then, 0.269 mL (2.4 mmol) of 4-chlorobutyryl chloride were added and the mixture was stirred for 1 h at room temperature. The layers were separated and the aqueous phase was extracted with chloroform. The combined organic phases were washed with $H_2O$ and dried over $MgSO_4$. The solvent was removed and the residue chromatographed on silica gel, using hexane-ethyl acetate mixtures of increasing polarity as eluent. 0.650 g of the desired product were obtained as a colorless oil (yield: 99%).

IR (KBr) $\nu$: 3600-3200, 2966, 2929, 1648, 1536, 1292 $cm^{-1}$;

$^1$H NMR (80 MHz, $CDCl_3$) $\delta$ (TMS): 8.18 (m, 1H, Ar), 7.65 (m, 3H, Ar), 6.19 (d, J=8 Hz, 1H, NH), 5.52 (t, J=8 Hz, 1H, CHN), 3.82 (m, 3H, $CH_2Cl$+CHOH), 2.72 (m, 2H, $CH_2CO$), 2.37 (m, 3H, $CH_2$+OH), 1.47 (s, 3H, $CH_3$), 1.29 (s, 3H, $CH_3$).

PREPARATION 4

2,2-dimethyl-6-methoxy-1,2,3,4-tetrahydronaphthalen-1-one

To a solution of 10 g (56 mmol) of 6-methoxy-1,2,3,4-tetrahydronaphthalen-1-one and 19.88 g (140 mmol) of methyl iodide in 32 mL benzene, were added, under argon atmosphere, 4.42 g (92 mmol) of 55% sodium hydride. The mixture was stirred at 60° C. for 5 h and then at reflux for 2 h. The suspension was poured into methanol and the solvent was removed. The residue was dissolved in ether and washed with $H_2O$ and $Na_2CO_3$. The organic solution was dried over $MgSO_4$ and the solvent was evaporated, yielding 11.20 g of the desired product as a colorless oil (yield: 100%).

IR (film) $\nu$: 2920, 1667, 1595, 1487, 1379, 1274, 1229, 1107, 1093 $cm^{-1}$;

$^1$H NMR (80 MHz, $CDCl_3$) $\delta$ (TMS): 7.99 (d, J=9 Hz, 1H, Ar), 6.80 (dd, J=9 Hz, J=2 Hz, 1H, Ar), 6.67 (broad s, 1H, Ar), 3.82 (s, 3H, $CH_3O$), 2.93 (t, J=6.5 Hz, 2H, $CH_2Ar$), 1.94 (t, J=6.5 Hz, 2H, $CH_2$), 1.19 (s, 6H, $2CH_3$).

PREPARATION 5

1,2-dihydro-2,2-dimethyl-6-methoxynaphthalen-1-one

To a solution of 1 g (4.9 mmol) of the product obtained in preparation 4 in 5 mL $CCl_4$ were added, under argon atmosphere, 1.13 g (6.9 mmol) of N-bromosuccinimide and 0.02 g of benzoyl peroxide, and the mixture was stirred for 5 h. The imide formed was filtered and the solvent was evaporated, yielding a residue that was treated with 10 mL 10% KOH in ethanol at reflux for 1 h. After removal of the solvent, the residue was dissolved in ether, washed with $H_2O$ and $Na_2CO_3$ and dried over $MgSO_4$. The solvent was removed and the residue chromatographed on silica gel, using hexane-$CH_2Cl_2$ mixtures of increasing polarity as eluent, yielding 0.400 g of the desired product as a colorless oil (yield: 40%).

IR (film) $\nu$: 2959, 2923, 1659, 1591, 1484, 1461, 1386, 1331, 1320, 1298, 1280, 1235, 1192, 1170, 1161, 1107, 1094, 1033 $cm^{-1}$;

$^1$H NMR (80 MHz, $CDCl_3$) $\delta$ (TMS): 8.03 (d, J=8.8 Hz, 1H, Ar), 6.85 (dd, J=8.8 Hz, J=2.4 Hz, 1H, Ar), 6.67 (d, J=2.4 Hz, 1H, Ar), 6.45 (d, J=9.6 Hz, 1H, CHAr), 6.10 (d, J=9.6 Hz, 1H, CH), 3.86 (s, 3H, $CH_3O$), 1.27 (s, 6H, $2CH_3$).

PREPARATION 6

2,2-dimethyl-3,4-epoxy-6-methoxy-1,2,3,4-tetrahydronaphthalen-1-one

Following the procedure described in preparation 1, but starting from the product obtained in preparation 5, the title compound of this preparation was obtained as a colorless oil (yield: 61%).

IR (film) $\nu$: 2964, 2926, 1671, 1598, 1494, 1454, 1376, 1350, 1281, 1268, 1252, 1165, 1031 $cm^{-1}$;

$^1$H NMR (80 MHz, $CDCl_3$) $\delta$ (TMS): 7.94 (d, J=9 Hz, 1H, Ar), 7.00 (m, 2H, Ar), 3.99 (d, J=4 Hz, 1H, CHAr), 3.89 (s, 3H, CH₃O), 3.54 (d, J=4 Hz, 1H, CH), 1.49 (s, 3H, CH₃), 1.14 (s, 3H, CH₃).

PREPARATION 7

Trans
4-amino-2,2-dimethyl-3-hydroxy-6-methoxy-1,2,3,4-tetrahydronaphthalen-1-one Following the procedure described in preparation 2, but starting from the product obtained in preparation 6, the title compound of this preparation was obtained as a colorless oil (yield: 76%).

IR (film) $\nu$: 3600–3200, 2966, 2931, 1659, 1594, 1461, 1372, 1317, 1279, 1242, 1086, 1035 cm$^{-1}$;

$^1$H NMR (80 MHz, CDCl₃) δ (TMS): 8.02 (d, J=8.8 Hz, 1H, Ar), 7.17 (d, J=1.6 Hz, 1H, Ar), 6.89 (dd, J=8.8 Hz, J=1.6 Hz, 1H, Ar), 3.91 (d, J=10.4 Hz, 1H, CHNH₂), 3.89 (s, 3H, CH₃O), 3.44 (d, J=10.4 Hz, 1H, CHOH), 2.43 (broad s., 3H, NH₂+OH), 1.36 (s, 3H, CH₃), 1.12 (s, 3H, CH₃).

PREPARATION 8

Trans
4-(4-chlorobutyrylamino)-2,2-dimethyl-3-hydroxy-6-methoxy-1,2,3,4-tetrahydronaphthalen-1-one Following the procedure described in preparation 3, but starting from the product obtained in preparation 7, the title compound of this preparation was obtained as a colorless oil (yield: 82%).

IR (film) $\nu$: 3600–3200, 2965, 2930, 1649, 1594, 1565, 1536, 1457, 1279, 1241, 1094, 1034 cm$^{-1}$;

$^1$H NMR (80 MHz, CDCl₃) δ (TMS): 8.05 (d, J=8 Hz, 1H Ar), 7.93 (m, 2H, Ar), 5.94 (m, 1H, NH), 5.37 (t, J=9 Hz, 1H, CHN), 3.87 (s, 3H, CH₃O), 3.71 (m, 3H, CH₂Cl+CHOH), 2.60 (m, 2H, CH₂CO), 2.27 (m, 2H, CH₂), 1.60 (broad s., 1H, OH), 1.34 (s, 3H, CH₃), 1.16 (s, 3H, CH₃).

PREPARATION 9

6-chloro-2,2-dimethyl-1,2,3,4-tetrahydronaphthalen-1-one

Following the procedure described in preparation 4, but starting from 6-chloro-1,2,3,4-tetrahydronaphthalen-1-one (A. Rosowsky et al., *J. Heterocycl. Chem.*, 1971, 8, 809), the title compound of this preparation was obtained as a yellow oil (yield: 84%).

IR (film) $\nu$: 2958, 2921, 1677, 1587, 1380, 1299, 1226, 1216 cm$^{-1}$;

$^1$H NMR (80 MHz, CDCl₃) δ (TMS): 7.97 (d, J=9 Hz, 1H, Ar), 7.25 (m, 2H, Ar), 2.96 (t, J=6.4 Hz, 2H, CH₂Ar), 1.97 (t, J=6.4 Hz, 2H, CH₂), 1.28 (s, 6H, 2CH₃).

PREPARATION 10

6-chloro-1,2-dihydro-2,2-dimethylnaphthalen-1-one

Following the procedure described in preparation 5, but starting from the product obtained in preparation 9, the title compound of this preparation was obtained as a yellow oil (yield: 93%).

IR (film) $\nu$: 2961, 2921, 2859, 1671, 1636, 1583, 1393, 1290, 1204, 1082 cm$^{-1}$;

$^1$H NMR (80 MHz, CDCl₃) δ (TMS): 7.99 (d, J=8.8 Hz, 1H, Ar), 7.28 (m, 2H, Ar), 6.45 (d, J=9.6 Hz, 1H, CHAr), 6.15 (d, J=9.6 Hz, 1H, CH), 1.29 (s, 6H, 2CH₃).

PREPARATION 11

6-chloro-2,2-dimethyl-3,4-epoxy-1,2,3,4-tetrahydronaphthalen-1-one

Following the procedure described in preparation 1, but starting from the product obtained in preparation 10, the title compound of this preparation was obtained as a white solid (yield: 55%).

M.p.: 85.6°–85.6° C.;

IR (KBr) $\nu$: 3059, 2959, 2925, 2865, 1671, 1590, 1462, 1392, 1370, 1350, 1291, 1256, 1224, 1089, 986, 916, 895, 849, 831 cm$^{-1}$;

$^1$H NMR (80 MHz, CDCl₃) δ (TMS): 7.89 (d, J=8 Hz, 1H, Ar), 7.50 (m, 2H, Ar), 4.00 (d, J=3.2 Hz, 1H, CHAr), 3.57 (d, J=3.2 Hz, 1H, CH), 1.51 (s, 3H, CH₃), 1.13 (s, 3H, CH₃).

PREPARATION 12

Trans
4-amino-6-chloro-2,2-dimethyl-3-hydroxy-1,2,3,4-tetrahydronaphthalen-1-one Following the procedure described in preparation 2, but starting from the product obtained in preparation 11, the title compound of this preparation was obtained as a white solid (yield: 48%).

M.p.: 133.4°–133.8° C.;

IR (KBr) $\nu$: 3600–2800, 1671, 1581, 1555, 1461, 1439, 1376, 1327, 1295, 1285, 1233, 1081 cm$^{-1}$;

$^1$H NMR (80 MHz, CDCl₃) δ (TMS): 7.98 (d, J=9 Hz, 1H, Ar), 7.77 (m, 1H, Ar), 7.39 (m, 1H, Ar), 3.99 (d, J=9 Hz, 1H, CHN), 3.74 (s, 3H, NH₂+OH), 3.43 (d, J=9 Hz, 1H, CHOH), 1.33 (s, 3H, CH₃), 1.12 (s, 3H, CH₃).

PREPARATION 13

Trans
6-chloro-4-(4-chlorobutyrylamino)-2,2-dimethyl-3-hydroxy-1,2,3,4-tetrahydronaphthalen-1-one Following the procedure described in preparation 3, but starting from the product obtained in preparation 12, the title compound of this preparation was obtained as a white solid (yield: 94%).

M.p.: 94.8°–96.9° C.;

IR (KBr) $\nu$: 3600–3200, 2977, 2963, 2937, 1674, 1648, 1631, 1586, 1522, 1082, 1066 cm$^{-1}$;

$^1$H NMR (80 MHz, CD₃OD) δ (TMS): 7.96 (d, J=9 Hz, 1H, Ar), 7.37 (m, 2H, Ar), 5.24 (d, J=10 Hz, 1H, CHN), 4.00 (s, 2H, NH+OH), 3.69 (t, J=6.4 Hz, 2H, CH₂Cl), 3.68 (d, J=10 Hz, 1H, CHOH), 3.40 (m, CD₃OD), 2.59 (t, J=6.5 Hz, 2H, CH₂CO), 2.24 (m, 2H, CH₂), 1.33 (s, 3H, CH₃), 1.19 (s, 3H, CH₃).

PREPARATION 14

6-bromo-2,2-dimethyl-1,2,3,4-tetrahydronaphthalen-1-one

Following the procedure described in preparation 4, but starting from 6-bromo-1,2,3,4-tetrahydronaphthalen-1-one (K. Itoh, A. Miyake, N. Tada, M. Hirata, Y. Oka, *Chem. Pharm. Bull*, 1984, 32, 130), the title compound of this preparation was obtained as an oil (yield: 83%).

IR (film) $\nu$: 2957, 2921, 1679, 1582, 1467, 1380, 1299, 1225, 1076, 966 cm$^{-1}$;

$^1$H NMR (80 MHz, CDCl₃) δ (TMS): 7.90 (d, J=9 Hz, 1H, Ar), 7.39 (m, 2H, Ar), 2.96 (t, J=6.5 Hz, 2H,

CH₂Ar), 1.96 (t, J=6.5 Hz, 2H, CH₂), 1.20 (s, 6H, 2CH₃).

PREPARATION 15

6-bromo-1,2-dihydro-2,2-dimethylnaphthalen-1-one

Following the procedure described in preparation 5, but starting from the product obtained in preparation 14, the title compound of this preparation was obtained as an oil (yield: 74%).

IR (film) ν: 2961, 2920, 1670, 1636, 1579, 1462, 1377, 1300, 1298, 1280, 1202, 1071, 989 cm⁻¹;

¹H NMR (80 MHz, CDCl₃) δ (TMS): 7.90 (d, J=8 Hz, 1H, Ar), 7.45 (m, 2H, Ar), 6.44 (d, J=9.6 Hz, 1H, CHAr), 6.14 (d, J=9.6 Hz, 1H, CH), 1.28 (s, 6H, 2CH₃).

PREPARATION 16

6-bromo-2,2-dimethyl-3,4-epoxy-1,2,3,4-tetrahydronaphthalen-1-one

Following the procedure described in preparation 1, but starting from the product obtained in preparation 15, the title compound of this preparation was obtained as a white solid (yield: 71%).

M.p.: 103.2°–103.5° C.;

IR (film) ν: 2980, 2957, 1678, 1583, 1463, 1349, 1289, 1256, 1077, 985, 895 cm⁻¹;

¹H NMR (80 MHz, CDCl₃) δ (TMS): 7.76 (m, 3H, Ph), 3.99 (d, J=4 Hz, 1H, CHAr), 3.57 (d, J=4 Hz, 1H, CH), 1.50 (s, 3H, CH₃), 1.13 (s, 3H, CH₃).

PREPARATION 17

Trans 4-amino-6-bromo-2,2-dimethyl-3-hydroxy-1,2,3,4-tetrahydronaphthalen-1-one

Following the procedure described in preparation 2, but starting from the product obtained in preparation 16, the title compound of this preparation was obtained as a white solid (yield: 88%).

M.p.: 125.0°–126.6° C.;

IR (film) ν: 3600-2700, 1670, 1578, 1550, 1463, 1438, 1376, 1326, 1293, 1282, 1234, 1074 cm⁻¹;

¹H NMR (80 MHz, CDCl₃) δ (TMS): 7.91 (d, J=8 Hz, 1H, Ar), 7.53 (m, 1H, Ar), 7.36 (m, 1H, Ar), 3.94 (d, J=9.9 Hz, 1H, CHN), 3.44 (d, J=9.9 Hz, 1H, CHO), 2.38 (s, 3H, NH₂+OH), 1.37 (s, 3H, CH₃), 1.13 (s, 3H, CH₃).

PREPARATION 18

Trans 6-bromo-4-(4-chlorobutyrylamino)-2,2-dimethyl-3-hydroxy-1,2,3,4-tetrahydronaphthalen-1-one Following the procedure described in preparation 3, but starting from the product obtained in preparation 17, the title compound of this preparation was obtained as a white solid (yield: 100%).

M.p.: 84.2°–89.9° C.;

IR (film) ν: 3600-3200, 3061, 2963, 2935, 1679, 1648, 1630, 1581, 1523, 1280, 1076, 1064 cm⁻¹;

¹H NMR (80 MHz, CD₃OD) δ (TMS): 7.89 (d, J=8.9 Hz, 1H, Ar), 7.54 (m, 2H, Ar), 5.28 (d, J=9.9 Hz, 1H, CHN), 3.69 (t, J=6.1 Hz, 2H, CH₂Cl), 3.65 (d, J=9.9 Hz, 1H, CHO), 3.39 (m, CD₃OD), 2.58 (m, 4H, CH₂CO+OH+NH), 2.21 (m, 2H, CH₂), 1.33 (s, 3H, CH₃), 1.16 (s, 3H, CH₃).

PREPARATION 19

2,2-dimethyl-1-oxo-1,2,3,4-tetrahydronaphthalen-6-carbonitrile

Following the procedure described in preparation 4, but starting from 1-oxo-1,2,3,4-tetrahydronaphthalen-6-carbonitrile (N. L. Allinger, E. S. Jones, *J. Org. Chem.*, 1962, 27, 70), the title compound of this preparation was obtained as a white solid (yield: 73%).

M.p.: 142.5°–144.5° C.;

IR (film) ν: 2979, 2959, 2918, 2226, 1674, 1600, 1448, 1426, 1378, 1302, 1206, 968 cm⁻¹;

¹H NMR (80 MHz, CDCl₃) δ (TMS): 8.12 (d, J=8.5 Hz, 1H, Ar), 7.58 (m, 2H, Ar), 3.02 (t, J=6.4 Hz, 2H, CH₂Ar), 2.01 (t, J=6.4 Hz, 2H, CH₂), 1.23 (s, 6H, 2CH₃).

PREPARATION 20

1,2-dihydro-2,2-dimethyl-1-oxonaphthalen-6-carbonitrile

Method A. Following the procedure described in preparation 5, but starting from the product obtained in preparation 19, the title compound of this preparation was obtained as a yellow solid (yield: 20%).

M.p.: 103.6°–104.9° C.;

IR (film) ν: 3032, 2968, 2929, 2229, 1671, 1630, 1597, 1306, 1227 cm⁻¹;

¹H NMR (80 MHz, CDCl₃) δ (TMS): 8.12 (d, J=8.5 Hz, 1H, Ar), 7.58 (m, 2H, Ar), 6.47 (d, J=9.6 Hz, 1H, CHAr), 6.19 (d, J=9.6 Hz, 1H, CH), 1.32 (s, 6H, 2CH₃).

Method B. To a solution of 1 g (4 mmol) of the product obtained in preparation 15 in 9.2 mL N-methyl-2-pyrrolidone, 0.52 g (5.78 mmol) of cuprous cyanide were added and the mixture was stirred for 2 h at reflux under argon atmosphere. The mixture was poured into a 10% ethylenediamine solution and the aqueous phase was extracted with ethyl acetate. The combined organic phases were washed with H₂O and dried over MgSO₄. The solvent was removed and the residue chromatographed on silica gel, using hexane-CH₂Cl₂ mixtures of increasing polarity as eluent. 0.550 g of the desired product were obtained as a white solid (yield: 70%).

PREPARATION 21

2,2-dimethyl-3,4-epoxy-1-oxo-1,2,3,4-tetrahydronaphthalen-6-carbonitrile

Following the procedure described in preparation 1, but starting from the product obtained in preparation 20, the title compound of this preparation was obtained as a white solid (yield: 48%).

M.p.: 112.4°–115.7° C.;

IR (KBr) ν: 2970, 2927, 2226, 1691, 1604, 1463, 1437, 1345, 1304, 1286, 1259, 1185 cm⁻¹;

¹H NMR (80 MHz, CDCl₃) δ (TMS): 7.89 (d, J=8 Hz, 1H, Ar), 7.50 (m, 2H, Ar), 4.00 (d, J=3.2 Hz, 1H, CHAr), 3.57 (d, J=3.2 Hz, 1H, CH), 1.51 (s, 3H, CH₃), 1.13 (s, 3H, CH₃).

PREPARATION 22

Trans 4-amino-2,2-dimethyl-3-hydroxy-1-oxo-1,2,3,4-tetrahydronaphthalen-6-carbonitrile Following the procedure described in preparation 2, but starting from the product obtained in preparation 21, the title compound of this preparation was obtained as a white solid (yield: 55%).

M.p.: 142.8°–146.2° C.;

IR (KBr) ν: 3700–2600, 2225, 1680, 1601, 1460, 1415, 1374, 1299, 1273, 1137, 1089, 1071 cm$^{-1}$;

$^1$H NMR (80 MHz, CDCl$_3$) δ (TMS): 8.13 (m, 2H, Ar), 7.70 (d, J=8 Hz, 1H, Ar), 4.03 (m, 1H, CHN), 3.52 (m, 4H, CHO+NH$_2$+OH), 1.36 (s, 3H, CH$_3$), 1.14 (s, 3H, CH$_3$).

PREPARATION 23

Trans 4-(4-chlorobutyrylamino)-2,2-dimethyl-3-hydroxy-1-oxo-1,2,3,4-tetrahydronaphthalen-6-carbonitrile Following the procedure described in preparation 3, but starting from the product obtained in preparation 22, the title compound of this preparation was obtained as an oil (yield: 100%).

IR (KBr) ν: 3600–3200, 2964, 2927, 2230, 1865, 1721, 1686, 1649, 1527, 1283, 1059 cm$^{-1}$;

$^1$H NMR (80 MHz, CDCl$_3$) δ (TMS): 8.12 (d, J=8.5 Hz, 1H, Ar), 7.72 (m, 2H, Ar), 6.58 (d, J=9.8 Hz, 1H, NH), 5.34 (t, J=9.8 Hz, 1H, CHN), 3.64 (m, 3H, CH$_2$Cl+CHO), 2.58 (m, 2H, CH$_2$CO), 2.22 (m, 3H, CH$_2$+OH), 1.33 (s, 3H, CH$_3$), 1.15 (s, 3H, CH$_3$).

PREPARATION 24

2,2-dimethyl-6-fluoro-1,2,3,4-tetrahydronaphthalen-1-one

Following the procedure described in preparation 4, but starting from 6-fluoro-1,2,3,4-tetrahydronaphthalen-1-one (N. L. Allinger, E. S. Jones, *J. Org. Chem.*, 1962, 27, 70), the title compound of this preparation was obtained as an oil (yield: 70%).

IR (KBr) ν: 2958, 2923, 1678, 1606, 1580, 1482, 1380, 1299, 1251, 1225, 1089, 968 cm$^{-1}$;

$^1$H NMR (80 MHz, CDCl$_3$) δ (TMS): 8.06 (dd, J=8.5 Hz, J$_{HF}$=6 Hz, 1H, Ar), 7.09–6.85 (complex signal, 2H, Ar), 2.97 (t, J=6.4 Hz, 2H, CH$_2$Ar), 1.97 (t, J=6.4 Hz, 2H, CH$_2$), 1.21 (s, 6H, 2CH$_3$).

PREPARATION 25

2,2-dimethyl-1,2-dihydro-6-fluoronaphthalen-1-one

To a solution of 1.69 g (8.8 mmol) of the product obtained in preparation 24 in 34 mL CCl$_4$, were added 2 g (11.5 mmol) of N-Bromosuccinimide and 0.05 g (0.2 mmol) of benzoyl peroxide and the mixture was stirred for 4 h at reflux. The mixture was filtered and the solvent was removed. The residue was heated at 85° C. for 30 min together with 1.35 mL (8.8 mmol) of 1,8-diazabicyclo(5.4.0)undec-7-ene (DBU). The black residue was poured into a mixture of H$_2$O and diethyl ether, the layers were separated and the aqueous phase was extracted with ether. The combined organic phases were washed with H$_2$O and dried over MgSO$_4$. The solvent was removed and the residue chromatographed on silica gel, using hexane-CH$_2$Cl$_2$ mixtures of increasing polarity as eluent. 1.70 g of the desired product were obtained as an oil (yield: 100%).

IR (KBr) ν: 3057, 2961, 2919, 1670, 1600, 1566, 1478, 1384, 1295, 1256, 1236, 1090, 874 cm$^{-1}$;

$^1$H NMR (80 MHz, CDCl$_3$) δ (TMS): 8.85 (dd, J=8 Hz, J$_{HF}$=5.8 Hz, 1H, Ar), 6.93 (m, 2H, Ar), 6.47 (d, J=9.8 Hz, 1H, CHAr), 6.17 (d, J=9.8 Hz, 1H, CH), 1.29 (s, 6H, 2CH$_3$).

PREPARATION 26

2,2-dimethyl-3,4-epoxy-6-fluoro-1,2,3,4-tetrahydronaphthalen-1-one

Following the procedure described in preparation 1, but starting from the product obtained in preparation 25, the title compound of this preparation was obtained as an oil (yield: 86%).

IR (KBr) ν: 2965, 2924, 1685, 1605, 1590, 1349, 1288, 1249, 1157, 987 cm$^{-1}$;

$^1$H NMR (80 MHz, CDCl$_3$) δ (TMS): 7.97 (dd, J=7.9 Hz, J$_{HF}$=5.8 Hz, 1H, Ar), 7.27 (dd, J$_{HF}$=8.5 Hz, J=2.3 Hz, 1H, Ar), 7.13 (d of t, J=7.9 Hz, J=2.3 Hz, 1H, Ar), 4.01 (d, J=3.9 Hz, 1H, CHAr), 3.57 (d, J=3.9 Hz, 1H, CH), 1.50 (s, 3H, CH$_3$), 1.13 (s, 3H, CH$_3$).

PREPARATION 27

Trans 4-amino-2,2-dimethyl-6-fluoro-3-hydroxy-1,2,3,4-tetrahydronaphthalen-1-one Following the procedure described in preparation 2, but starting from the product obtained in preparation 26, the title compound of this preparation was obtained as an oil (yield: 61%).

IR (KBr) ν: 3600–2600, 1679, 1602, 1579, 1478, 1461, 1375, 1288, 1227, 1078 cm$^{-1}$;

$^1$H NMR (80 MHz, CDCl$_3$) δ (TMS): 8.85 (dd, J=7.9 Hz, J$_{HF}$=5.9 Hz, 1H, Ar), 7.40 (dd, J$_{HF}$=9.1 Hz, J=2.2 Hz, 1H, Ar), 7.07 (d of t, J=7.9 Hz, J=2.2 Hz, 1H, Ar), 3.93 (d, J=9.8 Hz, 1H, CHN), 3.46 (d, J=9.8 Hz, 1H, CHO), 2.40 (s, 3H, NH$_2$+OH), 1.37 (s, 3H, CH$_3$), 1.13 (s, 3H, CH$_3$).

PREPARATION 28

Trans 4-(4-chlorobutyrylamino)-2,2-dimethyl-6-fluoro-3-hydroxy-1,2,3,4-tetrahydronaphthalen-1-one Following the procedure described in preparation 3, but starting from the product obtained in preparation 27, the title compound of this preparation was obtained as an oil (yield: 100%).

IR (KBr) ν: 3600–3200, 3066, 2965, 2927, 1809, 1721, 1649, 1602, 1529, 1285, 1232, 1085, 1053 cm$^{-1}$;

$^1$H NMR (80 MHz, CDCl$_3$) δ (TMS): 8.04 (dd, J=9.4 Hz, J$_{HF}$=5.8 Hz, 1H, Ar), 7.3–6.9 (complex signal, 2H, Ar), 6.36 (d, J=8.7 Hz, 1H, NH), 5.33 (t, J=8.7 Hz, 1H, CHN), 3.62 (m, 4H, CH$_2$Cl+CHO+OH), 2.59 (t, J=6.4 Hz, 2H, CH$_2$CO), 2.18 (m, 2H, CH$_2$), 1.31 (s, 3H, CH$_3$), 1.13 (s, 3H, CH$_3$).

PREPARATION 29

2,2-dimethyl-6-N-methylacetamido-1,2,3,4-tetrahydronaphthalen-1-one

Following the procedure described in preparation 4, but starting from 6-acetamido-1,2,3,4-tetrahydronaphthalen-1-one (N. L. Allinger, E. S. Jones, *J. Org. Chem.*, 1962, 27, 70), the title compound of this preparation was obtained as a white solid (yield: 77%).

M.p.: 92.2°–94.3° C.;

IR (KBr) ν: 2959, 2915, 1670, 1649, 1593, 1377, 1300, 1215, 967 cm$^{-1}$;

$^1$H NMR (80 MHz, CDCl$_3$) δ (TMS): 8.09 (d, J=8 Hz, 1H, Ar), 7.16 (m, 2H, Ar), 3.28 (s, 3H, CH$_3$N), 3.00 (t, J=6.3 Hz, 2H, CH$_2$Ar), 2.01 (t, J=6.3 Hz, 2H, CH$_2$), 1.96 (s, 3H, CH$_3$CO), 1.24 (s, 6H, 2 CH$_3$).

PREPARATION 30

1,2-dihydro-2,2-dimethyl-6-N-methylacetamidonaphthalen-1-one

Following the procedure described in preparation 5, but starting from the product obtained in preparation 29, the title compound of this preparation was obtained as an oil (yield: 100%).

IR (KBr) $\nu$: 2960, 2923, 1636, 1565, 1341, 1300, 1243, 1157, 1104 cm$^{-1}$;

$^1$H NMR (80 MHz, CDCl$_3$) $\delta$ (TMS): 7.99 (d, J=8.6 Hz, 1H, Ar), 7.30 (s, 1H, Ar), 6.44 (m, 2H, Ar+CHAr), 6.12 (d, J=9.6 Hz, 1H, CH), 2.97 (s, 3H, CH$_3$N), 1.59 (s, 3H, CH$_3$CO), 1.30 (s, 6H, 2 CH$_3$).

PREPARATION 31

2,2-dimethyl-3,4-epoxy-6-N-methylacetamido-1,2,3,4-tetrahydronaphthalene-1-one Following the procedure described in preparation 1, but starting from the product obtained in preparation 30, the title compound of this preparation was obtained as a white solid (yield: 71%).

M.p.: 128.8°–131.2° C.;

IR (KBr) $\nu$: 3039, 2981, 2963, 1671, 1649, 1454, 1377, 1257, 1195, 1126, 981 cm$^{-1}$;

$^1$H NMR (80 MHz, CDCl$_3$) $\delta$ (TMS): 8.00 (d, J=8 Hz, 1H, Ar), 7.43 (d, J=2 Hz, 1H, Ar), 7.30 (dd, J=8 Hz, J=2 Hz, 1H, Ar), 4.03 (d, J=3.8 Hz, 1H, CHAr), 3.60 (d, J=3.8 Hz, 1H, CH), 3.33 (s, 3H, CH$_3$N), 2.00 (s, 3H, CH$_3$CO), 1.52 (s, 3H, CH$_3$), 1.17 (s, 3H, CH$_3$).

PREPARATION 32

Trans 4-amino-2,2-dimethyl-3-hydroxy-6-N-methylacetamido-1,2,3,4-tetrahydronaphthalen-1-one Following the procedure described in preparation 2, but starting from the product obtained in preparation 31, the title compound of this preparation was obtained as a white solid (yield: 58%).

M.p.: 111.9° C.;

IR (KBr) $\nu$: 3600–3000, 2964, 1671, 1595, 1374, 1293, 1079 cm$^{-1}$;

$^1$H NMR (80 MHz, CDCl$_3$) $\delta$ (TMS): 8.11 (d, J=8 Hz, 1H, Ar), 7.59 (s, 1H, Ar), 7.22 (m, 1H, Ar), 3.96 (d, J=10.1 Hz, 1H, CHAr), 3.49 (d, J=10.1 Hz, 1H, CHO), 3.32 (s, 3H, CH$_3$N), 1.99 (broad s., 6H, CH$_3$CO+OH+NH$_2$), 1.39 (s, 3H, CH$_3$), 1.16 (s, 3H, CH$_3$).

PREPARATION 33

Trans 4-(4-chlorobutyrylamino)-2,2-dimethyl-3-hydroxy-6-N-methylacetamido-1,2,3,4-tetrahydronaphthalen-1-one Following the procedure described in preparation 3, but starting from the product obtained in preparation 32, the title compound of this preparation was obtained as a white solid (yield: 84%).

M.p.: 165.4°–168.8° C.;

IR (KBr) $\nu$: 3600–3100, 2966, 1810, 1677, 1632, 1597, 1538, 1434, 1384, 1281, 1079 cm$^{-1}$;

$^1$H NMR (80 MHz, CDCl$_3$) $\delta$ (TMS): 8.10 (d, J=8.8 Hz, 1H, Ar), 7.26 (m, 2H, Ar), 6.40 (d, J=8.4 Hz, 1H, NH), 5.37 (t, J=8.4 Hz, 1H, CHN), 3.63 (m, 3H, CH$_2$Cl+CHO), 3.31 (s, 3H, CH$_3$N), 2.60 (m, 2H, CH$_2$CO), 2.22 (m, 3H, CH$_2$+OH), 2.00 (s, 3H, CH$_3$CO), 1.40 (s, 3H, CH$_3$), 1.20 (s, 3H, CH$_3$).

PREPARATION 34

2,2-dimethyl-1,2,3,4-tetrahydro-6-trifluoromethylnaphthalen-1-one

To a solution of 1.85 g (7.3 mmol) of the product obtained in preparation 14 in 50 mL of N-methyl-2-pyrrolidone were added, under argon atmosphere, 5.5 g (29 mmol) of cuprous iodide and 3.94 g (29 mmol) of sodium trifluoroacetate and the mixture was stirred for 72 h at 160° C. The solution was poured into a mixture of 600 mL H$_2$O and 600 mL diethyl ether. The layers were separated and the aqueous phase was extracted with ether. The combined organic phases were washed with H$_2$O and dried over MgSO$_4$. The solvent was removed and the residue chromatographed on silica gel, using hexane-CH$_2$Cl$_2$ mixtures of increasing polarity as eluent. 1.05 g of the desired product were obtained as an oil (yield: 59%).

IR (KBr) $\nu$: 2961, 2925, 1683, 1421, 1326, 1304, 1214, 1164, 1128, 1071, 966 cm$^{-1}$;

$^1$H NMR (80 MHz, CDCl$_3$) $\delta$ (TMS): 8.14 (d, J=8.6 Hz, 1H, Ar), 7.53 (m, 2H, Ar), 3.05 (t, J=6.4 Hz, 2H, CH$_2$Ar), 2.01 (t, J=6.4 Hz, 2H, CH$_2$), 1.23 (s, 6H, 2 CH$_3$).

PREPARATION 35

1,2-dihydro-2,2-dimethyl-6-trifluoromethylnaphthalen-1-one

Following the procedure described in preparation 5, but starting from the product obtained in preparation 34, the title compound of this preparation was obtained as an oil (yield: 100%).

$^1$H NMR (80 MHz, CDCl$_3$) $\delta$ (TMS): 8.10 (m, 1H, Ar), 7.62 (m, 2H, Ar), 6.57 (d, J=9.6 Hz, 1H, CHAr), 6.20 (d, J=9.6 Hz, 1H, CH), 1.35 (s, 3H, CH$_3$), 1.31 (s, 3H, CH$_3$).

PREPARATION 36

2.2-dimethyl-3,4-epoxy-1,2,3,4-tetrahydro-6-trifluoromethylnaphthalen-1-one

Following the procedure described in preparation 1, but starting from the product obtained in preparation 35, the title compound of this preparation was obtained as an oil (yield: 53%).

$^1$H NMR (80 MHz, CDCl$_3$) $\delta$ (TMS): 8.05 (d, J=8 Hz, 1H, Ar), 7.78 (m, 2H, Ar), 4.01 (d, J=3.9 Hz, 1H, CHAr), 3.62 (d, J=3.9 Hz, 1H, CH), 1.53 (s, 3H, CH$_3$), 1.14 (s, 3H, CH$_3$).

PREPARATION 37

7-bromo-2,2-dimethyl-1,2,3,4-tetrahydronaphthalen-1-one

Following the procedure described in preparation 4, but starting from 7-bromo-1,2,3,4-tetrahydronaphthalen-1-one (R. W. Griffin, J. D. Gass, M. A. Berwick, R. S. Shulman, *J. Org. Chem.*, 1964, 29, 2109), the title compound of this preparation was obtained as an oil (yield: 90%).

IR (KBr) $\nu$: 2957, 2921, 1683, 1583, 1469, 1398, 1302, 1209, 1107 cm$^{-1}$;

$^1$H NMR (80 MHz, CDCl$_3$) $\delta$ (TMS): 8.13 (s, 1H, Ar), 7.54 (dd, J=8 Hz, J=1.0 Hz, 1H, Ar), 7.09 (d, J=8 Hz, 1H, Ar), 2.92 (t, J=6.2 Hz, 2H, CH$_2$Ar), 1.96 (t, J=6.2 Hz, 2H, CH$_2$), 1.99 (s, 6H, 2 CH$_3$).

PREPARATION 38

7-bromo-1,2-dihydro-2,2-dimethylnaphthalen-1-one

Following the procedure described in preparation 5, but starting from the product obtained in preparation 37, the title compound of this preparation was obtained as an oil (yield: 71%).

IR (KBr) $\nu$: 3024, 2961, 2919, 2861, 1669, 1581, 1471, 1389, 1296, 1229, 1181, 836 cm$^{-1}$;

$^1$H NMR (80 MHz, CDCl$_3$) $\delta$ (TMS): 8.14 (d, J=2.0 Hz, 1H, Ar), 7.63 (dd, J=8.2 Hz, J=2.0 Hz, 1H, Ar), 7.09 (d, J=8.2 Hz, 1H, Ar), 6.47 (d, J=9.7 Hz, 1H, CHAr), 6.12 (d, J=9.7 Hz, 1H, CH), 1.27 (s, 6H, 2 CH$_3$).

PREPARATION 39

7-bromo-2,2-dimethyl-3,4-epoxy-1,2,3,4-tetrahydronaphthalen-1-one

Following the procedure described in preparation 1, but starting from the product obtained in preparation 38, the title compound of this preparation was obtained as a white solid (yield: 83%).

M.p.: 61.8°–63.4° C.;

IR (KBr) $\nu$: 3069, 3023, 2977, 2961, 1684, 1586, 1454, 1386, 1245, 1174, 1042, 931, 839 cm$^{-1}$;

$^1$H NMR (80 MHz, CDCl$_3$) $\delta$ (TMS): 8.05 (d, J=2.0 Hz, 1H, Ar), 7.69 (dd, J=9.6 Hz, J=2.0 Hz, 1H, Ar), 7.33 (d, J=9.6 Hz, 1H, Ar), 4.02 (d, J=3.9 Hz, 1H, CHAr), 3.57 (d, J=3.9 Hz, 1H, CH), 1.26 (s, 3H, CH$_3$), 1.12 (s, 3H, CH$_3$).

PREPARATION 40

Trans 4-amino-7-bromo-2,2-dimethyl-3-hydroxy-1,2,3,4-tetrahydronaphthalen-1-one

Following the procedure described in preparation 2, but starting from the product obtained in preparation 39, the title compound of this preparation was obtained as a white solid (yield: 87%).

M.p.: 105.5°–118° C.;

IR (KBr) $\nu$: 3600–2600, 1674, 1581, 1459, 1281, 1180, 1052 cm$^{-1}$;

$^1$H NMR (80 MHz, CDCl$_3$) $\delta$ (TMS): 8.16 (d, J=1.9 Hz, 1H, Ar), 7.74 (dd, J=7.6 Hz, J=1.9 Hz, 1H, Ar), 7.57 (d, J=7.6 Hz, 1H, Ar), 3.88 (d, J=9.9 Hz, 1H, CHAr), 3.44 (d, J=9.9 Hz, 1H, CHO), 2.23 (broad s., 3H, NH$_2$+OH), 1.38 (s, 3H, CH$_3$), 1.13 (s, 3H, CH$_3$).

PREPARATION 41

Trans 7-bromo-4-(4-chlorobutyrylamino)-2,2-dimethyl-3-hydroxy-1,2,3,4-tetrahydronaphthalen-1-one Following the procedure described in preparation 3, but starting from the product obtained in preparation 40, the title compound of this preparation was obtained as a white solid (yield: 100%).

M.p.: 165.4°–168.8° C.;

IR (KBr)$\nu$: 3600–3200, 3059, 2966, 2925, 2867, 1648, 1529, 1468, 1400, 1269, 1178, 1057 cm$^{-1}$;

$^1$H NMR (80 MHz, CDCl$_3$) $\delta$ (TMS): 8.12 (d, J=2.0 Hz, 1H, Ar), 7.69 (dd, J=8.2 Hz, J=2.0 Hz, 1H, Ar), 7.27 (d, J=8.2 Hz, 1H, Ar), 6.21 (d, J=8.6 Hz, 1H, NH), 5.29 (t, J=8.6 Hz, 1H, CHN), 3.61 (m, 4H, CH$_2$Cl+CHO+OH), 2.58 (t, J=6.4 Hz, 2H, CH$_2$CO), 2.19 (m, 2H, CH$_2$), 1.32 (s, 3H, CH$_3$), 1.14 (s, 3H, CH$_3$).

PREPARATION 42

6,7-dichloro-2,2-dimethyl-1,2,3,4-tetrahydronaphthalen-1-one

Following the procedure described in preparation 4, but starting from 6,7-dichloro-1,2,3,4-tetrahydronaphthalen-1-one (A. Rosowsky, M. Chaykocsky, S. A. Yeager, R. A. Amand, M. Lin. E. J. Modest, *J. Heterocycl. Chem.*, 1971, 809), the title compound of this preparation was obtained as an oil (yield: 90%).

IR (KBr) $\nu$: 2953, 2920, 2849, 1678, 1583, 1446, 1380, 1211, 1021 cm$^{-1}$;

$^1$H NMR (80 MHz, CDCl$_3$) $\delta$ (TMS): 8.09 (s, 1H, Ar), 7.34 (s, 1H, Ar), 3.93 (t, J=6.4 Hz, 2H, CH$_2$Ar), 1.97 (t, J=6.4 Hz, 2H, CH$_2$), 1.20 (s, 6H, 2CH$_3$).

PREPARATION 43

6,7-dichloro-1,2-dihydro-2,2-dimethylnaphthalen-1-one

Following the procedure described in preparation 5, but starting from the product obtained in preparation 42, the title compound of this preparation was obtained as a white solid (yield: 69%).

M.p.: 91.7°–102.3° C.;

IR (KBr) $\nu$: 3058, 2961, 2921, 1666, 1578, 1454, 1351, 1215, 1184, 1014, 888, 794 cm$^{-1}$;

$^1$H NMR (80 MHz, CDCl$_3$) $\delta$ (TMS): 8.09 (s, 1H, Ar), 7.33 (s, 1H, Ar), 6.44 (d, J=9.8 Hz, 1H, CHAr), 6.15 (d, J=9.8 Hz, 1H, CH), 1.28 (s, 6H, 2CH$_3$).

PREPARATION 44

6,7-dichloro-2,2-dimethyl-3,4-epoxy-1,2,3,4-tetrahydronaphthalen-1-one

Following the procedure described in preparation 1, but starting from the product obtained in preparation 43, the title compound of this preparation was obtained as a white solid (yield: 66%).

M.p.: 81°–85° C.;

IR (KBr) $\nu$: 3025, 2976, 2925, 1679, 1584, 1462, 1386, 1331, 1232, 1015, 905, 850 cm$^{-1}$;

$^1$H NMR (80 MHz, CDCl$_3$) $\delta$ (TMS): 8.00 (s, 1H, Ar), 7.51 (s, 1H, Ar), 3.99 (d, J=3.9 Hz, 1H, CHAr), 3.57 (d, J=3.9 Hz, 1H, CH), 1.50 (s, 3H, CH$_3$), 1.13 (s, 3H, CH$_3$).

PREPARATION 45

2,2-dimethyl-6-phenylthio-1,2,3,4-tetrahydronaphthalen-1-one

To a solution of 1.83 g (7.2 mmol) of the product obtained in preparation 14 in 18.6 mL of N-methylpyrrolidone, 0.77 mL (7.60 mmol) of thiophenol and 2.48 g (18.07 mmol) of potassium carbonate were added and the mixture was stirred at 160° C. under nitrogen atmosphere overnight. The mixture was poured into 80 mL of a H$_2$O:ether mixture and the aqueous phase was extracted with ether. The combined organic phases were washed with 5% NaOH solution and with H$_2$O and dried over MgSO$_4$. The solvent was removed and the residue was chromatographed on silica gel, using hexane-CH$_2$Cl$_2$ mixtures of increasing polarity as eluent. 1.66 g of the title compound of this preparation were obtained as a yellow oil (yield: 81%).

IR (KBr) $\nu$: 3052, 2955, 2919, 1617, 1583, 1468, 1379, 1302, 1228, 1217, 1075, 965 cm$^{-1}$;

$^1$H NMR (80 MHz, CDCl$_3$) $\delta$ (TMS): 7.90 (d, J=8.7 Hz, 1H, Ar), 7.41 (m, 5H, Ar), 7.05 (d, J=8.7 Hz, 1H, Ar), 6.99 (s, 1H, Ar), 2.88 (t, J=6.5 Hz, 2H, CH$_2$Ar), 1.93 (t, J=6.5 Hz, 2H, CH$_2$), 1.19 (s, 6H, 2CH$_3$).

PREPARATION 46

1,2-dihydro-2,2-dimethyl-6-phenylthionaphthalen-1-one

Following the procedure described in preparation 5, but starting from the product obtained in preparation 45, the title compound of this preparation was obtained as a yellow oil (yield: 90%).

IR (KBr) ν: 3052, 2959, 2920, 1665, 1572, 1469, 1305, 1076, 988 cm$^{-1}$;

$^1$H NMR (80 MHz, CDCl$_3$) δ (TMS): 7.91 (d, J=8.1 Hz, 1H, Ar) 7.44 (m, 5H, Ar), 7.08 (d, J=8.1 Hz, 1H, Ar), 6.97 (s, 1H, Ar), 6.37 (d, J=9.7 Hz, 1H, CHAr), 6.08 (d, J=9.7 Hz, 1H, CH), 1.26 (s, 6H, 2CH$_3$).

PREPARATION 47

2,2-dimethyl-3,4,-epoxy-6-phenylsulphonyl-1,2,3,4-tetrahydronaphthalen-1-one

Following the procedure described in preparation 1, but starting from the product obtained in preparation 46, the title compound of this preparation was obtained as a colorless oil (yield: 50%).

IR (KBR) ν: 2966, 1691, 1443, 1321, 1301, 1152 cm$^{-1}$;

$^1$H NMR (80 MHz, CDCl$_3$) δ (TMS): 8.2–7.5 (complex signal, 8H, Ar), 4.10 (d, J=3.9 Hz, 1H, CHAr), 3.62 (d, J=3.9 Hz, 1H, CH), 1.50 (s, 3H, CH$_3$), 1.11 (s, 3H, CH$_3$).

PREPARATION 48

2,2-dimethyl-6-pentafluoroethyl-1,2,3,4-tetrahydronaphthalen-1-one

Following the procedure described in preparation 34, but using sodium pentafluoropropionate instead of sodium trifluoroacetate, the title compound of this preparation was obtained as a colorless oil (yield: 45%).

IR (KBr) ν: 2961, 2925, 2865, 1684, 1420, 1382, 1206, 1092, 995 cm$^{-1}$;

$^1$H NMR (80 MHz, CDCl$_3$) δ (TMS): 8.15 (d, J=8 Hz, 1H, Ar), 7.52 (m, 2H, Ar), 3.06 (t, J=5 Hz, 2H, CH$_2$Ar), 2.02 (t, J=5 Hz, 2H, CH$_2$), 1.24 (s, 6H, 2CH$_3$).

PREPARATION 49

1,2-dihydro-2,2-dimethyl-6-pentafluoroethylnaphthalen-1-one

Following the procedure described in preparation 5, but starting from the product obtained in preparation 48, the title compound of this preparation was obtained as a colorless oil (yield: %).

IR (KBr) ν: 2966, 1679, 1329, 1312, 1290, 1206, 1093, 1005 cm$^{-1}$;

$^1$H NMR (80 MHz, CDCl$_3$) δ (TMS): 8.18 (m, 1H, Ar), 7.65 (m, 2H, Ar), 6.57 (d, J=9 Hz, 1H, CHAr), 6.21 (d, J=9 Hz, 1H, CH), 1.33 (s, 6H, 2CH$_3$).

PREPARATION 50

2,2-dimethyl-3,4-epoxy-6-pentafluoroethyl-1,2,3,4-tetrahydronaphthalen-1-one

Following the procedure described in preparation 1, but starting from the product obtained in preparation 49, the title compound of this preparation was obtained as a colorless oil (yield: %).

IR (KBr) ν:2972, 1691, 1289, 1195, 1145, 1092 cm$^{-1}$;

$^1$H NMR (80 MHz, CDCl$_3$) δ (TMS): 8.07 (d, J=8 Hz, 1H, Ar), 7.77 (m, 2H, Ar), 4.11 (d, J=4 Hz, 1H, CHAr), 3.63 (d, J=4 Hz, 1H, CH), 1.53 (s, 3H, CH$_3$), 1.15 (s, 3H, CH$_3$).

PREPARATION 51

2,2-diethyl-6-methoxy-1,2,3,4-tetrahydronaphthalen-1-one

Following the procedure described in preparation 4, but using ethyl iodide instead of methyl iodide, the title compound of this preparation was obtained as a yellow oil (yield: 95%).

IR (KBr) ν: 2960, 2929, 1665, 1594, 1454m 1250, 1220, 1094 cm$^{-1}$;

$^1$H NMR (80 MHz, CDCl$_3$) δ (TMS): 8.00 (d, J=8.6 Hz, 1H, Ar), 6.80 (dd, J=8.6 Hz, J=2.4 Hz, 1H, Ar), 6.66 (broad s, 1H, Ar), 3.83 (s, 3H, CH$_3$O), 2.93 (t, J=6.4 Hz, 2H, CH$_2$Ar), 1.98 (t, J=6.4 Hz, 2H, CH$_2$), 1.66 (q, J=7.2 Hz, 2H, CH$_2$CH$_3$), 1.63 (q, J=7.2 Hz, 2H, CH$_2$CH$_3$), 0.84 (t, J=7.2 Hz, 6H, 2CH$_3$).

PREPARATION 52

2,2-diethyl-6-hydroxy-1,2,3,4-tetrahydronaphthalen-1-one

A mixture of 12.56 g (0.054 mol) of the product obtained in preparation 51 and 150 mL of 48% hydrobromic acid was heated under reflux overnight. The mixture was poured into water and extracted with ether. The organic phase was extracted with 1N NaOH and dried over MgSO$_4$. After concentrating, 1.08 g (9%) of starting product were recovered. The aqueous phase was acidified with 1N HCl and extracted with ether. The organic phase was dried over MgSO$_4$ and the solvent was removed. The residue was chromatographed on silica gel, using hexane-ethyl acetate mixtures of increasing polarity as eluent. 6.47 g of the title compound of this preparation were obtained as a white solid (yield: 55%).

M.p.: 125.1°–126.3° C.;

IR (KBr) ν: 3500–3000, 2967, 2929, 1641, 1596, 1561, 1456, 1355, 1263, 1215, 1100 cm$^{-1}$;

$^1$H NMR (80 MHz, CDCl$_3$) δ (TMS): 7.96 (d, J=8.4 Hz, 1H, Ar), 6.75 (d, J=8.4 Hz, 1H, Ar), 6.66 (s, 1H, Ar), 2.90 (t, J=6.3 Hz, 2H, CH$_2$Ar), 1.99 (t, J=6.3 Hz, 2H, CH$_2$), 1.62 (m, 5H, 2CH$_2$CH$_3$+OH), 0.84 (t, J=7.3 Hz, 6H, 2CH$_3$).

PREPARATION 53

6-bromo-2,2-diethyl-1,2,3,4-tetrahydronaphthalen-1-one

A mixture of 5.30 g (0.024 mol) of the product obtained in preparation 52 and 13.93 g (0.033 mol) of triphenylphosphonium dibromide was stirred at 185° C. for 6 h. The black suspension thus obtained was poured into a mixture of water and ethyl acetate, and the layers were separated. The aqueous phase was extracted with ethyl acetate and the combined organic phases were dried over MgSO$_4$. The solvent was removed, affording a residue that was chromatographed on silica gel, eluting with hexane-ethyl acetate mixtures of increasing polarity. 3.80 g of the desired product were obtained as a yellow solid (yield: 56%).

M.p.: 49.3°–53.5° C.;

IR (KBr) ν: 2957, 2916, 2871, 1679, 1582, 1457, 1427, 1218, 989, 896, 833 cm$^{-1}$;

$^1$H NMR (80 MHz, CDCl$_3$) δ (TMS): 7.89 (d, J=8.9 Hz, 1H, Ar), 7.37 (m, 2H, Ar), 2.94 (t, J=6.4 Hz, 2H,

CH$_2$Ar), 2.00 (t, J=6.4 Hz, 2H, CH$_2$), 1.61 (m, 4H, 2C$\underline{H}_2$CH$_3$), 0.84 (t, J=7.5 Hz, 6H, 2CH$_3$).

PREPARATION 54

6-bromo-2,2-diethyl-1,2-dihydronaphthalen-1-one

Following the procedure described in preparation 5, but starting from the product obtained in preparation 53, the title compound of this preparation was obtained as a colorless oil (yield: 76%).

IR (KBr) ν: 2959, 2927, 2871, 1666, 1579, 1452, 1369, 1267, 1198, 1073, 867 cm$^{-1}$;

$^1$H NMR (80 MHz, CDCl$_3$) δ (TMS): 7.90 (d, J=8.8 Hz, 1H, Ar), 7.42 (dd, J=8.8 Hz, J=1.5 Hz, 1H, Ar), 7.40 (s, 1H, Ar), 6.69 (d, J=10.3 Hz, 1H, CHAr), 6.05 (d, J=10.3 Hz, 1H, CH), 1.94 (m, 2H, CH$_2$), 1.58 (m, 2H, CH$_2$), 0.67 (t, J=7.3 Hz, 6H, 2CH$_3$).

PREPARATION 55

6-bromo-2,2-diethyl-3,4-epoxy-1,2,3,4-tetrahydronaphthalen-1-one

Following the procedure described in preparation 1, but starting from the product obtained in preparation 54, the title compound of this preparation was obtained as a colorless oil (yield: 73%).

IR (KBr) ν: 2966, 2931, 2875, 1679, 1585, 1454, 1352, 1260, 1074, 842 cm$^{-1}$;

$^1$H NMR (80 MHz, CDCl$_3$) δ (TMS): 7.75 (m, 3H, Ar), 3.95 (d, J=3.9 Hz, 1H, CHAr), 3.66 (d, J=3.9 Hz, 1H, CH), 2.04 (m, 2H, CH$_2$), 1.51 (m, 2H, CH$_2$), 1.05 (t, J=7.5 Hz, 3H, CH$_3$), 0.71 (t, J=7.5 Hz, 3H, CH$_3$).

EXAMPLE 1

Trans 4-(1,2-dihydro-2-oxo-1-pyridyl)-2,2-dimethyl-3-hydroxy-1,2,3,4-tetrahydronaphthalen-1-one To a solution of 1 g (5.3 mmol) of the product obtained in preparation 1 in 4 mL ethanol, were added 0.35 mL (4.2 mmol) of pyridine and the mixture was stirred at reflux under argon atmosphere for 2 days. The solvent was removed and the residue was chromatographed on silica gel using CH$_2$Cl$_2$-ethyl acetate mixtures of increasing polarity as eluent. A product weighing 0.740 g was obtained and it was recrystallized from methanol yielding 0.184 g of a white solid (yield: 13%).

M.p.: 262.5°–265° C.;

IR (KBr) ν: 3600–3200, 2969, 2931, 2874, 1677, 1648, 1572, 1530, 1291, 1250, 1145, 1082 cm$^{-1}$;

$^1$H NMR (80 MHz, CDCl$_3$) δ (TMS): 8.10 (m, 1H, Ar), 7.5 (m, 3H, Ar), 7.2–6.3 (m, 5H, Ar+CHN), 4.05 (s, H$_2$O+OH), 3.96 (d, J=8 Hz, 1H, CHOH), 1.39 (s, 3H, CH$_3$), 1.27 (s, 3H, CH$_3$).

Analysis Calcd. for C$_{17}$H$_{17}$NO$_3$.0.6H$_2$O: C 69.43%; H 6.19%; N 4.77%. Found: C 69.26%; H 5.89%; N 4.58%.

EXAMPLE 2

Trans 2,2-dimethyl-3-hydroxy-4-(2-oxo-1-pyrrolidinyl)-1,2,3,4-tetrahydronaphthalen-1-one To a solution of 0.6 g (1.9 mmol) of the product obtained in preparation 3 in 180 mL of acetone, were added under argon atmosphere 6.07 g (44 mmol) of K$_2$CO$_3$ and 0.603 g (3.6 mmol) of KI and the mixture was stirred at reflux for 2 days. The solvent was removed and the residue redissolved in H$_2$O and extracted with CHCl$_3$. The organic phase was dried over MgSO$_4$ and the solvent was removed, affording 1.67 g of a crude that was chromatographed on silica gel using hexane-ethyl acetate mixtures of increasing polarity as eluent. A solid weighing 0.360 g (yield: 69%) was obtained which was recrystallized from ethanol-ether to give 0.220 g of the title compound of this example as a white solid (yield: 42%).

M.p.: 199.5°–204.3° C.;

IR (KBr) ν: 3600–3200, 2973, 2915, 2871, 1663, 1461, 1433, 1415, 1290, 1266, 1083, 1065 cm$^{-1}$;

$^1$H NMR (80 MHz, CDCl$_3$) δ (TMS): 8.08 (dd, J=7.2 Hz, J=2 Hz, 1H, Ar), 7.7–7.0 (m, 3H, Ar), 5.54 (d, J=10.5 Hz, 1H, CHN), 3.87 (d, J=10.5 Hz, 1H, CHOH), 3.25 (m, 2H, CH$_2$N), 2.60 (m, 3H, CH$_2$CO+OH), 2.16 (m, 2H, CH$_2$), 1.39 (s, 3H, CH$_3$), 1.19 (s, 3H, CH$_3$).

Analysis Calcd. for C$_{16}$H$_{19}$NO$_3$: C 70.31%; H 7.01%; N 5.12%. Found: C 70.02%; H 6.99%; N 5.01%.

EXAMPLE 3

1,2-dihydro-2,2-dimethyl-4-(2-oxo-1-pyrrolidinyl)naphthalen-1-one

To a suspension of 1.26 g (2.9 mmol) of 55% NaH in parafine and 2.5 mL of dimethylsulphoxide, were added 0.23 mL (2.9 mmol) of 2-pyrrolidone and the mixture was stirred for 15 min. The product obtained in preparation 1 (0.5 g, 2.7 mmol) was added and the stirring was maintained overnight at room temperature. The resulting solution was poured into 100 mL of H$_2$O and extracted with ethyl acetate. The organic phase was washed with H$_2$O and dried over MgSO$_4$. The solvent was removed and the residue chromatographed on silica gel using hexane-ethyl acetate mixtures of increasing polarity as eluent. The more polar fractions gave 0.300 g of the title compound of this example as a white solid (yield: 41%).

M.p.: 135.5°–136.6° C.;

IR (KBr) ν: 2978, 2955, 2874, 1691, 1666, 1643, 1586, 1411, 1310, 1287, 1221 cm$^{-1}$;

$^1$H NMR (80 MHz, CDCl$_3$) δ (TMS): 8:15 (m, 1H, Ar), 7.75–7.1 (m, 3H, Ar), 6.15 (s, 1H, CH), 3.75 (t, J=7 Hz, 2H, CH$_2$N), 2.8–2.2 (m, 4H), 1,40 (s, 6H, 2CH$_3$).

Analysis Calcd. for C$_{16}$H$_{17}$NO$_2$: C 72.27%; H 6.72%; N 5.49%. Found: C 75.33%; H 6.76%; N 5.40%.

EXAMPLE 4

2,2-dimethyl-4-(2-oxo-1-pyrrolidinyl)-1,2,3,4-tetrahydronapthalen-1,3-dione

To a suspension of 1.26 g (2.9 mmol) of 55% NaH in parafine and 2.5 mL of dimethylsulphoxide, were added 0.23 mL (2.9 mmol) of 2-pyrrolidone and the mixture was stirred for 15 min. The product obtained in preparation 1 (0.5 g, 2.7 mmol) was added and the stirring was maintained overnight at room temperature. The resulting solution was poured into 100 mL of H$_2$O and extracted with ethyl acetate. The organic phase was washed with H$_2$O and dried over MgSO$_4$. The solvent was removed and the residue chromatographed on silica gel using hexane-ethyl acetate mixtures of increasing polarity as eluent. The less polar fractions gave 0.100 g of the title compound of this example as a white solid (yield: 14%).

M.p.: 141.6°–143.8° C.;

IR (KBr) ν: 2931, 2869, 1671, 1587, 1415, 1271, 1230, 1207, 981 cm$^{-1}$;

1H NMR (80 MHz, CDCl$_3$) δ (TMS): 8.05 (m, 2H, Ar,), 7.79 (m,2H, Ar), 5.34 (s, 1H, CHN), 3.6 (m, 2H,

CH$_2$N), 2.6–1.9 (m, 4H, 2CH$_2$), 1.36 (s, 3H, CH$_3$), 1.29 (s, 3H, CH$_3$).

Analysis Calcd. for C$_{16}$H$_{17}$NO$_3$: C 70.83%; H 6.32%; N 5.16%. Found: C 71.28%; H 6.41%; N 5.02%.

EXAMPLE 5

Trans 4-(1,2-dihydro-2-oxo-1-pyridyl)-2,2-dimethyl-3-hydroxy-6-methoxy-1,2,3,4-tetrahydronaphthalen-1-one Following the procedure described in example 1, but starting from the product obtained in preparation 6, the title compound of this example was obtained as a white solid (yield : 24%).

M.p.: 224.9°–225.2° C.;

IR (KBr) $\nu$: 3600–3200, 2946, 1663, 1648, 1594, 1565, 1534, 1323, 1285, 1256, 1243, 1149, 1104, 1041 cm$^{-1}$;

$^1$H NMR (80 MHz, CD$_3$OD) $\delta$ (TMS): 8.2–6.2 (complex signal, 8H), 4.77 (H$_2$O+OH), 4.07 (d, J=10.4 Hz, 1H, CHOH), 3.87 (s, 3H, CH$_3$O), 1.34 (s, 3H, CH$_3$), 1.23 (s, 3H, CH$_3$).

Analysis Calcd. for C$_{18}$H$_{19}$NO$_4$: C 69.01%; H 6.11%; N 4.47%. Found: C 69.38%; H 6.33%; N 4.37%.

EXAMPLE 6

1,2-dihydro-4-(1,2-dihydro-2-oxo-1-pyridyl)-2,2-dimethyl-6-methoxynaphthalen-1-one To a solution of 1.14 g (3.63 mmol) of the product in example 5 in 45 mL of dioxane, were added, under argon atmosphere, 1.16 g of NaOH/silica (Merck 1567) and the mixture was stirred for 30 min at reflux. The solvent was removed and the residue chromatographed on silica gel using hexane-ethyl acetate mixtures of increasing polarity as eluent. 0.440 g of the title compound of this example were obtained as a white solid (yield: 41%). M.p.: 163.6° C.;

IR (KBr) $\nu$: 3011, 2967, 2913, 2860, 1657, 1586, 1520, 1354, 1264, 1236, 1084, 1030 843, 769 cm$^{-1}$;

$^1$H NMR (80 MHz, CDCl$_3$) $\delta$ (TMS): 8.13 (d, J=9.2 Hz, 1H, Ar), 7.44 (ddd, J=8.8 Hz, J=2.4 Hz, 1H, Ar), 7.22 (m, 1H, Ar), 6.92 (dd, J=8.8 Hz, J=2.4 Hz, 1H, Ar), 6.67 (d, J=9.2 Hz, 1H, Ar), 6.28 (m, 2H, Ar), 6.20 (s, 1H, CH), 3.78 (s, 3H, CH$_3$O), 1.43 (s, 3H, CH$_3$), 1.37 (s, 3H, CH$_3$).

Analysis Calcd. for C$_{18}$H$_{17}$NO$_3$: C 73.20%; H 5.80%; N 4.74%. Found: C 73.25%; H 6.07%; N 4.87%.

EXAMPLE 7

Trans 2,2-dimethyl-3-hydroxy-6-methoxy-4-(2-oxo-1-pyrrolidinyl)-1,2,3,4-tetrahydronaphthalen-1-one Following the procedure described in example 2, but starting from the product obtained in preparation 8, the title compound of this example was obtained as a white solid (yield: 47%).

M.p.: 215.1°–215.3° C.;

IR (KBr) $\nu$: 3600–3200, 3011, 2963, 2929, 2872, 1657, 1592, 1437, 1289, 1276, 1235, 1087, 1070, 1032 cm$^{-1}$;

$^1$H NMR (80 MHz, CDCl$_3$) $\delta$ (TMS): 8.07 (d, J=9 Hz, 1H, Ar), 6.93 (dd, J=9 Hz, J=2.4 Hz, 1H, Ar), 6.60 (broad s., 1H, Ar), 5.48 (d, J=10.4 Hz, 1H, CHN), 3.85 (d, J=10.4 Hz, 1H, CHOH), 3.85 (s, 3H, CH$_3$O), 3.6–1.8 (complex signal, 7H), 1.37 (s, 3H, CH$_3$), 1.17 (s, 3H, CH$_3$).

Analysis Calcd. for C$_{17}$H$_{21}$NO$_4$: C 67.31%; H 6.98%; N 4.62%. Found C 67.47%; H 7.16%; N 4.51%.

EXAMPLE 8

1,2-dihydro-2,2-dimethyl-6-methoxy-4-(2-oxo-1-pyrrolidinyl)naphthalen-1-one

Following the procedure described in example 3, but starting from the product obtained in preparation 6, the title compound of this example was obtained as a white solid (yield: 32%).

M.p.: 93.8°–99.5° C.;

IR (KBr) $\nu$: 2964, 2925, 2865, 1679, 1654, 1641, 1592, 1408, 1267, 1247, 1238, cm$^{-1}$;

$^1$H NMR (80 MHz, CDCl$_3$) $\delta$ (TMS): 8.09 (d, J=9 Hz, 1H, Ar), 6.90 (dd, J=9 Hz, J=2.4 Hz, 1H, Ar), 6.61 (d, J=2.4 Hz, 1H, Ar), 6.11 (s, 1H, CH), 3.87 (s, 3H, CH$_3$O), 3.70 (t, J=5.5 Hz, 2H, CH$_2$N), 2.60 (m, 2H, CH$_2$CO), 2.29 (m, 2H, CH$_2$), 1.34 (s, 6H, 2CH$_3$).

Analysis Calcd. for C$_{17}$H$_{19}$NO$_3$: C 71.56%; H 6.71%; N 4.91%. Found : C 71.66%; H 6.84%; N 4.73%.

EXAMPLE 9

Trans 6-chloro-4-(1,2-dihydro-2-oxo-1-pyridyl)-2,2-dimethyl-3-hydroxy-1,2,3,4-tetrahydronaphthalen-1-one Following the procedure described in example 1, but starting from the product obtained in preparation 11, the title compound of this example was obtained as a white solid (yield: 32%).

M.p.: 255.0°–255.0° C.;

IR (KBr) $\nu$: 3600–3200, 2980, 2962, 2938, 1672, 1648, 1585, 1568, 1534, 1286, 1147, 1077 cm$^{-1}$;

$^1$H NMR (80 MHz, CDCl$_3$) $\delta$ (TMS): 8.05 (m, 1H, Ar), 7.60–6.30 (complex signal, 7H, Ar+CHN), 3.95 (d, J=10.4 Hz, 1H, CHOH), 3.67 (s, 1H, OH), 1.38 (s, 3H, CH$_3$), 1.27 (s, 3H, CH$_3$)

Analysis Calcd. for C$_{17}$H$_{16}$ClNO$_3$: C 64.26%; H 5.08%; N 4.41%. Found: C 64.32%; H 5.13%; N 4.31%.

EXAMPLE 10

Trans 3-acetoxy-6-chloro-4-(1,2-dihydro-2-oxo-1-pyridyl)-2,2-dimethyl-1,2,3,4-tetrahydronaphthalen-1-one To a solution of 0.130 g (0.4 mmol) of the product obtained in example 9 in 1.6 mL pyridine, were added 0.8 mL of acetic anhydride and the mixture was stirred for 3 days at room temperature. The solvent was removed, the residue was redissolved in CH$_2$Cl$_2$ and washed with NaHCO$_3$ and H$_2$O. The organic phase was dried over MgSO$_4$ and the solvent was removed, affording 0.280 g of a crude that was chromatographed on silica gel using hexane-ethyl acetate mixtures of increasing polarity as eluent. 0.130 g of the title compound of this example were obtained as a white solid (yield: 90%).

M.p.: 224.1°–225.2° C.;

IR (KBr) $\nu$: 3021, 2967, 2910, 1735, 1680, 1657, 1585, 1530, 1366, 1255, 1221, 1149, 1026 cm$^{-1}$;

$^1$H NMR (80 MHz, CDCl$_3$) $\delta$ (TMS): 8.08 (d, J=8 Hz, 1H, Ar) 7.50–6.10 (complex signal, 7H, Ar+CHN), 5.46 (d, J=10.4 Hz, 1H, CHO), 1.99 (s, 3H, COCH$_3$), 1.33 (s, 3H, CH$_3$), 1.27 (s, 3H, CH$_3$).

EXAMPLE 11

6-chloro-1,2-dihydro-4-(1,2-dihydro-2-oxo-1-pyridyl)-2,2-dimethylnaphthalen-1-one To a solution of 0.120 g (0.33 mmol) of the product obtained in example 10 in 2 mL of toluene, were added dropwise and under argon atmosphere 0.04 mL (0.4 mmol) of 1,8-diazabicyclo(5,4,0)undec-7-ene (DBU) and the mixture was stirred at reflux overnight. The solvent was removed and the residue was redissolved in ethyl acetate. The solution was washed with $H_2O$ and dried over $MgSO_4$. The solvent was removed, affording a crude that was chromatographed on silica gel using hexane-ethyl acetate mixtures of increasing polarity as eluent. 0.070 g of the title compound of this example were obtained as a white solid (yield: 71%).

M.p.: 192.5° C.;

IR (KBr) $\nu$: 3057, 2956, 2923, 1660, 1584, 1524, 1338, 1155 cm$^{-1}$;

$^1$H NMR (80 MHz, CDCl$_3$) $\delta$ (TMS): 8.07 (d, J=8 Hz, 1H, Ar), 7.40 (m, 3H, Ar), 6.74 (m, 2H, Ar), 6.30 (m, 1H, Ar), 6.24 (s, 1H, CH), 1.45 (s, 3H, CH$_3$), 1.38 (s, 3H, CH$_3$).

Analysis Calcd. for $C_{17}H_{14}ClNO_2.0.25\ H_2O$: C 67.10%; H 4.76%; N 4.61%. Found: C 67.22%; H 5.03%; N 4.45%.

EXAMPLE 12

Trans 6-chloro-2,2-dimethyl-3-hydroxy-4-(2-oxo-1-pyrrolidinyl)-1,2,3,4-tetrahydronaphthalen-1-one Following the procedure described in example 2, but starting from the product obtained in preparation 13, the title compound of this example was obtained as a white solid (yield: 75%).

M.p.: 230.1°-230.5° C.;

IR (KBr) $\nu$: 3600-3200, 2967, 2929, 1665, 1648, 1558, 1461, 1282, 1081 cm$^{-1}$;

$^1$H NMR (80 MHz, CDCl$_3$) $\delta$ (TMS): 8.02 (d, J=8 Hz, 1H, Ar), 7.32 (m, 2H, Ar), 5.47 (d, J=10.4 Hz, 1H, CHN), 3.86 (d, J=10.4 Hz, 1H, CHOH), 3.37 (m, 2H, CH$_2$N), 2.93 (s, 1H, OH), 2.62 (m, 2H, CH$_2$CO), 2.19 (m, 2H, CH$_2$), 1.38 (s, 3H, CH$_3$), 1.17 (s, 3H, CH$_3$).

Analysis Calcd. for $C_{16}H_{18}ClNO_3$: C 62.44%; H 5.89%; N 4.55%. Found: C 62.84%; H 6.16%; N 4.40%.

EXAMPLE 13

6-chloro-1,2-dihydro-2,2-dimethyl-4-(2-oxo-1-pyrrolidinyl)naphthalen-1-one

Following the procedure described in example 3, but starting from the product obtained in preparation 11, the title compound of this example was obtained as a white solid (yield: 48%).

M.p.: 161.3°-161.7° C.;

IR (KBr) $\nu$: 3060, 2982, 2865, 1685, 1671, 1580, 1270, 1230 cm$^{-1}$;

$^1$H NMR (80 MHz, CDCl$_3$) $\delta$ (TMS): 8.05 (m, 2H, Ar), 7.72 (dd, J=8 Hz, J=2 Hz, 1H, Ar), 5.30 (s, 1H, CH), 3.61 (m, 2H, CH$_2$N), 2.6-1.8 (complex signal, 4H), 1.34 (s, 3H, CH$_3$), 1.27 (s, 3H, CH$_3$).

Analysis Calcd. for $C_{16}H_{16}ClNO_2.1H_2O$: C 62.44%; H 5.89%; N 4.55%. Found: C 62.52%; H 5.45%; N 4.41%.

EXAMPLE 14

Trans 6-bromo-4-(1,2-dihydro-2-oxo-1-pyridyl)-2,2-dimethyl-3hydroxy-1,2,3,4-tetrahydronaphthalen-1-one Method A—Following the procedure described in example 1, but starting from the product obtained in preparation 16, the title compound of this example was obtained as a white solid (yield: 36%).

M.p.: 250.4°-250.4° C.;

IR (KBr) $\nu$: 3600-3200, 2937, 1671, 1648, 1566, 1534, 1285, 1253, 1161, 1148, 1078, 843, 773 cm$^{-1}$;

$^1$H NMR (80 MHz, CDCl$_3$) $\delta$ (TMS): 7.96 (m, 1H, Ar), 7.54 (m, 3H, Ar), 7.2-6.2 (m, 4H, Ar+CHN), 4.05 (s, H$_2$O+OH), 3.95 (d, J=8 Hz, 1H, CHOH), 1.38 (s, 3H, CH$_3$), 1.25 (s, 3H, CH$_3$).

Analysis Calcd. for $C_{17}H_{16}BrNO_3$: C 56.37%; H 4.45%; N 3.87%. Found: C 56.19%; H 4.46%; N 3.87%.

Method B—To a solution of 10 g (37.4 mmol) of the product obtained in preparation 16 in 135 mL of anhydrous tetrahydrofurane, were added under argon atmosphere 12.4 g (74.8 mmol) of 2-trimethylsilyloxypyridine. The mixture was cooled to 0° C. and 11.76 g (37.4 mmol) of tetrabutylammonium fluoride trihydrate were added. After stirring for five days at room temperature, the mixture was poured into water and the aqueous phase was extracted with ethyl acetate. The solution was dried over MgSO$_4$ and the solvent was removed, affording a crude that was treated with CH$_2$Cl$_2$. The suspension thus obtained was filtered, affording 3.70 g of the title compound of this example as a white solid. The filtrate was chromatographed on silica gel using hexane-ethyl acetate mixtures of increasing polarity as eluent, giving 0.98 g more of product (yield: 35%).

EXAMPLE 15

Trans 3-acetoxy-6-bromo-4-(1,2-dihydro-2oxo-1-pyridyl)-2,2-dimethyl-1,2,3,4-tetrahydronaphthalen-1-one Following the procedure described in example 10, but starting from the product obtained in example 14, the title compound of this example was obtained as a white solid (yield: 61%).

M.p.: 225.3° C.;

IR (KBr) $\nu$: 3072, 2967, 2931, 1735, 1685, 1656, 1584, 1530, 1366, 1222, 1148, 1026, 851, 768 cm$^{-1}$;

$^1$H NMR (80 MHz, CD$_3$OD) $\delta$ (TMS): 7.96 (m, 1H, Ar), 7.8-7.2 (m, 3H, Ar), 7.1-6.2 (m, 4H, Ar+CHN), 5.64 (d, J=10.4 Hz, 1H, CHO), 4.67 (s, H$_2$O), 3.33 (m, CD$_3$OD), 1.98 (s, 3H, CH$_3$CO), 1.33 (s, 3H, CH$_3$), 1.26 (s, 3H, CH$_3$).

Analysis Calcd. for $C_{19}H_{18}BrNO_4$: C 56.45%; H 4.49%; N 3.46%. Found: C 56.19%; H 4.73%; N 3.45%.

EXAMPLE 16

6-bromo-1,2-dihydro-4-(1,2-dihydro-2-oxo-1-pyridyl)-2,2-dimethylnaphthalen-1-one Method A—Following the procedure described in example 6, but starting from the product obtained in example 14, the title compound of this example was obtained as a white solid (yield: 45%).

M.p.: 172.3° C.;

IR (KBr) $\nu$: 3054, 2958, 1658, 1579, 1523, 1337, 1153, 992 cm$^{-1}$;

$^1$H NMR (80 MHz, CDCl$_3$) $\delta$ (TMS): 7.99 (d, J=8 Hz, 1H, Ar), 7.50 (m, 2H, Ar), 7.23 (d, J=6.4 Hz, 1H, Ar), 6.98 (d, J=2 Hz, 1H, Ar), 6.67 (d, J=8 Hz, 1H, Ar), 6.34 (m, 1H, Ar), 6.23 (s, 1H, CH), 1.44 (s, 3H, CH$_3$), 1.38 (s, 3H, CH$_3$).

Analysis Calcd. for $C_{17}H_{14}BrNO_2$: C 59.32%; H 4.10%; N 4.07%. Found: C 59.49%; H 4.21%; N 4.06%.

Method B—Following the procedure described in example 11, but starting from the product obtained in example 15, the title compound of this example was obtained as a white solid (yield: 83%).

EXAMPLE 17

Trans 6-bromo-4-(1,2-dihydro-5-nitro-2-oxo-1-pyridyl)-2,2-dimethyl-3-hydroxy-1,2,3,4-tetrahydronaphthalen-1-one Following the procedure described in example 1, but starting from the product obtained in preparation 16 and 5-nitro-2-pyridone, the title compound of this example was obtained as a white solid (yield: 36%).

M.p.: 98.6°–106° C.;

IR (KBr) $\nu$: 3600–3200, 3067, 2969, 2929, 1670, 1581, 1555, 1338, 1261, 1076 cm$^{-1}$;

$^1$H NMR (80 MHz, CDCl$_3$) δ (TMS): 8.3–7.9 (m, 3H, Ar), 7.65 (d, J=8.4 Hz, 1H, Ar), 7.06 (d, J=8.4Hz, 1H, Ar), 6.80 (s, 1H, Ar), 6.49 (d, J=9.2 Hz, 1H, CHN), 4.07 (m, 1H, CHO), 1.86 (broad s, OH), 1.41 (s, 3H, CH$_3$), 1.25 (s, 3H, CH$_3$).

Analysis Calcd. for C$_{17}$H$_{15}$BrN$_2$O$_5$: C 50.14%; H 3.71%; N 6.88%. Found: C 50.21%; H 3.99%; N 6.52%.

EXAMPLE 18

Trans 6-bromo-2,2-dimethyl-3-hydroxy-4-(2-oxo-1-pyrrolidinyl)-1,2,3,4-tetrahydronaphthalen-1-one Following the procedure described in example 2, but starting from the product obtained in preparation 18, the title compound of this example was obtained as a white solid (yield: 63%).

M.p.: 217.2° C.;

IR (KBr) $\nu$: 3600–3100, 2975, 2871, 1649, 1580, 1459, 1417, 1286, 1076 cm$^{-1}$;

$^1$H NMR (80 MHz, CD$_3$OD) δ (TMS): 7.92 (d, J=8.3 Hz, 1H, Ar), 7.60 (m, 1H, Ar), 7.34 (m, 1H, Ar), 5.38 (d, J=10.3 Hz, 1H, CHN), 4.73 (s, H$_2$O+OH), 3.92 (d, J=10.3 Hz, 1H, CHO), 3.46 (t, J=7.6 Hz, 2H, CH$_2$N), 3.32 (m, CD$_3$OD), 2.62 (m, 2H, CH$_2$CO), 2.17 (m, 2H, CH$_2$), 1.33 (s, 3H, CH$_3$), 1.16 (s, 3H, CH$_3$).

Analysis Calcd. for C$_{16}$H$_{18}$BrNO$_3$: C 54.56%; H 5.15%; N 3.98%. Found: C 54.53%; H 5.69%; N 3.78%.

EXAMPLE 19

Trans 3-acetoxy-6-bromo-2,2-dimethyl-4-(2-oxo-1pyrrolidinyl)-1,2,3,4-tetrahydronaphthalen-1-one Following the procedure described in example 10, but starting from the product obtained in example 18, the title compound of this example was obtained as a white solid (yield: 95%).

M.p.: 194.9° C.;

IR (KBr) $\nu$: 2973, 2912, 1738, 1675, 1582, 1420, 1370, 1281, 1244, 1219, 1022, 978 cm$^{-1}$;

$^1$H NMR (80 MHz, CDCl$_3$) δ (TMS): 7.95 (d, J=8 Hz, 1H, Ar), 7.59 (broad s, J=8.3 Hz, 1H, Ar), 7.30 (broad s, 1H, Ar), 5.74 (d, J=10.1Hz, 1H, CHN), 5.28 (d, J=10.1 Hz, 1H, CHO), 3.5–3.0 (m, 2H, CH$_2$N), 2.52 (m, 2H, CH$_2$CO), 2.13 (m, 5H, CH$_3$CO+CH$_2$), 1.26 (s, 6H, 2CH$_3$).

Analysis Calcd. for C$_{18}$H$_{20}$BrNO$_4$: C 54.84%; H 5.11%; N 3.55%. Found: C 54.52%; H 5.21%; N 3.37%.

EXAMPLE 20

6-bromo-2,2-dimethyl-4-(2-oxo-1-pyrrolidinyl)-1,2,3,4-tetrahydronaphthalen-1,3-dione Following the procedure described in example 4, but starting from the product obtained in preparation 16, the title compound of this example was obtained as a white solid (yield: 20%).

M.p: 36.0°–45.2° C.;

IR (KBr) $\nu$: 2973, 2927, 2867, 1684, 1575, 1453, 1268 cm$^{-1}$;

$^1$H NMR (80 MHz, CDCl$_3$) δ (TMS): 8.23 (m, 1H, Ar), 7.94 (m, 2H, Ar), 5.29 (s, 1H, CHN), 3.52 (m, 2H, CH$_2$N), 2.6–1.9 (m, 4H, 2CH$_2$), 1.35 (s, 3H, CH$_3$), 1.29 (s, 3H, CH$_3$).

Analysis Calcd. for C$_{16}$H$_{16}$BrNO$_3$: C 54.87%; H 4.61%; N 4.00%. Found: C 55.12%; H 4.81%; N 3.66%.

EXAMPLE 21

6-bromo-1,2-dihydro-2,2-dimethyl-4-(2-oxo-1-pyrrolidinyl)naphthalen-1-one

Following the procedure described in example 3, but starting from the product obtained in preparation 16, the title compound of this example was obtained as a white solid (yield: 26%).

M.p.: 96.1°–96.2° C.;

IR (KBr) $\nu$: 2963, 2869, 1684, 1666, 1579, 1407, 1305, 1244, 1156, 990, 841 cm$^{-1}$;

$^1$H NMR (80 MHz, CDCl$_3$) δ (TMS): 7.94 (d, J=8 Hz, 1H, Ar), 7.53 (dd, J=8 Hz, J=1.9 Hz, 1H, Ar), 7.26 (d, J=1.9 Hz, 1H, Ar), 6.13 (s, 1H, CH), 3.69 (t, J=7.1 Hz, 2H, CH$_2$N), 2.58 (m, 2H, CH$_2$CO), 2.31 (m, 2H, CH$_2$), 1.35 (s, 6H, 2CH$_3$).

Analysis Calcd. for C$_{16}$H$_{16}$BrNO$_2$: C 57.50%; H 4.83%; N 4.19%. Found: C 57.93%; H 4.98%; N 4.13%.

EXAMPLE 22

Trans 6-bromo-4-(2,3-dihydro-1-oxo-1H-isoindol-2-yl)-2,2-dimethyl-3-hydroxy-1,2,3,4-tetrahydronaphthalen-1-one To a solution of 0.4 g (1.41 mmol) of the product obtained in preparation 17 in 8 mL of anhydrous acetonitrile, were added 0.322 g (1.41 mmol) of methyl 2-bromomethylbenzoate, 0.566 g (4.10 mmol) of potassium carbonate and 0.114 g (0.69 mmol) of potassium iodide and the mixture was stirred at reflux under nitrogen atmosphere for 24 h. The cooled mixture was vacuum filtered through celite. The precipitate was washed with ethyl acetate and the filtrates were combined and evaporated. The residue was dissolved in ethyl acetate, washed with water and aqueous sodium thiosulfate and dried over MgSO$_4$. The solvent was removed and the residue was chromatographed on silica gel, using hexane-ethyl acetate mixtures of increasing polarity as eluent. 0.210 g of the title compound of this example were obtained as a white solid (yield: 37%).

M.p.: 249.5°–252.5° C.;

IR (KBr) $\nu$: 3600–3200, 2965, 2925, 2867, 1665, 1580, 1464, 1406, 1280, 1076, 938, 733 cm$^{-1}$;

$^1$H NMR (80 MHz, CDCl$_3$) δ (TMS): 7.93 (m, 2H, Ar), 7.54 (m, 4H, Ar), 7.24 (m, 1H, Ar), 5.77 (d, J=10.2 Hz, 1H, CHN), 4.4–3.9 (m, 3H, CH$_2$+CHO), 1.63 (broad s, OH), 1.41 (s, 3H, CH$_3$), 1.26 (s, 3H, CH$_3$).

Analysis Calcd. for C$_{20}$H$_{18}$BrNO$_3$.0.25H$_2$O: C 59.33%; H 4.57%; N 3.46%. Found: C 59.38%; H 4.81%; N 3.45%.

EXAMPLE 23

Trans 4-(1,2-dihydro-2-oxo-1-pyridyl)-2,2-dimethyl-3-hydroxy-1-oxo-1,2,3,4-tetrahydronaphthalen-6-carbonitrile Following the procedure described in example 1, but starting from the product obtained in preparation 21, the title compound of this example was obtained as a white solid (yield: 59%).

M.p.: 243.7°–244.4° C.;

IR (KBr) $\nu$: 3600–3100, 3069, 2978, 2935, 2231, 1686, 1643, 1567, 1530, 1289, 1255, 1146, 1073 cm$^{-1}$;

$^1$H NMR (80 MHz, DMSO) $\delta$ (TMS): 7.98 (m, 2H, Ar), 7.49 (m, 2H, Ar), 6.36 (m, 3H, Ar), 5.74 (m, 1H, CHN), 5.23 (d, J=9 Hz, 1H, CHO), 3.30 (s, H$_2$O+OH), 2.50 (m, DMSO), 1.25 (s, 3H, CH$_3$), 1.10 (s, 3H, CH$_3$).

Analysis Calcd. for C$_{18}$H$_{16}$N$_2$O$_3$: C 70.12%; H 5.23%; N 9.09%. Found: C 69.94%; H 5.40%; N 8.79%.

EXAMPLE 24

Trans 3-acetoxy-4-(1,2-dihydro-2-oxo-1-pyridyl)-2,2-dimethyl-1-oxo-1,2,3,4-tetrahydronaphthalen-6-carbonitrile Following the procedure described in example 10, but starting from the product obtained in example 23, the title compound of this example was obtained as a white solid (yield: 85%).

M.p.: 204.3°–204.6° C.;

IR (KBr) $\nu$: 3076, 2965, 2931, 2233, 1738, 1696, 1656, 1583, 1530, 1367, 1256, 1218, 1148, 1030 cm$^{-1}$; $^1$H NMR (80 MHz, CDCl$_3$) $\delta$ (TMS): 8.24 (d, J=8 Hz, 1H, Ar), 7.8-6.1 (complex signal, 7H, Ar+CHN), 5.51 (d, J=10.7 Hz, 1H, CHO), 2.01 (s, 3H, COCH$_3$), 1.30 (m, 6H, 2CH$_3$).

Analysis Calcd. for C$_{20}$H$_{18}$N$_2$O$_4$: C 68.56%; H 7.00%; N 5.18%. Found: C 68.51%; H 7.52%; N 5.48%.

EXAMPLE 25

Trans 4-(1,2-dihydro-2-oxo-1-pyridyl)-2,2-dimethyl-3-formyloxy-1-oxo-1,2,3,4-tetrahydronaphthalen-6-carbonitrile Following the procedure described in example 10, but starting from the product obtained in example 23 and using pure formic acid instead of acetic anhydride, the title compound of this example was obtained as a white solid (yield: 55%).

M.P.: 191.0°–193.3° C.;

IR (KBr) $\nu$: 3068, 2970, 2931, 2229, 1720, 1695, 1654, 1583, 1530, 1146 cm$^{-1}$;

$^1$H NMR (80 MHz, CDCl$_3$) $\delta$ (TMS): 8.25 (d, J=8.2 Hz, 1H, Ar), 8.02 (s, 1H, OCHO), 7.74 (m, 1H, Ar), 7.5-6.8 (complex signal, 4H, Ar+CHAr), 6.68 (d, J=8.9 Hz, 1H, Ar), 6.24 (t, J=6.7 Hz, 1H, Ar), 5.64 (d, J=10.9 Hz, 1H, CHO), 1.33 (m, 6H, 2 CH$_3$).

Analysis Calcd. for C$_{19}$H$_{16}$N$_2$O$_4$.0.25 H$_2$O: C 66.96%; H 4.84%; N 8.22%. Found: C 67.17%; H 5.20%; N 7.66%.

EXAMPLE 26

1,2-dihydro-4-(1,2-dihydro-2-oxo-1-pyridyl)-2,2-dimethyl-1-oxonaphthalene-6-carbonitrile Method A— Following the procedure described in example 11, but starting from the product obtained in example 24, the title compound of this example was obtained as a white solid (yield: 97%).

M.P.: 186.9° C.;

IR (KBr) $\nu$: 3055, 2965, 1679, 1664, 1582, 1523, 1345, 1218, 994 cm$^{-1}$;

$^1$H NMR (80 MHz, CDCl$_3$) $\delta$ (TMS): 8.20 (d, J=8 Hz, 1H, Ar), 7.60 (m, 2H, Ar), 7.20 (m, 2H, Ar), 6.69 (d, J=8 Hz, 1H, Ar), 6.30 (s, 1H, Ar), 6.30 (s, 1H, CH), 1.47 (s, 3H, CH$_3$), 1.40 (s, 3H, CH$_3$).

Analysis Calcd. for C$_{18}$H$_{14}$N$_2$O$_2$: C 74.47%; H 4.86%; N 9.65%. Found: C 74.55%; H 4.97%; N 9.38%.

Method B— To a solution of 1.55 (4.2 mmol) of the product obtained in example 14 in 9.5 mL of N-methylpyrrolidone, were added, under argon atmosphere, 0.56 g (6.1 mmol) of cuprous cyanide and the mixture was stirred for 2.5 h at reflux. The mixture was poured into a 10% ethylenediamine solution, and the aqueous phase was extracted with ethyl acetate. The combined organic phases were washed with H$_2$O and dried over MgSO$_4$. The solvent was removed and the residue chromatographed on silica gel, using hexane-ethyl acetate mixtures of increasing polarity as eluent. 0.750 g of the title compound of this example were obtained as a white solid (yield: 63%).

EXAMPLE 27

Trans 4-(1,2-dihydro-5-nitro-2-oxo-1-pyridyl)-2,2-dimethyl-3-hydroxy-1-oxo-1,2,3,4-tetrahydronaphthalen-6-carbonitrile Following the procedure described in example 26B, but starting from the product obtained in example 17, the title compound of this example was obtained as a white solid (yield: 13%).

M.P.: 149.3°–159.9° C.;

IR (KBr) $\nu$: 3600–3200, 3069, 2969, 2930, 2230, 1666, 1606, 1555, 1341, 1263, 1202, 1118 cm$^{-1}$;

$^1$H NMR (80 MHz, CDCl$_3$) $\delta$ (TMS): 8.26 (m, 2H, Ar), 7.79 (d, J=7.4 Hz, 1H, Ar), 7.23 (m, 1H, Ar), 6.9-6.4 (m, 2H, Ar), 4.90 (d, J=10.7 Hz, 1H, CHN), 4.07 (d, J=10.7 Hz, 1H, CHN), 1.65 (broad s, H$_2$O+OH), 1.44 (s, 3H, CH$_3$), 1.27 (s, 3H, CH$_3$).

Analysis Calcd. for C$_{18}$H$_{15}$N$_3$O$_5$. 0.75 H$_2$O: C 58.94%; H 4.50%; N 11.46%. Found: C 58.89%; H 4.50%; N 11.63%.

EXAMPLE 28

Trans 2,2-dimethyl-3hydroxy-1-oxo-4-(2-oxo-1-pyrrolidinyl)-1,2,3,4-tetrahydronaphthalen-6-carbonitrile Following the procedure described in example 2, but starting from the product obtained in preparation 23, the title compound of this example was obtained as a white solid (yield: 63%).

M.p.: 268.5° C.;

IR (KBr) $\nu$: 3500–3200, 2970, 2916, 2233, 1691, 1641, 1431, 1290, 1276, 1071 cm$^{-1}$;

$^1$H NMR (80 MHz, CDCl$_3$) $\delta$ (TMS): 8.17 (d, J=8 Hz, 1H, Ar), 7.70 (broad d, J=8 Hz, 1H, Ar), 7.49 (broad s, 1H, Ar), 5.41 (d, J=10.4 Hz, 1H, CHN), 3.86 (d, J=10.4 Hz, 1H, CHO), 3.6-3.0 (m, 2H, CH$_2$N), 3.20 (s, 1H, OH), 2.64 (m, 2H, CH$_2$CO), 2.18 (m, 2H, CH$_2$), 1.39 (s, 3H, CH$_3$), 1.19 (s, 3H, CH$_3$).

Analysis Calcd. for C$_{17}$H$_{18}$N$_2$O$_3$: C 68.44%; H 6.08%; N 9.39%. Found: C 68.19%; H 6.44%; N 8.40%.

EXAMPLE 29

Trans 3-acetoxy-2,2-dimethyl-1-oxo-4-(2-oxo-1-pyrrolidinyl)-1,2,3,4-tetrahydronaphthalen-6-carbonitrile Following the procedure described in example 10, but starting from the product obtained in example 28, the title compound of this example was obtained as a white solid (yield: 82%).

M.p.: 197.4°-201.9° C.;

IR (KBr) $\nu$: 2977, 2908, 2223, 1732, 1680, 1455, 1427, 1367, 1283, 1230, 1029, 979 cm$^{-1}$;

$^1$H NMR (80 MHz, CDCl$_3$) δ (TMS): 8.20 (d, J=8 Hz, 1H, Ar), 7.46 (s, 1H, Ar), 5.76 (d, J=10.4 Hz, 1H, CHN), 5.31 (d, J=10.4 Hz, 1H, CHO), 3.5–2.9 (m, 2H, CH$_2$N), 2.47 (m, 2H, CH$_2$CO), 2.14 (s, 3H, COCH$_3$), 2.04 (m, 2H, CH$_2$), 1.27 (broad s, 6H, 2CH$_3$).

Analysis Calcd. for C$_{19}$H$_{20}$N$_2$O$_4$: C 67.05%, H 5.92%; N 8.23%. Found: C 66.74%; H 6.17%; N 7.87%.

EXAMPLE 30

1,2-dihydro-2,2-dimethyl-4-(2-oxo-1-pyrrolidinyl)naphthalen-6-carbonitrile

Following the procedure described in example 26B, but starting from the product obtained in example 21, the title compound of this example was obtained as a white solid (yield: 83%)

M.p.: 144.0° C.;

IR (KBr) $\nu$: 3060, 2978, 2873, 2223, 1687, 1673, 1580, 1270, 1230 cm$^{-1}$;

$^1$H NMR (80 MHz, CDCl$_3$) δ (TMS): 7.90 (d, J=8 Hz, 1H, Ar), 7.35 (m, 2H, Ar), 5.30 (s, 1H, CH), 3.57 (m, 2H, CH$_2$N), 2.6–1.8 (complex signal, 4H), 1.34 (s, 3H, CH$_3$), 1.27 (s, 3H, CH$_3$).

Analysis Calcd. for C$_{17}$H$_{16}$N$_2$O$_2$: C 72.84%; H 5.75%; N 9.99%. Found: C 73.04%; H 5.90%; N 9.57%.

EXAMPLE 31

Trans 4-(2,3-dihydro-1-oxo-1H-isoindol-2-yl)-2,2-dimethyl-3-hydroxy-1-oxo-1,2,3,4-tetrahydronaphthalen-6-carbonitrile Following the procedure described in example 22, but starting from the product obtained in preparation 22, the title compound of this example was obtained as a white solid (yield: 33%).

M.p.: 198.1°-202.9° C.;

IR (KBr) $\nu$: 3600-3200, 3063, 2965, 2931, 2230, 1657, 1466, 1402, 1298, 1216, 1080, 946 cm$^{-1}$;

$^1$H NMR (80 MHz, CDCl$_3$) δ (TMS): 8.21 (d, J=8 Hz, 1H, Ar), 8.0–7.3 (complex signal, 6H, Ar), 5.68 (d, J=10.4 Hz, 1H, CHN), 4.9–4.1 (complex signal, 2H, CHO+OH), 3.08 (s, 2H, CH$_2$), 1.42 (s, 3H, CH$_3$), 1.26 (s, 3H, CH$_3$).

Analysis Calcd. for C$_{21}$H$_{18}$N$_2$O$_3$.0.75H$_2$O: C 70.10%; H 5.42%; N 7.78%. Found: C 69.80%; H 5.71%; N 7.27%.

EXAMPLE 32

1,2-dihydro-4-(2,3-dihydro-1-oxo-1H-isoindol-2-yl)-2,2-dimethyl-1-oxonaphthalen-6-carbonitrile Following the procedure described in example 6, but starting from the product obtained in example 31, the title compound of this example was obtained as a white solid (yield: 33%)

M.p.: 155.4°-167.8° C.;

IR (KBr) $\nu$: 2963, 2921, 2225, 1691, 1679, 1462, 1391, 1303, 1218, 985, 732 cm$^{-1}$;

$^1$H NMR (80 MHz, CDCl$_3$) δ (TMS): 8.21 (d, J=8 Hz, 1H, Ar), 7.98 (m, 1H, Ar), 7.7–7.2 (complex signal, 5H, Ar), 6.35 (s, 1H, CH), 4.74 (s, 2H, CH$_2$), 1.54 (s, 3H, CH$_3$), 1.43 (s, 3H, CH$_3$).

Analysis Calcd. for C$_{21}$H$_{16}$N$_2$O$_2$.0.25H$_2$O: C 75.79%; H 4.96%; N 8.42%. Found: C 75.80%; H 5.17%; N 8.37%.

EXAMPLE 33

Trans 4-(1,2-dihydro-2-oxo-1-pyridyl)-2,2-dimethyl-6-fluoro-3-hydroxy-1,2,3,4-tetrahydronaphthalen-1-one Following the procedure described in example 1, but starting from the product obtained in preparation 26, the title compound of this example was obtained as a white solid (yield: 26%).

M.p.: 254.4°-256.9° C.;

IR (KBr) $\nu$: 3600-3100, 2979, 2967, 2940, 1674, 1648, 1601, 1565, 1535, 1289, 1229, 1147, 1089 cm$^{-1}$;

$^1$H NMR (80 MHz, CDCl$_3$) δ (TMS): 8.15 (dd, J=8 Hz, J$_{HF}$=5.8 Hz, 1H, Ar), 7.6–6.3 (complex signal, 7H, Ar+CHN), 3.97 (d, J=10.4 Hz, 1H, CHO), 3.82 (s, 1H, OH), 1.54 (s, 3H, CH$_3$), 1.43 (s, 3H, CH$_3$).

Analysis Calcd. for C$_{17}$H$_{16}$FNO$_3$: C 67.76%; H 5.35%; N 4.65%. Found: C 67.69%; H 5.40%; N 4.66%.

EXAMPLE 34

1,2-dihydro-4-(1,2-dihydro-2-oxo-1-pyridyl)-2,2-dimethyl-6-fluoronaphthalen-1-one Following the procedure described in example 6, but starting from the product obtained in example 33, the title compound of this example was obtained as a white solid (yield: 72%).

M.p.: 174.8°-178° C.;

IR (BKr) $\nu$: 3062, 2955, 2921, 1665, 1584, 1524, 1344, 1230, 993 cm$^{-1}$;

$^1$H NMR (80 MHz, CDCl$_3$) δ (TMS): 8.16 (dd, J=8.8 Hz, 1H, Ar), 7.6–6.3 (complex signal, 6H, Ar), 6.26 (s, 1H, CH), 1.45 (s, 3H, CH$_3$), 1.38 (s, 3H, CH$_3$).

Analysis Calcd. for C$_{17}$H$_{14}$FNO$_2$: C 72.07%; H 4.98%; N 4.94%. Found: C 71.86%; H 4.98%; N 4.94%.

EXAMPLE 35

Trans 2,2-dimethyl-6-fluoro-3-hydroxy-4-(2-oxo-1-pyrrolidinyl)-1,2,3,4-tetrahydronaphthalen-1-one Following the procedure described in example 2, but starting from the product obtained in preparation 28, the title compound of this example was obtained as a white solid (yield: 34%).

M.p.: 237.8° C.;

IR (KBr) $\nu$: 3500-3100, 2971, 2920, 1649, 1601, 1462, 1418, 1286, 1261, 1084, 1071 cm$^{-1}$;

$^1$H NMR (80 MHz, CDCl$_3$) δ (TMS): 8.12 (dd, J=8.8 Hz, J$_{HF}$=5.9 Hz, 1H, Ar), 6.99 (m, 2H, Ar), 5.50 (d, J=10.5, 1H, CHN), 3.87 (d, J=10.5 Hz, 1H, CHO), 3.30 (m, 2H, CH$_2$N), 2.7–1.9 (complex signal, 5H, CH$_2$CO+CH$_2$+OH), 1.38 (s, 3H, CH$_3$), 1.19 (s, 3H, CH$_3$).

Analysis Calcd. for C$_{16}$H$_{18}$FNO$_3$.1H$_2$O: C 62.13%; H 6.47%; N 4.53%. Found: C 61.98%; H 6.62%; N 4.49%.

EXAMPLE 36

Trans 4-(1,2-dihydro-2-oxo-1-pyridyl)-2,2-dimethyl-3-hydroxy-6-N-methylacetamide-1,2,3,4-tetrahydronaphthalen-1-one Following the procedure described in example 1, but starting from the product obtained in preparation 31, the title compound of this example was obtained as a white solid (yield: 55%).

M.p.: 89.3°–104.1° C.;

IR (BKr) $v$: 3600–3000, 2966, 2929, 1649, 1596, 1530, 1372, 1281, 1145, 1080, 980 cm$^{-1}$;

$^1$H NMR (80 MHz, CDCl$_3$) $\delta$ (TMS): 8.17 (d, J=8 Hz, 1H, Ar), 7.34 (m, 3H, Ar), 7.01 (dd, J=6.9 Hz, J=1.8 Hz, 1H, Ar), 6.70 (m, 2H, Ar+CHN), 6.26 (t, J=5.6 Hz, 1H, Ar), 3.98 (d, J=10.5 Hz, 1H, CHO), 3.22 (s, 3H, CH$_3$N), 2.79 (broad s, OH), 1.89 (s, 3H, CH$_3$CO), 1.41 (s, 3H, CH$_3$), 1.28 (s, 3H, CH$_3$).

Analysis Calcd. for C$_{20}$H$_{22}$N$_2$O$_4$.H$_2$O: C 64.50%; H 6.50%; N 7.52%. Found: C 64.49%; H 6.19%; N 7.73%.

EXAMPLE 37

Trans 3-acetoxy-4-(1,2-dihydro-2-oxo-1-pyridyl)-2,2-dimethyl-6-N-methylacetamido-1,2,3,4-tetrahydronaphthalen-1-one Following the procedure described in example 10, but starting from the product obtained in example 36, the title compound of this example was obtained as a white solid (yield: 84%).

M.p.: °C.;

IR (KBr) $v$: 3018, 2973, 2929, 1738, 1656, 1583, 1529, 1370, 1221, 1142, 1037 cm$^{-1}$;

$^1$H NMR (80 MHz, CDCl$_3$) $\delta$ (TMS): 8.19 (d, J=8 Hz, 1H, Ar), 7.5–6.6 (complex signal, 6H, Ar+CHN), 6.21 (t, J=6.8 Hz, 1H, Ar), 5.52 (d, J=11.2 Hz, 1H, CHO), 3.22 (s, 3H, CH$_3$N), 2.00 (s, 3H, CH$_3$CO), 1.88(s, 3H, CH$_3$CON), 1.37 (s, 3H, CH$_3$), 1.29 (s, 3H, CH$_3$).

EXAMPLE 38

1,2-dihydro-4-(1,2-dihydro-2-oxo-1-pyridyl)-2,2-dimethyl-6-N-methylacetamidonaphthalen-1-one Following the procedure described in example 11, but starting from the product obtained in example 37, the title compound of this example was obtained as a white solid (yield: 85%).

M.p.: 159.7°–160.0° C.;

IR (KBr) $v$: 3054, 3015, 2960, 1656, 1582, 1527, 1376, 1143, 784 cm$^{-1}$;

$^1$H NMR (80 MHz, CDCl$_3$) $\delta$ (TMS): 8.18 (d, J=8 Hz, 1H, Ar), 7.50 (dd, J=6.6 Hz, J=2.2 Hz, 1H, Ar), 7.24 (m, 2H, Ar), 6.65 (m, 2H, Ar), 6.29 (d of t, J=8 Hz, J=2.9 Hz, 1H, Ar), 6.26 (s, 1H, CH), 3.24 (s, 3H, CH$_3$N), 1.94 (s, 3H, CH$_3$CO), 1.46 (s, 3H, CH$_3$), 1.41 (s, 3H, CH$_3$).

Analysis Calcd. for C$_{20}$H$_{20}$N$_2$O$_3$.0.25H$_2$O: C 70.48%; H 6.02%; N 8.22%. Found: C 70.69%; H 6.01%; N 8.50%.

EXAMPLE 39

Trans 2,2-dimethyl-3-hydroxy-6-N-methylacetamido-4-(2-oxo-1-pyrrolidinyl)-1,2,3,4-tetrahydronaphthalen-1-one Following the procedure described in example 2, but starting from the product obtained in preparation 33, the title compound of this example was obtained as a white solid (yield: 44%).

M.p.: 189.9°–201.0° C.;

IR (KBr) $v$: 3600–3100, 2965, 2925, 1658, 1596, 1416, 1372, 1286, 1080 cm$^{-1}$;

$^1$H NMR (80 MHz, CDCl$_3$) $\delta$ (TMS): 8.14 (d, J=8 Hz, 1H, Ar), 7.27 (m, 1H, Ar), 7.01 (s, 1H, Ar), 5.51 (d, J=10.4 Hz, 1H, CHN), 3.90 (d, J=10.4 Hz, 1H, CHO), 3.30 (m, 2H, CH$_2$N), 3.30 (s, 3H, CH$_3$N), 2.63 (m, 2H, CH$_2$CO), 2.15 (m, 3H, CH$_2$+OH), 1.98 (s, 3H, CH$_3$CO), 1.39 (s, 3H, CH$_3$), 1.21 (s, 3H, CH$_3$).

EXAMPLE 40

1,2-dihydro-2,2-dimethyl-6-N-methylacetamido-4-(2-oxo-1-pyrrolidinyl)naphthalen-1-one Following the procedure described in example 6, but starting from the product obtained in example 39, the title compound of this example was obtained as a white solid (yield: 83%).

M.p.: 149.1°–155.0° C.;

IR (KBr) $v$: 2961, 2921, 1658, 1591, 1405, 1374, 1297, 983 cm$^{-1}$;

$^1$H NMR (80 MHz, CDCl$_3$) $\delta$ (TMS): 8.14 (d, J=8 Hz, 1H, Ar), 7.22 (m, 1H, Ar), 6.94 (d, J=1.9 Hz, 1H, Ar), 6.14 (s, 1H, CH), 3.71 (t, J=6.9 Hz, 2H, CH$_2$N), 3.30 (s, 3H, CH$_3$N), 2.7–2.1 (complex signal, 4H, CH$_2$CO+CH$_2$), 1.99 (s, 3H, CH$_3$CO), 1.36 (s, 6H, 2CH$_3$).

Analysis Calcd. for C$_{19}$H$_{22}$N$_2$O$_3$.0.5H$_2$O: C68.06%; H 6.87%; N 8.36%. Found: C 68.06%; H 6.93%; N 7.87%.

EXAMPLE 41

Trans 4-(1,2-dihydro-2-oxo-1-pyridyl)-2,2-dimethyl-3-hydroxy-1,2,3,4-tetrahydro-6-trifluoromethylnaphthalen-1-one Following the procedure described in example 14B, but starting from the product obtained in preparation 36, the title compound of this example was obtained as a white solid (yield: 44%)

M.p.: 202.3°–205.6° C.;

IR (KBr) $v$: 3600–3200, 2973, 2973, 1686, 1653, 1577, 1531, 1417, 1331, 1169, 1130, 1076 cm$^{-1}$;

$^1$H NMR (80 MHz, CDCl$_3$) $\delta$ (TMS): 8.25 (d, J=8.2 Hz, 1H, Ar), 7.8–6.6 (complex signal, 6H, Ar+CHN), 6.29 (m, 1H, Ar), 4.98 (d, J=10.3 Hz, 1H, CHO), 1.83 (broad s, OH), 1.42 (s, 3H, CH$_3$), 1.27 (s, 3H, CH$_3$).

Analysis Calcd. for C$_{18}$H$_{16}$F$_3$NO$_3$: C 61.54%; H 4.59%; N 3.99%. Found: C 61.55%; H 4.54%; N3.95%.

EXAMPLE 42

1,2-dihydro-4-(1,2-dihydro-2-oxo-1-pyridyl)-2,2-dimethyl-6-trifluoromethylnaphthalen-1-one Following the procedure described in example 6, but starting from the product obtained in example 41, the title compound of this example was obtained as a white solid (yield: 81%).

M.p.: 130.1° C.;

IR (KBr) $v$: 3042, 2965, 1670, 1588, 1530, 1353, 1307, 1165, 1154, 1124, 1074 cm$^{-1}$;

$^1$H NMR (80 MHz, CDCl$_3$) $\delta$ (TMS): 8.25 (d, J=8 Hz, 1H, Ar), 7.67 (d, J=8 Hz, 1H, Ar), 7.45 (m, 1H, Ar), 7.20 (m, 2H, Ar), 6.69 (d, J=9.3 Hz, 1H, Ar), 6.29 (m, 1H, Ar), 6.29 (s, 1H, CH), 1.47 (s, 3H, CH$_3$), 1.41 (s, 3H, CH$_3$).

Analysis Calcd. for $C_{18}H_{14}F_3NO_2$: C 64.86%; H 4.23%; N 4.20%. Found: C 65.08%; H 3.88%; N 4.25%.

EXAMPLE 43

Methyl 1,2-dihydro-4-(1,2-dihydro-2-oxo-1-pyridyl)-2,2-dimethyl-1-oxonaphthalen-6-carboximidate To a solution of 0.290 g (1 mmol), of the product obtained in example 26 in 2 mL of methanol, were added under argon atmosphere 0.020 g (0.38 mmol) of sodium methoxide, and the mixture was stirred overnight at room temperature. A drop of acetic acid was added to the solution and then the mixture was poured into 5 mL of water and extracted with ethyl acetate. The solution was dried over $MgSO_4$ and solvent was removed, affording a crude that was chromatographed on silica gel using hexane-ethyl acetate mixtures of increasing polarity as eluent. 0.130 g of the title compound of this example were obtained as a white solid (yield: 37%), together with 0.150 g of the starting product.

M.p.: 181.8°–190.2° C.;

IR (KBr) $\nu$: 3293, 2948, 2921, 1658, 1581, 1524,. 1439, 1314, 1229, 1070 cm$^{-1}$;

$^1$H NMR (80 MHz, CDCl$_3$) $\delta$ (TMS): 8.17 (d, J=8 Hz, 1H, Ar) 7.77 (d, J=8 Hz, 1H, Ar), 7.50 (m, 1H, Ar), 7.22 (m, 2H, Ar), 6.68 (d, J=8.8 Hz, 1H, Ar), 6.30 (m, 1H, Ar), 6.24 (s, 1H, CH), 3.87 (s, 3H, CH$_3$O), 1.46 (s, 3H, CH$_3$), 1.39 (s, 3H, CH$_3$).

Analysis Calcd. for $C_{19}H_{18}N_2O_3.0.5H_2O$: C 68.88%; H 5.74%; N 8.46%. Found: C 69.02%; H 5.70%; N 8.04%.

EXAMPLE 44

1,2-dihydro-4-(1,2-dihydro-2-oxo-1-pyridyl)-2,2-dimethyl-1-oxonaphthalen-6-carboxylic acid To 0.250 g (0.86 mmol) of the product obtained in example 26 were added 2 mL of 6N hydrochloric acid and the mixture was stirred overnight at reflux. 5 mL of water were added and the mixture was extracted with methylene chloride. The organic phase was extracted with NaOH 1N and the aqueous phase was acidified and extracted with methylene chloride. The solution was dried over $MgSO_4$ and the solvent was removed, affording 0.140 g of the title compound of this example as a white solid (yield: 53%).

M.p.: 274.8°–280.9° C.;

IR (KBr) $\nu$: 3600–2400, 1712, 1679, 1642, 1529, 1295, 1264, 1207, 1152, 991, 761 cm$^{-1}$;

$^1$H NMR (80 MHz, CDCl$_3$) $\delta$ (TMS): 8.08 (m, 2H, Ar), 7.52 (m, 2H, Ar), 7.30 (m, 1H, Ar), 6.77 (d, J=9.3 Hz, 1H, Ar), 6.39 (m, 1H, Ar), 6.24 (s, 1H, CH), 4.33 (broad s, H$_2$O+OH), 1.46 (s, 3H, CH$_3$), 1.40 (s, 3H, CH$_3$).

Analysis Calcd. for $C_{18}H_{15}NO_4.0.75H_2O$: C 66.98%; H 5.12%; N 4.34%. Found: C 66.89%; H 5.09%; N 4.53%.

EXAMPLE 45

1,2-dihydro-4-(1,2-dihydro-2-oxo-1-pyridyl)-2,2-dimethyl-1-oxonaphthalen-6-carboxamide To a suspension of 0.48 g (8.5 mmol) of KOH in 4 mL of tert-butyl alcohol, were added 0.250 g (0.86 mmol) of the product obtained in example 26 and the mixture was stirred for 1 h under reflux. The solvent was removed and 5 mL of water were added to the residue. The mixture was extracted with ethyl acetate. The solution was dried over $MgSO_4$ and the solvent was removed, affording 0.138 g of the title compound of this example as a white solid (yield: 52%).

M.p.: 168.3° C.;

IR (KBr) $\nu$: 3302, 3162, 2963, 1671, 1643, 1566, 1529, 1426, 1342, 1224, 1145, 989, 769 cm$^{-1}$;

$^1$H NMR (80 MHz, CDCl$_3$) $\delta$ (TMS): 8.11 (d, J=8 Hz, 1H, Ar), 7.76 (dd, J=8 Hz, J=1.3 Hz, 1H, Ar), 7.54 (ddd, J=9.2 Hz, J=6.6 Hz, J=2.0 Hz, 1H, Ar), 7.26 (m, 1H, Ar), 7.11 (s, 1H, Ar), 6.62 (d, J=9.2 Hz, 1H, Ar), 6.37 (t, J=6.6 Hz, 1H, Ar). 6.19 (s, 1H, CH), 3.11 (s, NH$_2$), 1.39 (s, 3H, CH$_3$), 1.33 (s, 3H, CH$_3$).

Analysis Calcd. for $C_{18}H_{16}N_2O_3.0.5H_2O$: C 68.14%; H 5.36%; N 8.83%. Found C 67.96%; H 5.58%; N 8.45%.

EXAMPLE 46

Methyl 1,2-dihydro-4-(1,2-dihydro-2-oxo-1-pyridyl)-2,2-dimethyl-1-oxonaphthalen-6-carboxylate HCl gas was passed through a boiling solution of 0.75 g (2.6 mmol) of the product obtained in example 26 in 7 mL of methanol during 4.5 h and the mixture was left to stand overnight. The solvent was removed and 5 mL of water were added to the residue. The mixture was extracted with chloroform and the solution was dried over $MgSO_4$. The solvent was removed, affording a crude that was chromatographed on silica gel using hexane-ethyl acetate mixtures of increasing polarity as eluent. 0.360 g of the title compound of this example were obtained as a white solid (yield: 43%).

M.p.: 187.9°–189.2° C.;

IR (KBr) $\nu$: 2955, 1719, 1659, 1585, 1524, 1433, 1298, 1274, 1233, 1156, 995, 756 cm$^{-1}$;

$^1$H NMR (80 MHz, CDCl$_3$) $\delta$ (TMS): 8.12 (m, 2H, Ar), 7.41 (m, 2H, Ar), 7.23 (m, 1H, Ar), 6.68 (d, J=9.2 Hz, 1H, Ar), 6.29 (m, 1H, Ar), 6.23 (s, 1H, CH), 3.88 (s, 3H, CH$_3$O), 1.46 (s, 3H, CH$_3$), 1.39 (s, 3H, CH$_3$).

Analysis Calcd. for $C_{19}H_{17}NO_4.0.5H_2O$: C 68.67%; H 5.42%; N 4.22%. Found: C 68.78%; H 5.35%; N 4.53%.

EXAMPLE 47

1,2-dihydro-4-(1,2-dihydro-2-oxo-1-pyridyl)-2,2-dimethyl-6-methylaminonaphthalen-1-one A solution of 0.15 g (1.5 mmol) of the product obtained in example 38 in 3 mL of 6N hydrochloric acid was heated under reflux for 2 hours. The mixture was allowed to cool and was poured into 4N NaOH and extracted with ethyl acetate. The solution was dried over $MgSO_4$ and the solvent was removed, affording 0.490 g of a crude that was recrystallized from ethyl acetate. 0.250 g of the title compound of this example were obtained as a white solid (yield: 56%).

M.p.: 115.5°–120.0° C.;

IR (KBr) $\nu$: 3297, 3063, 2960, 2923, 1649, 1572, 1525, 1376, 1282, 1245, 1156 cm$^{-1}$;

$^1$H NMR (80 MHz, CDCl$_3$) $\delta$ (TMS): 8.01 (d, J=8.6 Hz, 1H, Ar), 7.46 (ddd, J=9.2 Hz, J=6.8 Hz, J=1.8 Hz, 1H, Ar), 7.26 (m, 2H, Ar), 6.7–6.2 (complex signal, 3H, Ar), 6.15 (s, 1H, CH), 5.85 (d, J=2.2 Hz, 1H, NH), 2.74 (s, 3H, CH$_3$N), 1.40 (s, 3H, CH$_3$), 1.34 (s, 3H, CH$_3$).

Analysis Calcd. for $C_{18}H_{18}N_2O_2.0.25H_2O$: C 72.36%; H 6.20%; N 9.38%. Found: C 72.03%; H 6.39%; N 9.33%.

EXAMPLE 48

1,2-dihydro-4-(1,2-dihydro-2-oxo-1-pyridyl)-2,2-dimethyl-6-N-methylmethanesulphonamidenaphthalen-1-one To a solution of 0.2 g (0.85 mmol) of the product obtained in example 47 in 11 mL of a 1:1 mixture chloroform/pyridine, were added at 0° C. and under argon atmosphere 0.211 g (0.85 mmol) of methanesulphonyl chloride and the mixture was stirred overnight at room temperature. The solution was poured into water and the aqueous phase was extracted with methylene chloride. The combined organic phases were washed with 1N hydrochloric acid and dried over $MgSO_4$. The solvent was removed, affording a crude that was chromatographed on silica gel using ethyl acetate as eluent. 0.150 g of the title compound of this example were obtained as a white solid (yield: 59%).

M.p.: 125.2° C.;

IR (KBr) $\nu$: 2961, 2921, 1658, 1589, 1527, 1339, 1279, 1152 cm$^{-1}$;

$^1$H NMR (80 MHz, CDCl$_3$) $\delta$ (TMS): 8.15 (d, J=8.7 Hz, 1H, Ar), 7.50 (m, 2H, Ar), 7.26 (m, 1H, Ar), 6.91 (m, 1H, Ar), 6.68 (d, J=9.3 Hz, 1H, Ar), 6.30 (m, 1H, Ar), 6.24 (s, 1H, CH), 3.29 (s, 3H, CH$_3$N), 2.85 (s, 3H, CH$_3$SO$_2$), 1.45 (s, 3H, CH$_3$), 1.39 (s, 3H, CH$_3$).

Analysis Calcd. for C$_{19}$H$_{20}$N$_2$SO$_4$.0.25H$_2$O: C 61.27%; H 5.41%; N 7.52%. Found: C 61.37%; H 6.11%; N 7.24%.

EXAMPLE 49

1,2-dihydro-4-(1,2-dihydro-2-oxo-1-pyridyl)-2,2-dimethyl-6-trimethylsilylethynylnaphthalen-1-one To a solution of 1 g (2.9 mmol) of the product obtained in example 16 in 6.5 mL of deaerated, anhydrous triethylamine were added, under argon atmosphere, 0.022 g (0.084 mmol) of triphenylphosphine, 0.0009 g (0.035 mmol) of palladium (II) acetate and 0.65 mL (4.5 mmol) of ethynyltrimethylsilane, and the mixture was stirred overnight at reflux. The precipitated triethylamine hydrobromide was filtered and the brown filtrate was concentrated. The residue was mixed with aqueous sodium bicarbonate and extracted with methylene chloride. The solution was poured into water and the aqueous phase extracted with methylene chloride. The combined organic phases were dried over MgSO$_4$ and the solvent was removed, affording a crude that was chromatographed on silica gel using ethyl acetate as eluent. 0.950 g of the title compound of this example were obtained as a white solid (yield: 90%).

M.p.: 84.3°-94.0° C.;

IR (KBr) $\nu$: 2957, 2921, 2154, 1666, 1589, 1528, 1346, 1247, 1226, 906, 845, 760 cm$^{-1}$;

$^1$H NMR (80 MHz, CDCl$_3$) $\delta$ (TMS): 8.07 (d, J=8 Hz, 1H, Ar), 7.53 (m, 2H, Ar), 7.23 (m, 1H, Ar), 6.91 (d, J=1.2 Hz, 1H, Ar), 6.70 (d, J=9.3 Hz, 1H, Ar), 6.31 (d of t, J=5.7 Hz, J=1.6 Hz, 1H, Ar), 6.20 (s, 1H, CH), 1.45 (s, 3H, CH$_3$), 1.38 (s, 3H, CH$_3$), 0.23 (s, 9H, (CH$_3$)$_3$Si).

Analysis Calcd. for C$_{22}$H$_{23}$NSiO$_2$.0.5H$_2$O: C 71.35%; H 6.49%; N 3.78%. Found: C 71.69%; H 6.75%; N 3.88%.

EXAMPLE 50

1,2-dihydro-4-(1,2-dihydro-2-oxo-1-pyridyl)-2,2-dimethyl-6-ethynylnaphthalen-1-one To a solution of 0.68 g (1.9 mmol) of the product obtained in example 49 in 5 mL of methanol were added, under argon atmosphere, 0.024 g (0.17 mmol) of potassium carbonate and the mixture was stirred for 3 h at room temperature. The solution was concentrated and the residue was treated with aqueous sodium bicarbonate and extracted with methylene chloride. The solution was poured into water and the aqueous phase extracted with methylene chloride. The combined organic phases were dried over MgSO$_4$ and the solvent was removed, affording a crude that was chromatographed on silica gel/triethylamine using hexane-ethyl acetate mixtures as eluent. 0.405 g of the title compound of this example were obtained as a white solid (yield: 74%).

M.p.: 166.8°-169.0° C.;

IR (KBr) $\nu$: 3136, 2959, 2096, 1658, 1583, 1528, 1346, 1263, 1225, 988 cm$^{-1}$;

$^1$H NMR (80 MHz, CDCl$_3$) $\delta$ (TMS): 8.09 (d, J=8 Hz, 1H, Ar), 7.47 (m, 2H, Ar), 7.23 (m, 1H, Ar), 6.95 (s, 1H, Ar), 6.68 (d, J=9.1 Hz, 1H, Ar), 6.29 (t, J=6.8 Hz, 1H, Ar), 6.22 (s, 1H, CH), 3.22 (s, 1H, HC C), 1.45 (s, 3H, CH$_3$), 1.38 (s, 3H, CH$_3$).

Analysis Calcd. for C$_{19}$H$_{15}$NO$_2$: C 78.87%; H 5.23%; N 4.84%. Found: C 78.46%; H 5.38%; N 4.82%.

EXAMPLE 51

Trans 7-bromo-4-(1,2-dihydro-2-oxo-1-pyridyl)-2,2-dimethyl-3-hydroxy-1,2,3,4-tetrahydronaphthalen-1-one Following the procedure described in example 1, but starting from the product obtained in preparation 39, the title compound of this example was obtained as a white solid (yield: 50%)

M.p.: 191.5°-192.5° C.;

IR (KBr) $\nu$: 3600-3100, 2965, 2925, 1683, 1643, 1565, 1530, 1461, 1396, 1261, 1175, 905, 769 cm$^{-1}$;

$^1$H NMR (80 MHz, CDCl$_3$) $\delta$ (TMS): 8.22 (d, J=2.0 Hz, 1H, Ar), 7.65 (dd, J=8.4 Hz, J=2.0 Hz, 1H, Ar), 7.37 (m, 2H, Ar), 7.0–6.2 (complex signal, 4H, Ar+CHN), 3.94 (d, J=8.6 Hz, 1H, CHO), 2.54 (broad s, 1H, OH), 1.44 (s, 3H, CH$_3$), 1.24 (s, 3H, CH$_3$).

Analysis Calcd. for C$_{17}$H$_{16}$BrNO$_3$: C 56.37%; H 4.45%; N 3.87%. Found: C 56.16%; H 4.57%; N 3.72%.

EXAMPLE 52

7-bromo-1,2-dihydro-4-(1,2-dihydro-2-oxo-1-pyridyl)-2,2-dimethylnaphthalen-1-one Following the procedure described in example 6, but starting from the product obtained in example 51, the title compound of this example was obtained as a white solid (yield: 71%).

M.p.: 193.8° C.;

IR (KBr) $\nu$: 3061, 2963, 1678, 1649, 1580, 1529, 1474, 1272, 1140, 836, 764 cm$^{-1}$;

$^1$H NMR (80 MHz, CDCl$_3$) $\delta$ (TMS): 8.23 (d, J=2.1 Hz, 1H, Ar), 7.65 (dd, J=8.4 Hz, J=2.1 Hz, 1H, Ar), 7.5–7.1 (m, 2H, Ar), 6.70 (m, 2H, Ar), 6.28 (m, 1H, Ar), 6.21 (s, 1H, CH), 1.44 (s, 3H, CH$_3$), 1.38 (s, 3H, CH$_3$).

Analysis Calcd. for C$_{17}$H$_{14}$BrNO$_2$.0.25H$_2$O: C 58.54%; H 4.16%; N 4.02%. Found: C 58.86%; H 4.24%; N 3.97%.

EXAMPLE 53

Trans
7-bromo-2,2-dimethyl-3-hydroxy-4-(2-oxo-1-pyrrolidinyl)-1,2,3,4-tetrahydronaphthalen-1-one Following the procedure described in example 2, but starting from the product obtained in preparation 41, the title compound of this example was obtained as a white solid (yield: 34%).

M.p.: 193.7°–193.8° C.;

IR (KBr) $\nu$: 3600–3000, 2960, 2923, 1685, 1648, 1431, 1289, 1174, 1070 cm$^{-1}$;

$^1$H NMR (80 MHz, CDCl$_3$) $\delta$ (TMS): 8.17 (d, J=2.1 Hz, 1H, Ar), 7.70 (dd, J=8.3 Hz, J=2.1 Hz, 1H, Ar), 7.05 (d, J=8.3 Hz, 1H, Ar), 5.38 (d, J=10.5 Hz, 1H, CHAr), 3.81 (d, J=10.5 Hz, 1H, CHO), 3.65 (s, OH), 3.5–3.1 (m, 2H, CH$_2$N), 2.56 (m, 2H, CH$_2$CO), 2.16 (m, 2H, CH$_2$), 1.36 (s, 3H, CH$_3$), 1.18 (s, 3H, CH$_3$).

Analysis Calcd. for C$_{16}$H$_{18}$BrNO$_3$: C 54.56%; H 5.15%; N 3.98%. Found: C 55.06%; H 5.21%; N 4.01%.

EXAMPLE 54

7-bromo-1,2-dihydro-2,2-dimethyl-4-(2-oxo-1-pyrrolidinyl)naphthalen-1-one

Following the procedure described in example 6, but starting from the product obtained in example 53, the title compound of this example was obtained as a white solid (yield: 79%).

M.p.: 152.7°–154.1° C.;

IR (KBr) $\nu$: 3053, 2965, 2876, 1679, 1641, 1580, 1474, 1407, 1291, 1211, 846 cm$^{-1}$;

$^1$H NMR (80 MHz, CDCl$_3$) $\delta$ (TMS): 8.19 (d, J=2.2 Hz, 1H, Ar), 7.69 (dd, J=8.3 Hz, J=2.2 Hz, 1H, Ar), 7.02 (d, J=8.3 Hz, 1H, Ar), 6.10 (s, 1H, CH), 3.68 (t, J=7 Hz, 2H, CH$_2$N), 2.56 (m, 2H, CH$_2$CO), 2.29 (m, 2H, CH$_2$), 1.34 (s, 6H, 2CH$_3$).

Analysis Calcd. for C$_{16}$H$_{16}$BrNO$_2$: C 57.50%; H 4.83%; N 4.19%. Found: C 58.10%; H 5.10%; N 4.07%.

EXAMPLE 55

1,2-dihydro-4-(1,2-dihydro-2-oxo-1-pyridyl)-2,2-dimethyl-1-oxonaphthalen-7-carbonitrile Following the procedure described in example 26B, but starting from the product obtained in example 51, the title compound of this example was obtained as a white solid (yield: 62%).

M.p.: 206.8°–209.6° C.;

IR (KBr) $\nu$: 3069, 3037, 2962, 2225, 1680, 1649, 1580, 1529, 1277, 1152, 1138, 768 cm$^{-1}$;

$^1$H NMR (80 MHz, CDCl$_3$) $\delta$ (TMS): 8.39 (d, J=1.6 Hz, 1H, Ar), 7.79 (dd, J=8.2 Hz, J=1.6 Hz, 1H, Ar), 7.51 (ddd, J=9.2 Hz, J=6.5 Hz, J=2.0 Hz, 1H, Ar), 7.23 (dd, J=6.5 Hz, J=2.0 Hz, 1H, Ar), 7.00 (d, J=8.2 Hz, 1H, Ar), 6.67 (d, J=9.2 Hz, 1H, Ar), 6.37 (s, 1H, CH), 6.33 (t, J=6.5 Hz, 1H, Ar), 1.48 (s, 3H, CH$_3$), 1.42 (s, 3H, CH$_3$).

Analysis Calcd. for C$_{18}$H$_{14}$N$_2$O$_2$: C 74.47%; H 4.86%; N 9.65%. Found: C 74.53%; H 5.21%; N 9.41%.

EXAMPLE 56

1,2-dihydro-2,2-dimethyl-3-hydroxy-1-oxo-4-(2-oxo-1-pyrrolidinyl)naphthalen-7-carbonitrile Following the procedure described in example 26B, but starting from the product obtained in example 53, the title compound of this example was obtained as a white solid (yield: 46%).

M.p.: 95.1°–100.6° C.;

IR (KBr) $\nu$: 2961, 2921, 2221, 1685, 1642, 1598, 1406, 1297, 1242, 1157, 847 cm$^{-1}$;

$^1$H NMR (80 MHz, CDCl$_3$) $\delta$ (TMS): 8.34 (d, J=1.7 Hz, 1H, Ar), 7.83 (dd, J=8.1 Hz, J=1.7 Hz, 1H, Ar), 7.26 (d, J=8.1 Hz, 1H, Ar), 6.25 (s, 1H, CH), 3.70 (t, J=6.9 Hz, 2H, CH$_2$N), 2.58 (m, 2H, CH$_2$CO), 2.32 (m, 2H, CH$_2$), 1.37 (s, 6H, 2CH$_3$).

Analysis Calcd. for C$_{17}$H$_{16}$N$_2$O$_2$.0.5 H$_2$O: C 70.59%; H 5.88%; N 9.69%. Found: C 70.73%; H 6.17%; N 9.07%.

EXAMPLE 57

Trans
6,7-dichloro-4-(1,2-dihydro-2-oxo-1-pyridyl)-2,2-dimethyl-3-hydroxy-1,2,3,4-tetrahydronaphthalen-1-one Following the procedure described in example 1, but starting from the product obtained in preparation 44, the title compound of this example was obtained as a white solid (yield: 20%).

M.p.: 190.3°–192.6° C.;

IR (KBr) $\nu$: 3600–3200, 3080, 2971, 2930, 1675, 1653, 1583, 1533, 1456, 1270, 1145, 1085 cm$^{-1}$;

$^1$H NMR (80 MHz, CDCl$_3$) $\delta$ (TMS): 8.17 (s, 1H, Ar), 7.40 (m, 1H, Ar), 6.99 (s, 1H, Ar), 6.96 (m, 1H, Ar), 6.67 (d, J=8.9 Hz, 1H, Ar), 6.62 (d, J=10.3 Hz, 1H, CHN), 6.29 (m, 1H, Ar), 3.89 (d, J=10.3 Hz, 1H, CHO), 2.62 (broad s, 1H, OH), 1.39 (s, 3H, CH$_3$), 1.24 (s, 3H, CH$_3$).

Analysis Calcd. for C$_{17}$H$_{15}$Cl$_2$NO$_3$.0.25H$_2$O: C 57.22%; H 4.35%; N 3.93%. Found: C 57.14%; H 4.26%; N 3.79%.

EXAMPLE 58

6,7-dichloro-1,2-dihydro-4-(1,2-dihydro-2-oxo-1-pyridyl)-2,2-dimethylnaphthalen-1-one Following the procedure described in example 6, but starting from the product obtained in example 57, the title compound of this example was obtained as a white solid (yield: 75%).

M.p.: 212.8°–212.9° C.;

IR (KBr) $\nu$: 3069, 2964, 2916, 1676, 1654, 1582, 1525, 1343, 1289, 1140, 762 cm$^{-1}$;

$^1$H NMR (80 MHz, CDCl$_3$) $\delta$ (TMS): 8.18 (s, 1H, Ar), 7.48 (ddd, J=9.3 Hz, J=5.6 Hz, J=2.0 Hz, 1H, Ar), 7.22 (m, 1H, Ar), 6.93 (s, 1H, Ar), 6.68 (d, J=9.3 Hz, 1H, Ar), 6.32 (m, 1H, Ar), 6.23 (s, 1H, CH), 1.45 (s, 3H, CH$_3$), 1.38 (s, 3H, CH$_3$).

Analysis Calcd. for C$_{17}$H$_{13}$Cl$_2$NO$_2$.0.25H$_2$O: C 60.26%; H 3.99%; N 4.13%. Found: C 60.06%; H 3.94%; N 4.01%.

EXAMPLE 59

1,2-dihydro-4-(1,2-dihydro-2-oxo-1-pyridyl)-2,2-dimethyl-6-ethylnaphthalen-1-one To a solution of 0.15 g (0.51 mol) of the product obtained in example 50 in 9 mL ethyl acetate, were added 0.03 g of 5% Pd/C and the mixture was hydrogenated at atmospheric pressure for 2 h. After filtration, the solvent was removed, affording 0.110 g of the title compound of this example as a white solid (yield: 74%).

M.p.: 51.2°–52.9° C.;

IR (KBr) $\nu$: 3442 (H2O), 2961, 2923, 2865, 1665, 1594, 1528, 1279, 1228, 1139, 990 cm$^{-1}$;

¹H NMR (80 MHz, CDCl₃) δ (TMS): 8.08 (d, J=8 Hz, 1H, Ar), 7.47 (m, 1H, Ar), 7.26 (m, 2H, Ar), 6.70 (d, J=9.4 Hz, 1H, Ar), 6.64 (s, 1H, Ar), 6.29 (t, J=6.7 Hz, 1H, Ar), 6.18 (s, 1H, CH), 2.64 (q, J=7.6 Hz, 2H, CH₂), 1.44 (s, 3H, CH₃), 1.38 (s, 3H, CH₃), 1.18 (t, J=7.6 Hz, 3H, CH₂$\underline{CH_3}$).

Analysis Calcd. for C₁₉H₁₉NO₂.0.5H₂O: C 75.50%; H 6.62%; N 4.64%. Found: C 75.89%; H 6.64%; N 4.61%.

EXAMPLE 60

Trans 4-(1,2-dihydro-2-oxo-1-pyridyl)-2,2-dimethyl-3-hydroxy-6-phenylsulphonyl-1,2,3,4-tetrahydronaphthalen-1-one Following the procedure described in example 14B, but starting from the product obtained in preparation 47, the title compound of this example was obtained as a white solid (yield: 43%).

M.p.: 102.9°-114.9° C.;

IR (KBr) ν: 3600–3000, 2965, 2925, 1649, 1575, 1529, 1303, 1148 cm⁻¹;

¹H NMR (80 MHz, CDCl₃) δ (TMS): 8.21 (d, J=7.8 Hz, 1H, Ar), 7.87 (m, 3H, Ar), 7.56 (m, 5H, Ar), 6.79 (m, 1H, Ar), 6.69 (d, J=10.3 Hz, 1H, CHN), 6.29 (m, 2H, Ar), 3.93 (d, J=10.3 Hz, 1H, CHO), 1.69 (broad s, OH), 1.38 (s, 6H, 2CH₃).

Analysis Calcd. for C₂₃H₂₁NO₅S.0.25H₂O: C 64.56%; H 5.03%; N 3.27%; S 7.48%. Found: C 64.38%; H 5.18%; N 3.12%; S 6.90%.

EXAMPLE 61

Trans 4-(1,2-dihydro-2-oxo-1-pyridyl)-2,2-dimethyl-3-hydroxy-6-pentafluoroethyl-1,2,3,4-tetrahydronaphtalen-1-one Following the procedure described in example 14B, but starting from the product obtained in preparation 50, the title compound of this example was obtained as a white solid (yield: 21%).

M.p.: 213°-227° C.;

IR (KBr) ν: 3600–3000, 2969, 2931, 1691, 1654, 1576, 1530, 1205, 1146, 1091, 1005 cm⁻¹;

¹H NMR (80 MHz, CDCl₃) δ (TMS): 8.26 (d, J=8.1 Hz, 1H, Ar), 7.8-6.7 (complex signal, 6H, Ar+CHN), 6.29 (m, 1H, Ar), 3.97 (d, J=10.3 Hz, 1H, CHO), 1.85 (broad s, OH), 1.41 (s, 3H, CH₃), 1.28 (s, 3H, CH₃).

Analysis Calcd. for C₁₉H₁₆F₅NO₃.0.25H₂O: C 56.23%; H 4.07%; N 3.45%. Found: C 56.18%; H 4.12%; N 3.53%.

EXAMPLE 62

1,2-dihydro-4-(1,2-dihydro-2-oxo-1-pyridyl)-2,2-dimethyl-6-pentafluoroethylnaphtalen-1-one Following the procedure described in example 6, but starting from the product obtained in example 61, the title compound of this example was obtained as a white solid (yield: 79%).

M.p.: 190.2° C.;

IR (KBr) ν: 3067, 3039, 2970, 1657, 1585, 1528, 1286, 1212, 1199, 1143 cm⁻¹;

¹H NMR (80 MHz, CDCl₃) δ (TMS): 8.25 (d, J=8.1 Hz, 1H, Ar), 7.66 (d, J=8.1 Hz, 1H, Ar), 7.47 (m, 1H, Ar), 7.23 (d, J=4.7 Hz, 1H, Ar), 7.04 (s, 1H, Ar), 6.69 (d, J=9.3 Hz, 1H, Ar), 6.30 (m, 1H, Ar), 6.30 (s, 1H, CH), 1.47 (s, 3H, CH₃), 1.41 (s, 3H, CH₃).

Analysis Calcd. for C₁₉H₁₄F₅NO₂: C 59.54%; H 3.68%; N 3.65%. Found: C 59.65%; H 3.79%; N 3.42%.

EXAMPLE 63

Trans 6-bromo-2,2-diethyl-4-(1,2-dihydro-2-oxo-1-pyridyl)-3-hydroxy-1,2,3,4-tetrahydronaphtalen-1-one Following the procedure described in example 14B, but starting from the product obtained in preparation 55, the title compound of this example was obtained as a white solid (yield: 3.5%).

IR (KBr) ν: 3600–3000, 2963, 2929, 1678, 1649, 1581, 1530, 1251, 1077 cm⁻¹;

¹H NMR (80 MHz, CDCl₃) δ (TMS): 7.98 (d, J=8.2 Hz, 1H, Ar), 7.57 (d, J=8.2 Hz, 1H, Ar), 7.36 (m, 1H, Ar), 7.1-6.6 (complex signal, 4H, Ar+CHN), 6.29 (m, 1H, Ar), 4.26 (d, J=10.4 Hz, 1H, CHO), 2.49 (broad s, OH), 2.4-1.5 (m, 4H, 2CH₂), 0.80 (t, J=10.2 Hz, 3H, CH₃), 0.71 (t, J=10.2 Hz, 3H, CH₃).

Analysis Calcd. for C₁₉H₂₀BrNO₃: C 58.47%; H 5.17%; N 3.59%. Found: C 58.15%; H 5.52%; N 3.24%.

EXAMPLE 64

6-bromo-2,2-diethyl-1,2-dihydro-4-(1,2-dihydro-2-oxo-1-pyridyl)naphtalen-1-one

Following the procedure described in example 1, but starting from the product obtained in preparation 55, the title compound of this example was obtained as a white solid (yield: 30%) together with a 12% of the product described in example 63.

M.p.: >300° C.;

IR (KBr) ν: 2957, 2926, 1665, 1577, 1524, 1276, 1151 cm⁻¹;

¹H NMR (80 MHz, CDCl₃) δ (TMS): 8.98 (d, J=8.2 Hz, 1H, Ar), 7.54 (d, J=8.2 Hz, 1H, Ar), 7.45 (m, 1H, Ar), 7.22 (m, 1H, Ar), 6.98 (d, J=1.7 Hz, 1H, Ar), 6.70 (d, J=9 Hz, 1H, Ar), 6.30 (t, J=6.7 Hz, 1H, Ar), 6.15 (s, 1H, CH), 2.05 (m, 2H, CH₂), 1.58 (m, 2H, CH₂), 0.85 (t, J=7.6 Hz, 3H, CH₃), 0.75 (t, J=7.6 Hz, 3H, CH₃).

Analysis Calcd. for C₁₉H₁₈BrNO₂.0.5H₂O: C 59.84%; H 4.99%; N 3.67%. Found: C 59.80%; H 5.01%; N 3.81%.

EXAMPLE 65

2,2-diethyl-1,2-dihydro-4-(1,2-dihydro-2-oxo-1-pyridyl)-1-oxonaphtalen-6-carbonitrile Following the procedure described in example 26B, but starting from the product obtained in example 64, the title compound of this example was obtained as a white solid (yield: 58%).

M.p.: 157.4° C.;

IR (KBr) ν: 2959, 2926, 2229, 1665, 1588, 1526, 1276, 1228, 1138 cm⁻¹;

¹H NMR (80 MHz, CDCl₃) δ (TMS): 8.21 (d, J=8 Hz, 1H, Ar), 7.68 (dd, J=8Hz, J=1.9 Hz, 1H, Ar), 7.49 (m, 1H, Ar), 7.22 (m, 2H, Ar), 6.72 (d, J=9.3 Hz, 1H, Ar), 6.35 (t, J=6.3 Hz, 1H, Ar), 6.25 (s, 1H, CH), 2.14 (m, 2H, CH₂), 1.66 (m, 2H, CH₂), 1.86 (t, J=7.5 Hz, 3H, CH₃), 0.77 (t, J=7.5 Hz, 3H, CH₃).

Analysis Calcd. for C₂₀H₁₈N₂O₂: C 75.45%; H 5.70%; N 8.80%. Found: C 75.34%; H 5.49%; N 8.76%.

We claim:

1. A compound of formula I:

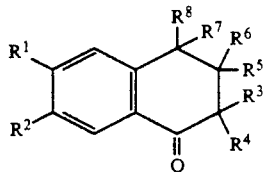

wherein:

R[1] and R[2] represent hydrogen, $C_{1-4}$ alkyl, hydroxyl, $C_{1-4}$ alkoxy, formyl, $C_{1-4}$ alkylcarbonyl, $C_{1-4}$ alkylthiocarbonyl, carboxyl, $C_{1-4}$ alkoxycarbonyl, $C_{1-4}$ alkoxythiocarbonyl, $C_{1-4}$ alkylcarbonyloxy, $C_{1-4}$ alkylthiocarbonyloxy, hydroxy-$(C_{1-4})$ alkyl, mercapto-$(C_{1-4})$ alkyl, perfluoro-$(C_{1-4})$alkyl, nitro, amino, cyano, halogen, trifluoromethoxy, ethynyl, trimethylsilylethynyl, $C_{1-4}$ alkylsulphinyl, arylsulphinyl, $C_{1-4}$ alkylsulphonyl, arylsulphonyl, $C_{1-4}$ alkoxysulphinyl, $C_{1-4}$ alkoxylsulphonyl, $C_{1-4}$ alkylcarbonylamino, $C_{1-4}$ alkoxycarbonylamino, aminosulphinyl, aminosulphonyl, aminocarbonyl, aminothiocarbonyl, $C_{1-4}$ alkylsulphinylamino, $C_{1-4}$ alkylsulphonylamino, $C_{1-4}$ alkoxylsulphinylamino, $C_{1-4}$ alkoxylsulphonylamino, $(C_{1-4}$ alkyl)carbonyl($C_{1-4}$ alkyl), nitro-$(C_{1-4}$ alkyl), cyano-$(C_{1-4}$ alkyl), $(C_{1-4}$ alkyl)C(=NOH), $(C_{1-4}$ alkyl)C(=NNH2) or $(C_{1-4}$ alkoxy)C(=NH), the above amino groups being optionally substituted by one or two $C_{1-4}$ alkyl groups;

R[3] is hydrogen or $C_{1-4}$ alkyl; R[4] is $C_{1-4}$ alkyl, or R[3] and R[4] together form a $C_{2-5}$ polymethylene chain;

either R[5] represents hydroxyl, acetoxy or formyloxy and R[6] and R[7] are both hydrogen; R[5] together with R[6] form a carbonyl group and R[7] is hydrogen; or R[5] and R[7] together form a bond and R[6] is hydrogen;

R[8] is 2,3-dihydro-1-oxo-1H-isoindol-2-yl being optionally substituted by a group R[9], or R[8] is 2-oxo-1-pyrrolidinyl or 2-thioxo-1-pyrrolidinyl, both of them being optionally substituted by a group R[10];

R[9] is a fluorine, chlorine, bromine or iodine atom or a $C_{1-4}$ alkyl, hydroxyl, nitro, or amino group, the amino group optionally substituted bu one or two $C_{1-4}$ alkyl groups;

R[10] is a $C_{1-4}$ alkyl, hydroxyl, $C_{1-4}$ hydroxyalkyl, $C_{1-4}$ alkoxymethyl, $C_{1-4}$ thioalkoxymethyl or aminomethyl group, the amino group optionally substituted by one or two $C_{1-4}$ alkyl groups;

or a salt thereof.

2. A compound according to claim 1 of formula Ia

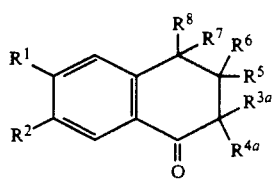

wherein R[1], R[2], R[5], R[6], R[7] and R[8] have the previously defined meaning; and R[3a] and R[4a] are methyl or ethyl.

3. A compound according to claim 1 of formula Ib

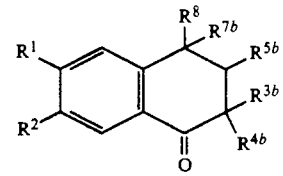

wherein R[1], R[2] and R[8] have the previously defined meaning; R[3b] and R[4b] are methyl or ethyl; and, either R[5b] represents hydroxyl and R[7b] an hydrogen atom, or R[5b] and R[7b] together form a bond.

4. A compound according to claim 1 of formula Ic

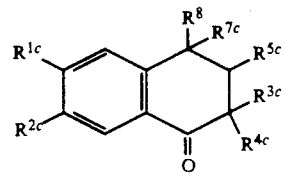

wherein R[8] has the previously defined meaning; R[3c], R[4c] R[5c] and R[7c] mean R[3a], R[4a], R[5b] and R[7b] respectively as previously defined in claim 2 or 3; R[1c] is halogen, cyano, $C_{1-4}$ alkyl, arylsulphonyl, trifluoromethyl, pentafluoroethyl, ethynyl, trimethylsilyethynyl or $C_{1-4}$ alkylcarbonylamino optionally substituted by a $C_{1-4}$ alkyl group; and R[2c] means hydrogen or R[1c].

5. A compound according to claim 1 of formula Id

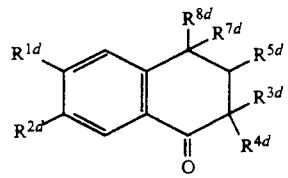

wherein R[1d], R[2d] R[3d], R[4d], R[5d] and R[7d] are R[1c], R[2c] R[3a], R[4a], R[5b] and R[7b] respectively as previously defined in claims 2, 3 or 4; and R[8d] means 2-oxo-1-pyrrolidinyl.

6. A compound according to claim 1 of formula Ie

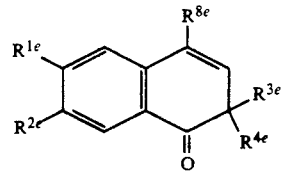

wherein R[1e], R[2e] R[3e], R[4e] and R[8e] mean R[1c], R[2c] R[3a] and R[8d] respectively as previously defined in claims 2, 3, 4 or 5.

7. A compound according to claim 1 of formula If

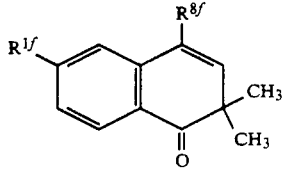

wherein R[1f] means R[1c] as defined in claim 4; and R[8f] means 2-oxo-1-pyrrolidinyl.

8. 1,2-dihydro-2,2-dimethyl-4-(2-oxo-1-pyrrolidinyl)-naphthalen-6-carbonitrile or a salt thereof.

9. A pharmaceutical composition comprising an effective amount of at least one compound of formula I as recited in claim 1, or a pharmaceutically acceptable salt thereof, in admixture with a pharmaceutically acceptable excipient.

10. A method for treating diseases related to the regulation of smooth muscle contraction at the cardiovascular, respiratory and cerebrovascular systems, and at the gastrointestinal, urinary and uterus tracts, and particularly for treating hypertension and asthma in mammals, including man, which comprises administering to a mammal in need thereof an effective amount of at least one compound of claim 1.

11. A method according to claim 10 wherein the compound is administered orally and the effective amount is from 0.001 to 5 mg/kg of body weight.

12. A method according to claim 11 wherein the effective amount is from 0.01 to 1 mg/kg of body weight.

* * * * *

UNITED STATES PATENT AND TRADEMARK OFFICE
CERTIFICATE OF CORRECTION

PATENT NO. : 5,272,170
DATED : December 21, 1993
INVENTOR(S) : Carmen Almansa et al.

Page 1 of 3

It is certified that error appears in the above-identified patent and that said Letters Patent is hereby corrected as shown below:

On the cover, Item [56] in the Other Publications section (Co 2, line 1), "1964;" should be --1964,--.

Col. 1, line 63, "1,2-dihydor-2-oxo-1-pyridyl" should be --1,2-dihydro-2-oxo-1-pyridyl--.

Col. 4, line 19, after "of a" insert --compound of formula I into a thiocarbonyl group, by treatment with a--.

Col. 4, line 27, after "are" insert --hydrogen, reacting a compound of formula I wherein $R^5$ is hydroxyl and $R^6$ and $R^7$ are--.

Col. 8, line 19, "see" should be --sec--.

Col. 17, formula 39 should be changed from

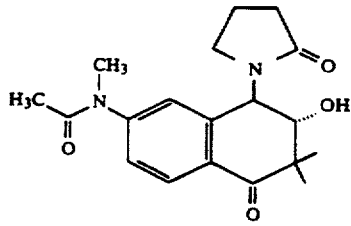

to

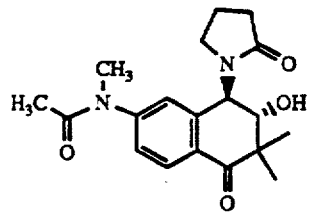

UNITED STATES PATENT AND TRADEMARK OFFICE
CERTIFICATE OF CORRECTION

PATENT NO. : 5,272,170

DATED : December 21, 1993

INVENTOR(S) : Carmen Almansa et al.

It is certified that error appears in the above-identified patent and that said Letters Patent is hereby corrected as shown below:

Col. 18, delete formula 42 (a repeat of formula 41) and insert the following

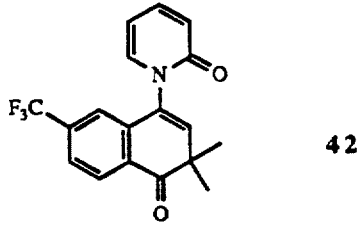

Col. 29, line 26, "tric-film" should be --tric film--.

Col. 31, line 19, after "1290" insert --1260--.

Col. 46, line 43, "72.27" should be --75.27-- and; "6.72" should be --6.71--.

Col. 47, line 37, after "41%)." start a new paragraph.

Col. 49, line 32, "1558" should be --1585--.

Col. 49, line 64, "3hydroxy" should be --3-hydroxy--.

Col. 50, line 29, "2oxo" should be --2-oxo--.

Col. 51, line 55, "J=8" should be --J=8.3--.

Col. 51, line 56, "broad s" should be --broad d--.

Col. 52, line 3, "M.p:" should be --M.p.:--.

Col. 53, line 66, "oxonaphthalene" should be --oxonaphthalen--

UNITED STATES PATENT AND TRADEMARK OFFICE
CERTIFICATE OF CORRECTION

PATENT NO. : 5,272,170

DATED : December 21, 1993

INVENTOR(S) : Carmen Almansa et al.

It is certified that error appears in the above-identified patent and that said Letters Patent is hereby corrected as shown below:

Col. 54, line 43, "CHN" should be --CHO--.

Col. 55, line 15, "after Ar)," insert --7.72 (d, J=8Hz, 1H, Ar),--.

Col. 58, line 44, "2973" should be --2937--.

Col. 66, line 63, "1.86" should be --0.86--.

Signed and Sealed this

Second Day of May, 1995

Attest:

BRUCE LEHMAN

Attesting Officer    Commissioner of Patents and Trademarks